US012685665B2

(12) United States Patent
     Ghuge

(10) Patent No.: US 12,685,665 B2
(45) Date of Patent: *Jul. 21, 2026

(54) MAXILLARY AND MANDIBULAR DEVICES THAT PREVENT DISENGAGEMENT THEREBETWEEN, CONTROLLER STATION, AND METHODS OF TREATING AND/OR DIAGNOSING MEDICAL DISORDERS

(71) Applicant: Sleep Solutions of Texas, LLC, Tyler, TX (US)

(72) Inventor: Raghavendra Vitthalrao Ghuge, Tyler, TX (US)

(73) Assignee: SLEEP SOLUTIONS OF TEXAS, LLC, Tyler, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/225,711

(22) Filed: Jun. 2, 2025

(65) Prior Publication Data

US 2025/0288454 A1     Sep. 18, 2025

Related U.S. Application Data

(63) Continuation of application No. 17/366,421, filed on Jul. 2, 2021, now Pat. No. 12,318,325.

(51) Int. Cl.
     *A61F 5/56* (2006.01)
     *A61B 5/00* (2006.01)
     (Continued)

(52) U.S. Cl.
     CPC ............ *A61F 5/566* (2013.01); *A61B 5/0205* (2013.01); *A61B 5/021* (2013.01); *A61B 5/082* (2013.01);
     (Continued)

(58) Field of Classification Search
     CPC .. A61F 5/56; A61F 5/563; A61F 5/566; A61F 2005/56; A61F 2005/563;
     (Continued)

(56) References Cited

U.S. PATENT DOCUMENTS

| | | | |
|---|---|---|---|
| 2011/0168187 A1* | 7/2011 | Nelissen | ................. A61F 5/566 |
| | | | 128/848 |
| 2016/0184129 A1 | 6/2016 | Liptak et al. | |
| 2019/0033826 A1 | 1/2019 | Kim et al. | |

* cited by examiner

*Primary Examiner* — Alireza Nia
*Assistant Examiner* — Gina McCarthy
(74) *Attorney, Agent, or Firm* — FisherBroyles, LLP; Susan M. Oiler

(57) ABSTRACT

Mandibular repositioning devices providing downward movement as well as forward movement of the mandible have a maxillary tooth covering having a driver flange protruding laterally outward on one or both sides thereof and have a mandibular tooth covering having a protrusive flange extending cranially therefrom positioned to have a posterior side engaged with the anterior side of each driver flange. The anterior side of each driver flange has a convex curvature. The posterior side of each protrusive flange has a concave-to-convex curvature positioned to move the convex portion thereof along the convex curvature of the driver flange when the mouth opens, which also moves the mandible forward. A plateau of a preselected height, which prevents disconnect between each protrusive flange and its respective driver flange relative to a fully open mouth measurement, is present between the base of the protrusive flange and the tooth covering.

16 Claims, 26 Drawing Sheets

(51) Int. Cl.

| | |
|---|---|
| *A61B 5/0205* | (2006.01) |
| *A61B 5/021* | (2006.01) |
| *A61B 5/08* | (2006.01) |
| *A61B 5/087* | (2006.01) |
| *A61B 5/091* | (2006.01) |
| *A61B 5/318* | (2021.01) |

(52) U.S. Cl.
CPC .............. *A61B 5/087* (2013.01); *A61B 5/091* (2013.01); *A61B 5/318* (2021.01); *A61B 5/4836* (2013.01); *A61B 2560/02* (2013.01); *A61B 2560/04* (2013.01)

(58) Field of Classification Search
CPC ... A63B 71/085; A61B 5/0205; A61B 5/0201; A61B 5/318; A61B 5/4557; A61B 5/4818; A61B 5/4836; A61B 5/682; A61B 2560/04; A61C 7/002; A61C 7/08; A61C 7/36

See application file for complete search history.

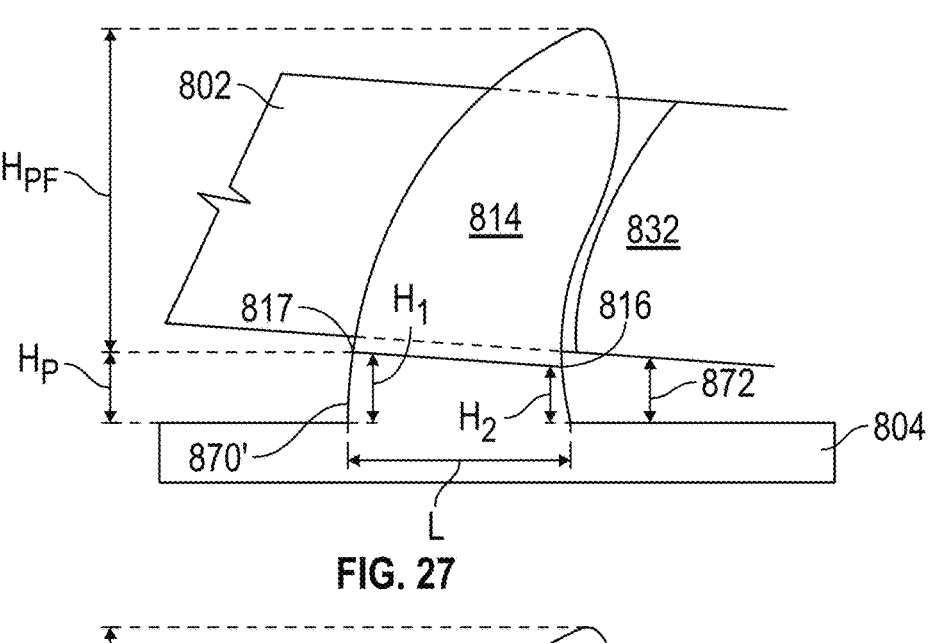
FIG. 27
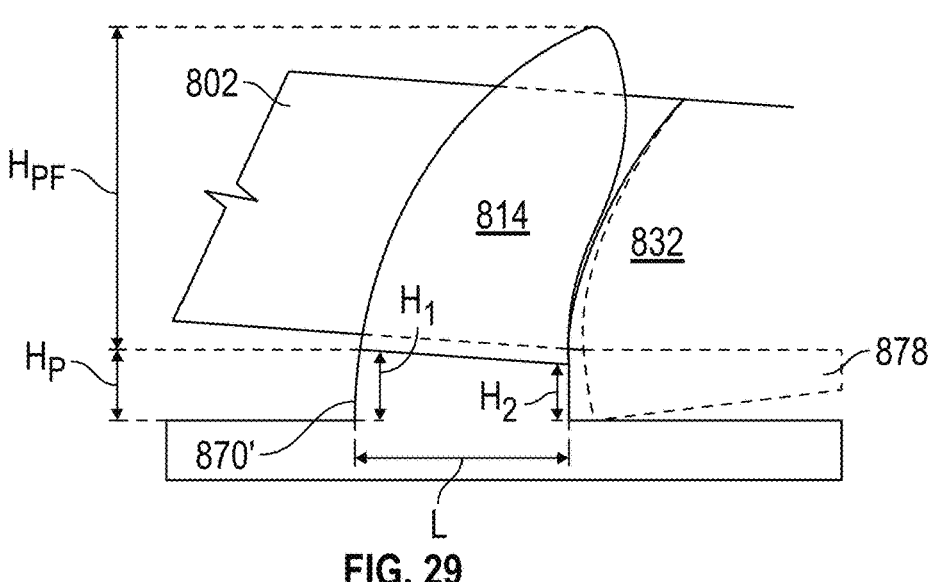
FIG. 28
FIG. 29

FIG. 30

COMBINED EFFECT OF ANTERIOR AND VERTICAL ADVANCEMENT OF MANDIBLE (TAVMLRD)

| PLATEAU HEIGHT (mm) | MOUTH OPENING (degrees) | MOUTH OPENING* (mm) | ANTERIOR MOVEMENT IN THE AT REST POSITION | | | | | | | |
|---|---|---|---|---|---|---|---|---|---|---|
| | | | 0 mm | 1 mm | 2 mm | 3 mm | 4 mm | 5 mm | 6 mm | |
| 1.06 | 1 | 1.66 | 1.25 | 2.25 | 3.25 | 4.25 | 5.25 | 6.25 | 7.25 | AREA 0 |
| 2.12 | 2 | 3.31 | 2.50 | 3.50 | 4.50 | 5.50 | 6.50 | 7.50 | 8.50 | AREA 1 |
| 3.18 | 3 | 4.97 | 3.75 | 4.75 | 5.75 | 6.75 | 7.75 | 8.75 | 9.75 | AREA 2 |
| 4.24 | 4 | 6.62 | 5.00 | 6.00 | 7.00 | 8.00 | 9.00 | 10.00 | 11.00 | AREA 3 |
| 5.3 | 5 | 8.28 | 6.25 | 7.25 | 8.25 | 9.25 | 10.25 | 11.25 | 12.25 | |
| 6.36 | 6 | 9.93 | 7.50 | 8.50 | 9.50 | 10.50 | 11.50 | 12.50 | 13.50 | |
| 7.42 | 7 | 11.59 | 8.75 | 9.75 | 10.75 | 11.75 | 12.75 | 13.75 | 14.75 | AREA 4 |
| 8.48 | 8 | 13.24 | 10.00 | 11.00 | 12.00 | 13.00 | 14.00 | 15.00 | 16.00 | |
| 9.54 | 9 | 14.90 | 11.25 | 12.25 | 13.25 | 14.25 | 15.25 | 16.25 | 17.25 | |
| 10.6 | 10 | 16.55 | 12.50 | 13.50 | 14.50 | 15.50 | 16.50 | 17.50 | 18.50 | AREA 5 |
| 11.66 | 11 | 18.21 | 13.75 | 14.75 | 15.75 | 16.75 | 17.75 | 18.75 | 19.75 | |
| 12.72 | 12 | 19.86 | 15.00 | 16.00 | 17.00 | 18.00 | 19.00 | 20.00 | 21.00 | |
| 13.78 | 13 | 21.52 | 16.25 | 17.25 | 18.25 | 19.25 | 20.25 | 21.25 | 22.25 | |
| 14.84 | 14 | 23.17 | 17.50 | 18.50 | 19.50 | 20.50 | 21.50 | 22.50 | 23.50 | |
| 15.9 | 15 | 24.83 | 18.75 | 19.75 | 20.75 | 21.75 | 22.75 | 23.75 | 24.75 | |
| 16.96 | 16 | 26.48 | 20.00 | 21.00 | 22.00 | 23.00 | 24.00 | 25.00 | 26.00 | |
| 18.02 | 17 | 28.14 | 21.25 | 22.25 | 23.25 | 24.25 | 25.25 | 26.25 | 27.25 | |
| 19.08 | 18 | 29.79 | 22.50 | 23.50 | 24.50 | 25.50 | 26.50 | 27.50 | 28.50 | |
| 20.14 | 19 | 31.45 | 23.75 | 24.75 | 25.75 | 26.75 | 27.75 | 28.75 | 29.75 | AREA 6 |
| 21.2 | 20 | 33.10 | 25.00 | 26.00 | 27.00 | 28.00 | 29.00 | 30.00 | 31.00 | |
| 22.26 | 21 | 34.76 | 26.25 | 27.25 | 28.25 | 29.25 | 30.25 | 31.25 | 32.25 | |
| 23.32 | 22 | 36.41 | 27.50 | 28.50 | 29.50 | 30.50 | 31.50 | 32.50 | 33.50 | |
| 24.38 | 23 | 38.07 | 28.75 | 29.75 | 30.75 | 31.75 | 32.75 | 33.75 | 34.75 | |

*φ2 = 42 MM = Radius of trailing superior curvature of the protrusive flange as labeled in FIG. 21

FIG. 31

THEORETICAL
POST-TREATMENT AIRWAY DMENSIONS AND OXYGENATION IN MILD/MODERATE OSA USING
FIXED 2-3 MM VERTICAL AND 5-6 MM ANTERIOR MANDIBULAR ADVANCEMENT (Area 1)

| PARAMETER | PRE-TREATMENT | | POST-TREATMENT | | ABSOLUTE CHANGE | | PERCENTAGE CHANGE | |
|---|---|---|---|---|---|---|---|---|
| | MEAN | SD | MEAN | SD | MEAN | SD | MEAN | SD |
| EPWORTH Sleepiness Scale | 18.54 | 3.17 | 5.21 | 1.51 | -13.33 | 3.3 | -71.90% | 21.47% |
| Oxygen Saturation (%) | 87.97 | 4.43 | 94.89 | 1.54 | 6.92 | 4.3 | 7.87% | 5.15% |
| Airway Volume (mm³) | 12140 | 4773.9 | 14500 | 5114.6 | 2360 | 5.3 | 19.44% | 0.07% |
| SMCA of Upper Airway (mm) | 81.95 | 55.23 | 128.5 | 54.78 | 46.55 | 6.3 | 56.80% | 23.58% |
| Anterior-posterior-SMCA (mm) | 4.9 | 1.65 | 8.01 | 2.04 | 3.11 | 7.3 | 63.47% | 224.62% |
| Transverse-SMCA (mm) | 27.67 | 8.52 | 31.94 | 8.59 | 4.27 | 8.3 | 15.43% | 43.34% |

FIG. 32

ACTUAL
POST-TREATMENT DATE AND OXYGENATION IN SEVERE OSA USING
0 mm Anterior Advancement at Rest, 23 mm Vertical advancement, a 17.5 mm combined Effect

| PARAMETER | Pre-Treatment | BIPAP | AVMLRD | BIPAP Effect | AVMLRD Effect | \|AVMLRD over BIPAP\| |
|---|---|---|---|---|---|---|
| Total Sleep Time (min) | 360 | 365 | 465 | 1.4% | 22.6% | 21.5% |
| Apnea Hypopnea Index | 32 | 6.3 | 4.8 | -407.9% | -566.7% | 31.3% |
| Respiratory Disturb Index | 37 | 12.9 | 8.6 | -186.8% | -330.2% | 50% |
| Oxygen Saturation (%) | 76 | 84 | 88 | 9.5% | 13.6% | 4.5% |
| REM Sleep (%) | 12.5 | 8.48 | 25.37 | -47.4% | 50.7% | 66.6% |
| Sleep Efficiency (%) | 76.5 | 78.44 | 88.74 | 2.5% | 13.8% | 11.6% |
| Deep Sleep (%) | 10.5 | 15.59 | 16.96 | 32.6% | 38.1% | 8.1% |

MAXILLARY AND MANDIBULAR DEVICES THAT PREVENT DISENGAGEMENT THEREBETWEEN, CONTROLLER STATION, AND METHODS OF TREATING AND/OR DIAGNOSING MEDICAL DISORDERS

TECHNICAL FIELD

This application relates to maxillary and mandibular devices, more particularly, to such devices that provide anterior to posterior advancement and cranial to caudal advancements to the mandible while preventing disengagement between the maxillary and mandible pieces during such advancements.

BACKGROUND

Many individuals suffer from disordered breathing while asleep and many others have a smallest concentric airway size while awake. Some example disorders include obstructive sleep apnea (OSA), snoring, snore arousals, sleep-related hypoxia, and other conditions dependent on and caused by snoring or OSA. OSA is a condition in which sleep is repeatedly interrupted by an inability to breathe, which is typically a results of intermittent obstruction of the airway by the tongue and a general relaxation of the muscles which stabilize the upper airway segment, which can cause a lack of oxygen, snoring, cardiovascular and neurological complications, such as sleep-induced hypertension, heart attacks, cardiac arrythmias, strokes, Alzheimer's disease, hypertension, sleep-induced hypertension, diabetes, weight gain, and depression.

The smallest concentric airway cross-sectional area (SMCA) of a normal adult, on average, is about 149 mm$^2$. This is the narrowest point in an adult human airway. Many humans have much smaller airways as shown by cone CT scans of the airway. It has been seen that OSA patients have an SMCA on average of about 40 mm$^2$-67 mm$^2$. In OSA, the mandible lowers to a greater degree than in normal sleep due to activation of the upper airway muscles (due to lack of oxygen) allowing traction on hyoid bone and mouth opening to facilitate mouth breathing. However, this lowering of the mandible comes at a price of reducing the antero-posterior diameter of the airway due to posterior movement of the mandible and tongue in the second half of the lowering process (the second 13○). Anterior (sagittal) repositioning of the mandible alone does not counteract this part of physiology. Studies have shown that vertical (caudal) repositioning of the mandible has a greater influence on increasing the transverse diameter of the SMCA than anterior repositioning. Moreover, it is believed that simultaneously advancing the mandible sagittally while advancing it caudally can mitigate airway narrowing that occurs during voluntary mouth opening in OSA. Both such repositionings increase the AP diameter and transverse diameter of the SMCA simultaneously. These simultaneous increase in AP and transverse diameters effectively incrementally increases the SMCA.

Mandibular repositioning devices have been FDA-approved and used as a treatment for sleep apnea when treatment by a CPAP (Continuous Positive Airway Pressure) machine has been ineffective for the particular patient, or when a patient is unable to tolerate a PAP (Positive Airway Pressure) device. Most oral appliances on the market have only been able to control approximately 50% of sleep apnea events. There are a large number of patients that are intolerant to PAP devices, some due to the PAP device or the mask but most due to excessive high air pressure that may be medically recommended for keeping an open airway. Repeated adjustments have to be performed in attempts to make intolerant patients tolerate a PAP device, most of which require manual adjustments by a professional or require repeated sleep studies after a sleep study. Since a large number of patients with OSA have thus remained untreated due to various reasons, there is a serious need for a new method of treatment that can maintain an open airway during sleep using a combination of jaw stabilization and simultaneous vertical (caudal) and anterior (sagittal) advancement of the jaw and tongue, i.e., a dynamic mandibular and lingual repositioning device as disclosed herein.

There is a need for improvement in mandibular repositioning devices to maintain contact between the mandibular piece and maxillary piece, i.e., prevent disengagement thereof, during anterior-posterior repositioning and cranial-caudal repositioning, especially when both types of repositioning occur simultaneously. In particular, the improvements disclosed herein may be useful for users that are capable of opening their mouth wider than the length of the protrusive flange on the mandibular piece.

SUMMARY

The features introduced herein to prevent disengagement of the protrusive flange from the driver flange are accomplished without restricting the degrees of mouth opening and jaw advancement of the user. By providing mandibular repositioning devices that enable both anterior-posterior adjustment and cranial caudal adjustment, a greater range in flexibility to treat severe OSA results while allowing the user the ability to open their mouth is an unrestricted manner. Moreover, the AVMLRD device takes advantage of the correlation between mandible movements and apnea/hypopnea events by providing increasing sagittal and vertical mandibular adjustment as the jaw opens. This means that as an apnea/hypopnea event begins and the jaw opens, the AVMLRD will advance the mandible further, increasing pharyngeal space, increasing airflow, and reducing the likelihood of an apnea/hypopnea event or waking event. The combination of these two design features in the AVMLRD intraoral device provide a novel method of treating severe OSA which is not currently available on the market.

In all aspects, mandibular repositioning devices are disclosed that have a maxillary piece having a tooth covering with a driver flange protruding laterally outward on a right side proximate a backmost teeth mold and/or on a left side proximate a backmost teeth mold, and a mandibular piece having a tooth covering with a protrusive flange extending cranially therefrom positioned to have a posterior side engaged with the anterior side of each driver flange. Each driver flange has an anterior side with a convex curvature. Each protrusive flange has a posterior side having a concave-to-convex curvature from its base toward its most cranial point. The convex portion of the concave-to convex curvature engages the convex curvature of the driver flange in an rest position. Here, a plateau of a preselected height is present between the base of the protrusive flange and the tooth covering. The preselected height of the plateau prevents disconnect between each protrusive flange and its respective driver flange relative to a fully open mouth measurement between incisors of the user. The mandibular repositioning devices provide both downward movement and forward movement of the mandible of the user.

In all aspects, the convex portion of the curvature of the protrusive flange engages with the convex curvature of the driver flange at a point that is two thirds of the height of the driver flange. The protrusive flange and the driver flange are positioned to place an engagement point of the convex portion of the concave-to convex curvature with the convex curvature of the driver flange at a midpoint length that is at half the lineal distance from a vertical axis at the front of the incisors (incisor vertical axis) to a point on a parallel vertical axis aligned with the temporo-mandibular joint (TMJ) at rest (TMJ vertical axis). The majority of the convex curvature of the driver flange is defined by an arc having a center at a point on the TMJ vertical axis that is one third of the height of the driver flange measured from the horizontal dental axis and has a radius length equal to the midpoint length. A convex curvature of the convex portion of the protrusive flange is defined by an arc having a center at a point on the incisor vertical axis that is at two thirds the height of driver flange measured from the horizontal dental axis and has a radius length equal to the midpoint length.

In all embodiments, the plateau can extend across the full width of the tooth covering. In one embodiment, the plateau is wedge-shaped, has a first height at the anterior base of the protrusive flange, a second height at the posterior base of the protrusive flange, and the first height is greater than the second height; and wherein the protrusive flange and driver flange are inclined equivalently to the plateau to maintain the engaged convex portion to convex curvature thereof. In some embodiments, the wedge-shaped plateau extends posteriorly to a posterior terminus of the tooth covering and terminates with a third height that is smaller than the first height and the second height, and in other embodiments, terminates posteriorly at the posterior base of the protrusive flange and the driver flange extends caudally with its anterior side extending the convex curvature thereof past the posterior base of the protrusive flange into a gap defined by the plateau between the maxillary piece and the mandibular piece or extends caudally on the buccal side of the mandibular piece beyond the plateau of the mandibular piece. In all embodiments, the protrusive flange has a flange of or less than 20 mm.

In all embodiments, the protrusive flange can be removably replaceably attached to the mandibular piece. The protrusive flange slides into the tooth covering of the mandibular piece from a rear surface and engagingly saddles the dental crown against cranial movement. The dental crown defines a keyway having opposed elongate grooves, one each open in the buccal and lingual directions, and defining a tongue above the opposed elongate grooves, and wherein the protrusive flange has a keyed slider configured to slidingly mate to the keyway of the dental crown.

Likewise, in all embodiments, the driver flange is removably replaceably attached to the maxillary piece. The driver flange has a posteriorly extending post receivable in a slot having an anterior opening and being buccally juxtaposed to the backmost teeth mold of the maxillary piece.

In another aspect, the maxillary piece has a housing proximate one or both of a left molar portion and a right molar portion, wherein each housing encloses a power source electrically connected to a motor and to a microprocessor and has a driver operatively connected to a means for moving the driver flange for anterior-posterior movement and cranial-caudal movement or the mandibular piece has a housing proximate one or both of a left molar portion and a right molar portion, wherein each housing encloses a power source electrically connected to a motor and to a microprocessor and has a driver operatively connected to a means for moving the protrusive flange for anterior-posterior movement, angular movement, and cranial-caudal movement.

The means for moving the driver flange comprises a piezo-electric motor and an internal robotic armature positioned for repositioning of the piezo-electric motor as the cranial-caudal movement, or robotic arms connected to integrated plates in the driver flange, or robotic arms connected to separate plates for the independent cranial-caudal movement and anterior-posterior movement of the driver flange. The cranial-caudal movement of the means for moving the drive flange is synergistic to the cranial-caudal movement of the protrusive flange. The devices can also have one or more sensors positioned in the user's oral cavity in operative communication with the microprocessor within each housing of the maxillary piece. The microprocessor has nontransitory memory having stored therein a first algorithm controlling the cranial-caudal movement of the piezo-electric motor relative to data from the one or more sensors. The one or more sensors measure airway cross-sectional area, airflow volume, airflow velocity, systolic and diastolic blood pressure, electrical activity of the heart, oxygen level, and combinations thereof. In one embodiment, the microprocessor has a quantum microchiplet and/or a photonic integrated circuit. The devices can also include position sensors measuring a first distance for cranial-caudal movement and a second distance for anterior-posterior movement of the driver flange. The microprocessor can include a second algorithm for anterior-posterior movement under the influence of medication, sedation, anesthesia, or alcohol.

In another aspect, mandibular repositioning device kits are disclosed. The kit includes a maxillary tooth covering having an elongate slot in a buccally adjacent portion of the tooth covering most proximate both a right and a left backmost teeth mold and a left and right driver flange pair that each have a post slidingly receivable in one of the elongate slots of the maxillary tooth covering and having an anterior side with a convex curvature. Each driver flange is removably replaceable. The kit also includes a mandibular tooth covering having an elongate keyway extending anteriorly from each rear surface most proximate a right and a left backmost teeth mold and a left and right protrusive flange pair each slidably mountable to one of the elongate keyways of the mandibular piece. Each protrusive flange, once slidably mounted to the mandibular piece, extends cranially from the mandibular piece and has a posterior side engageable with the anterior side of a respective one of the driver flanges. The posterior side of each protrusive flange has a concave-to-convex curvature from its base toward its most cranial point and a convex portion of the concave-to convex curvature engages the convex curvature of the driver flange in a rest position. In use, downward movement of the mandibular piece moves the convex portion of the posterior side of the protrusive flange along the convex curvature of the driver flange, thereby moving a user's mandible forward while opening the user's mouth.

The kit can include plurality of left and right protrusive flange pairs, where at least one of the left and right protrusive flange pairs each have a plateau of a preselected height between a base of each protrusive flange and a keyed slider extending caudally from the protrusive flange. The preselected height of the plateau prevents disconnect between each protrusive flange and its respective driver flange relative to a fully open mouth measurement between incisors of the user. Each protrusive flange engagingly saddles either a left backmost teeth mold or a right backmost teeth mold of the mandibular piece against cranial movement, and each elongate keyway has opposed elongate grooves, one each open in buccal and lingual directions, and defining a tongue above the opposed elongate grooves. The protrusive flange has a keyed slider configured to slidingly mate to the keyway of the dental crown.

The kit can include a plurality of left and right protrusive flange pairs differing in protrusive flange height, angle, posterior side distance from the rear surface, and combinations thereof. The kit can also include a plurality of left and right driver flange pairs differing in width, convex curvature of the anterior side, posterior lean, and combinations thereof.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present system.

FIG. 27 is a side view of an alternate embodiment for a protrusive flange having a mandibular plateau that is wedge shaped.

FIG. 28 is a side view of the embodiment of FIG. 27 with the mandibular plateau extended to the posterior surface to fill the gap shown in FIG. 27 created between mandibular piece and the maxillary piece.

FIG. 29 is a side view of a maxillary piece having a driver flange that is extended caudally, represented by the dashed lines to fill the gap shown in 27 created between mandibular piece and the maxillary piece.

FIG. 30 is a chart of plateau height and combined cranial-caudal repositioning and anterior-posterior repositioned effect.

FIG. 31 is a chart of theoretical post treatment airway dimension and oxygenation in severe and moderate OSA when using an AVMLRD disclosed herein.

FIG. 32 is a chart of actual post-treatment data using an AVMLR as compared to a BiPAP machine for a selected user.

DETAILED DESCRIPTION

Figure 1:
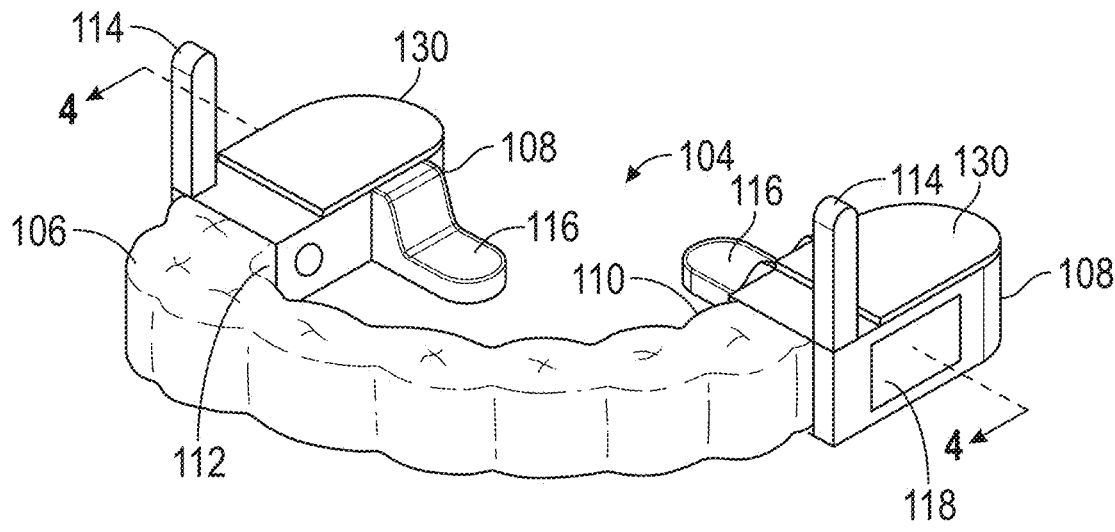
FIG. 1 is a left-side view of a first embodiment of a mandibular lingual repositioning device.

The following detailed description will illustrate the general principles of the invention, examples of which are additionally illustrated in the accompanying drawings. In the drawings, like reference numbers indicate identical or functionally similar elements.

Figure 2:
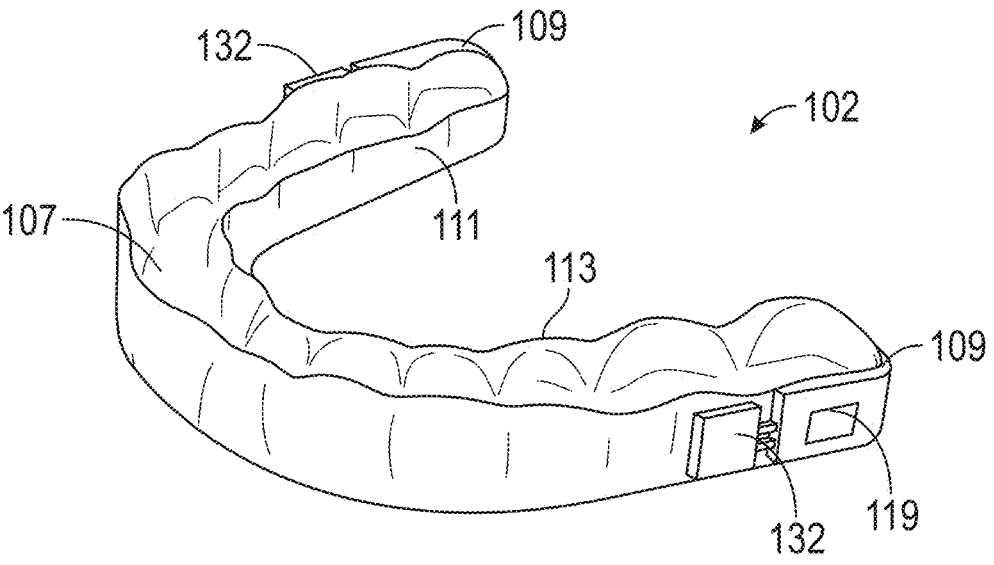
FIG. 2 is a side, perspective view of the mandibular piece of the mandibular lingual repositioning device of FIG. 1.
Figure 3:
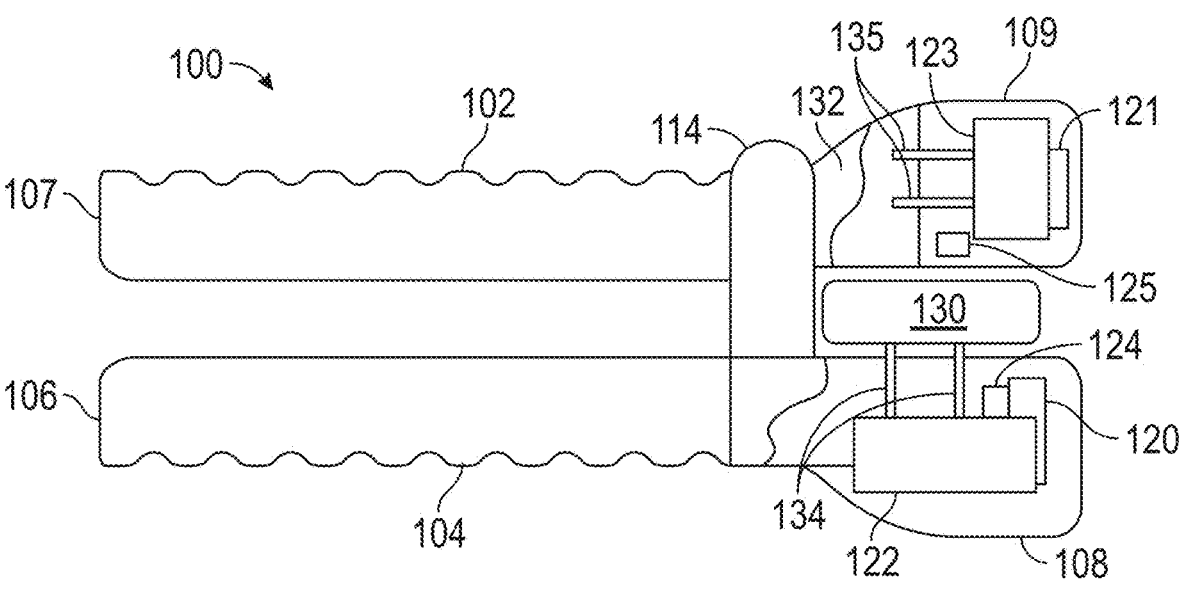
FIG. 3 is a side, perspective view of the maxillary piece as it articulates and fits with the mandibular lingual repositioning device of FIG. 1.

Referring now to FIGS. 1 to 4, a mandibular lingual repositioning device (MLRD) that is dynamic in its movement of the jaw(s) and tongue is represented collectively in FIG. 3 by reference number 100. The MLRD 100 has a maxillary piece 102 seated on a mandibular piece 104 for operative communication of drivers built therein.

Figure 4:
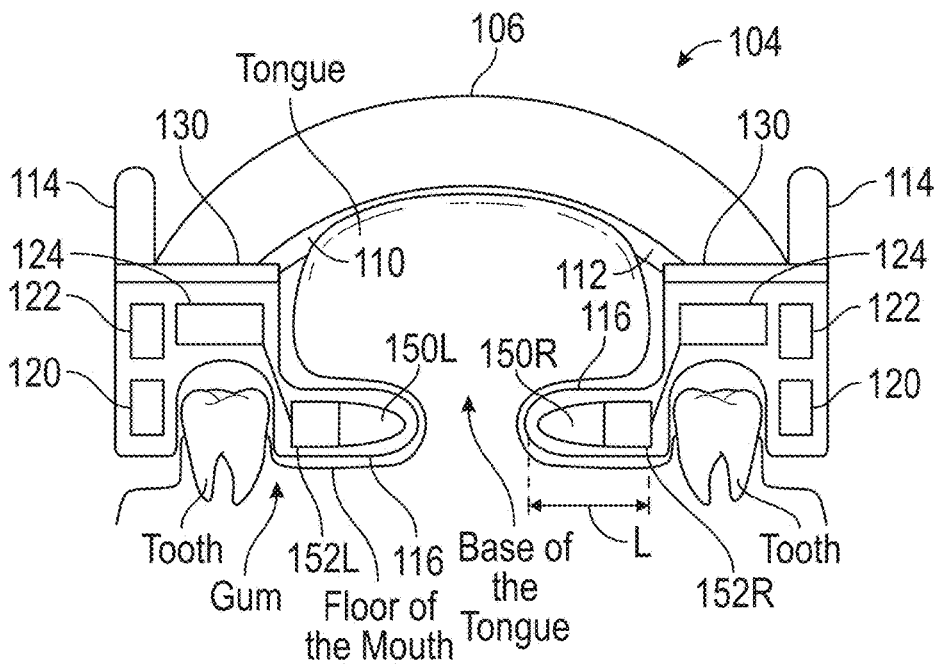
FIG. 4 is a cross-sectional view of the mandibular lingual repositioning device along line 4-4 in FIG. 1.

Turning to FIGS. 1 and 4, the mandibular piece 104 is shown, which has a first teeth covering 106 and has a housing 108 proximate each of a left molar portion 110 and a right molar portion 112. A protrusive flange 114 extends cranially from each housing 108, and a stimulator 116 extends from each housing 108 toward the tongue at a position to lie under the tongue in contact with lingual muscles, in particular the Genioglossus (GG), the Geniohyoid (GH), sub-mentalis (SM), and Glossopharyngeal (GP) muscles. The stimulator protrusion 116 of each housing 108 should be fitted to the user/custom made for the user to ensure proper contact with the lingual muscles. Each stimulator portion 116 while appearing somewhat boxy-looking in the drawings, is more preferably molded of moldable material suitable for use in a human oral cavity and has smooth transitions to its shape and is shaped to match the shape of the user's mouth, especially to sit under the tongue in contact with the base of the tongue and the floor of the mouth as shown in FIG. 4.

The moldable material may be any of those commercially available or hereinafter developed for use in a human oral cavity. The moldable material can be shaped and sized to fit the entire tongue like a glove or sock. It may also retain the tongue in its awake position thereby preventing it from falling back passively into the airway while asleep whilst still allowing voluntary movements of the tongue such as involved in speech and swallowing. The moldable material could also extend from the molar left side all the way to the front and then to the right side, thus fitting like a horse-shoe around the base of the tongue so as to evenly electrify all components of the muscles it comes in contact with when an electrical stimulator is present.

Referring now to the transverse cross-section of FIG. 4, each housing 108 encloses, in a fluid-tight manner, a power source 120 electrically connected to a motor 122, to a circuit board 124, and to the stimulator 116. A first driver 130 is operatively connected to each motor 122 for cranial to caudal adjustments of the device 100. The first driver 130 is linearly translatable by linkages 134 operatively connected to the motor 122 within its housing 108 as shown in FIG. 3. The linkages 134 will be fluid-proof, heat-resistant and acid-resistant and thus able to withstand the conditions found within the oral cavity of a user.

With reference to FIGS. 2 and 3, the maxillary piece 102 is shown, which has a second teeth covering 107 and has a housing 109 proximate each of a left molar portion 111 and a right molar portion 113. Referring to the partial cross-sectional view of FIG. 3, each housing 109 encloses a power source 121 electrically connected to a motor 123 and to a circuit board 125. A second driver 132 is operatively connected to each motor 123 for anterior to posterior adjustments of the device 100. The second driver 132 is linearly translatable by linkages 135 operatively connected to the motor 123 within its housing 109.

In all embodiments, the housings 108 and 109 may be fixedly attached to the respective teeth covering, integral therewith, or removable attachable thereto. When removable attachable, the housings 108, 109 may be slid over a molar portion of the teeth covering, have a snap fit thereto, an interference fit thereto, may be a two-piece compartment that snaps together over a predetermined location of the teeth covering, may be three-dimensionally printed to cover or fit over a portion of the teeth covering. In all embodiments, while the teeth coverings 106, 107 are shown as full coverings for all teeth in the mandible and all teeth in the maxilla, the teeth coverings are not limited thereto. Instead, each teeth covering may be a partial cover for one or more teeth, as such, the mandibular piece 104 may be a two-part configuration having a left and a right portion each with a housing 108 and the maxillary piece 102 may be a two-part configuration having a left and a right portion each with a housing 109.

In all embodiments herein, each housing 108, 109 is described herein as positioned proximate a molar portion of a teeth covering, but is not limited to any particular size, i.e., the number of teeth to which it is associated. Each housing may be associated with one tooth region, a two-tooth region, a three-tooth region, or whatever number of teeth is needed to accommodate the size and position of the housing and its stimulator protrusion.

Figure 6:
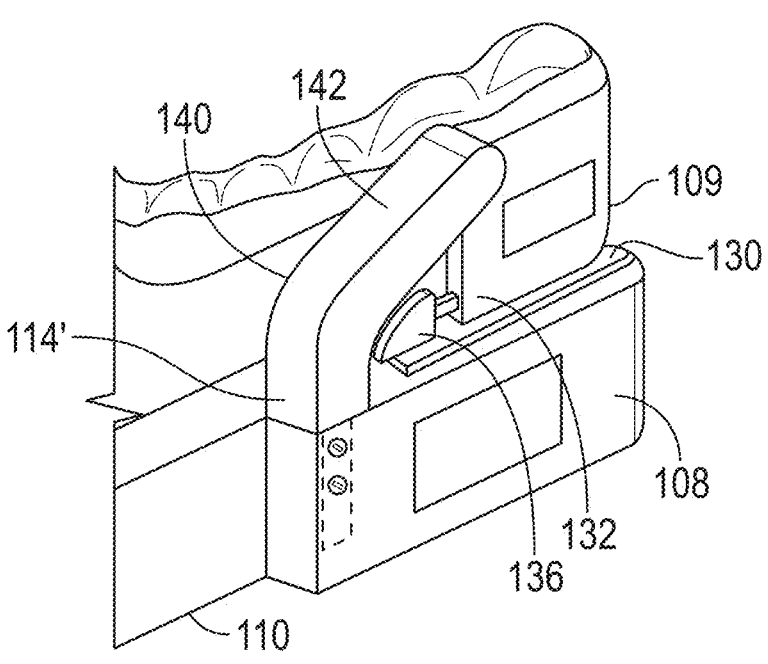
FIG. 6 is an enlarged view of the left movement mechanism of the mandibular lingual repositioning device of FIG. 1.
Figure 7:
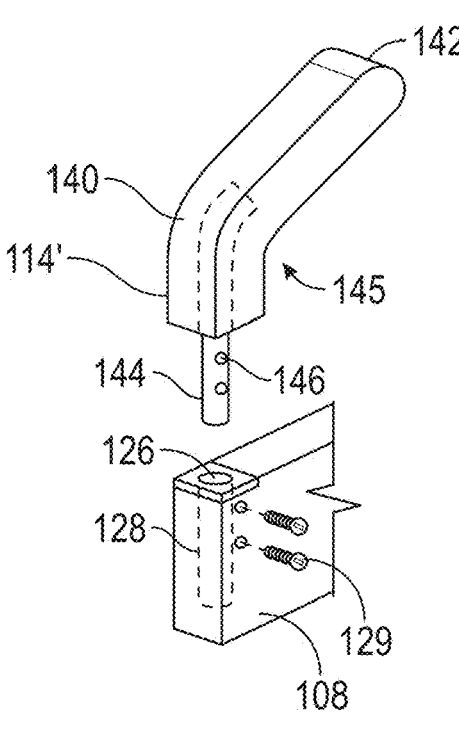
FIG. 7 is a an enlarged view of an alternate embodiment of the left movement mechanism of the mandibular lingual repositioning device.

Referring to FIGS. 1, 3, and 4, the protrusive flange 114 of the mandibular piece 104 is an elongate flange that is releasably, removably attached to or may be integral with the housing 108. A releasably, removably attachable protrusive flange 114 is shown in FIGS. 6 and 7 to accommodate an interchangeability of protrusive flanges 114 of different shapes and sizes to provide the best fit for the user's mouth. In the embodiment of FIG. 1, the protrusive flanges 114 are generally an elongate linear flange protruding cranially from each of the housing 108. The protrusive flange 114 may be a housing containing within an antenna, a receiver-transmitter for two-way communication, an infrared homing or signaling device, a unique signature emitting device, an encoder or a multi-polarity magnetic clasp that facilitates coordinated movements with the second driver 132 with which the protrusive flange 114 articulates.

Turning now to FIGS. 6 and 7, the protrusive flange 114' is releasably attachable to the housing 108 of the mandibular piece 104. The protrusive flange terminates with a post 144 opposite a free end 142 thereof. The post 142 includes a releasably attachable feature 146, such as a snap fit feature, a friction fit feature, or threaded holes as shown in FIG. 7. The housing 108 defines a receptacle 126 shaped to receive the post 144. The receptacle 126 will have a releasably attachable mating feature 128 that mates with the releasably attachable feature 146 of the post 144. In FIG. 7, the releasably attachable mating feature 128 is a set of threaded holes and screws 129.

Figure 8:
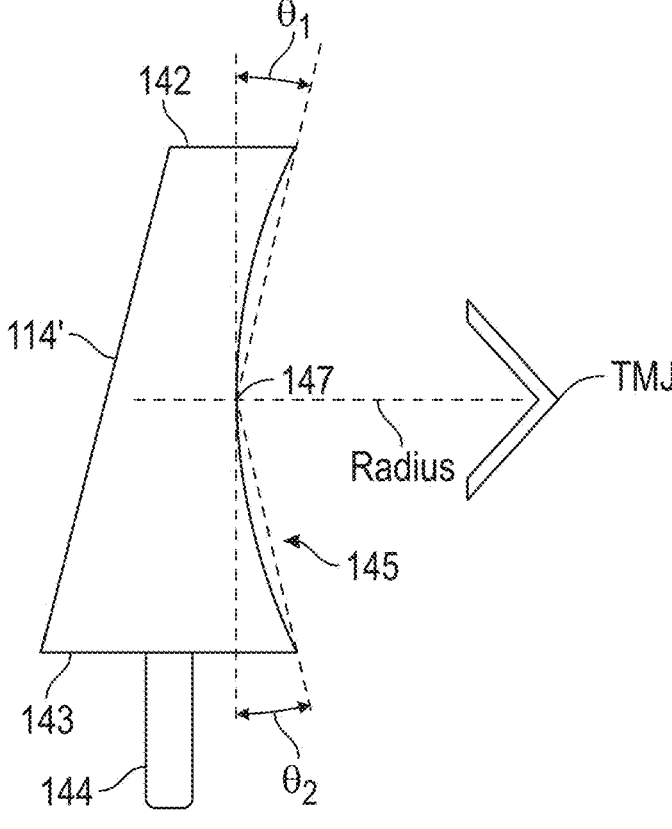
FIG. 8 is an enlarged side view of an embodiment of a protrusive flange.

As shown in FIGS. 6 and 7, the protrusive flange 114' can have a bend 140 on the anterior side of the flange, but this is not required. The new feature in this embodiment is that the posterior side 145 of the protrusive flange 114' is arcuately shaped as best shown in FIG. 8 as a concave surface, which mates with a driver 132 having a convex surface shaped to match the concavity of the posterior side 145. The protrusive flange 114 or 114' and its post 144 may lean posteriorly at any angle that may suit the need of a particular user. The midpoint 147, relative to being the middle or halfway point between the free end 142 and the opposing end 143, of the arcuately shaped posterior side 145 defines an arc of a circle having its center at the temporo-mandibular joint (TMJ) in this illustration and the free end 142 has a width that is smaller than a width of the opposing end 143 of the flange. The arc of the circle is one that defines $\theta_1$ as being any angle with the range of 12 degrees to 15 degrees in increments of whole degrees, half degree, or 0.2 degree increments. The angle of the arc $\theta_1$ defines the amount of protrusion of the mandible with each degree of mouth opening. The larger this angle $\theta_1$, the greater the protrusion with mouth opening. The larger the angle of mouth opening, the larger the protrusion of the mandible. Furthermore, a strong correlation between mandible movement and Apnea/Hypopnea events has been shown in the literature. Increased respiratory effort (due to OSA) is associated with increased mandibular movements and mouth opening. Data shows 98% (n=33) of open mouthing and large mandibular movement of 99.6% (n=33) were observed in OSA patients (children) who were confirmed to have OSA by polysomnography. "Mandibular movements were predominantly a change in position during increased upper airway resistance during the respiratory cycle as exhibited by mandibular lowering and jaw opening". Mandibular Movements Identify Respiratory Effort in Pediatric Obstructive Sleep Apnea (aasm.org). "The mandible is the anchor for upper airway muscles that dilate and elongate the pharynx and its position determines mouth opening. In OSA, the mandible lowers to a greater degree than in normal sleep due to activation of the upper airway muscles allowing traction on hyoid bone and mouth opening to facilitate mouth breathing".

The arcuate surface is customizable to provide a curvature that provides the best forward movement of the mandible for the user in relation to the individual user's mouth shape and size. Depending upon the shape and size of the user's mouth and jaws, the radius defining the point of the arc may be offset by moving this point up or down relative to the midpoint 147, which may change the widths of the free end 142 and the opposing end 143.

The advantage to the arcuately shaped side 145 of the protrusive flange 114' is that it will help protrude the mandible forward as the Temporo-Mandibular joint (TMJ) relaxes and the mouth falls open during sleep, wake or any other transitional state of the human mind (such as various Parasomnia create) thus allowing gradual smooth arcuate incremental forward mandibular movement to occur as concave surface 145 of protrusive flange 114' smoothly glides against convex surface 136 of driver 132'. The maximum protrusive distance (MPD) for anterior movement of the mandible is in a range of 0 mm to 15 mm, more typically 6 mm to 10 mm. Typically, the first 13 degrees of rotation of the mandible about the TMJ during natural, un-aided spontaneous mouth opening does not move the mandible anteriorly, i.e., this rotation does not change or open the airway. Drivers 130, 132 will actively coordinate simultaneous desired amount of vertical and protrusive movements of the mandible (controlled by controller) during this first 13 degrees of mouth opening while the arcuate opposing gliding movements of concave surface 145 of protrusive flange 114' smoothly against convex surface 136 of driver 132'surfaces will passively create mild forward movement of the mandible and tongue away from the airway, thus increasing the size of the airway. Driver 132 will ensure constant contact between surfaces 145 and 136 while driver 130 will adjust height of oral cavity through its own cranial movements that translate caudal mandibular advancement, facilitating mouth opening and thus increase oral cavity volume in order to create room for the advancing tongue while simultaneously stiffening the soft palate and Uvula (through the muscles palatoglossus, palatopharyngeus and tensor palatini). This entire process will work in synergy (keeping the person's sleep undisturbed) to increase cross-sectional area of upper airway and increase the cubic volume of the oral cavity which in turn allows 150L/R (through the controller) in 116 to appropriately incrementally protrude the base of tongue forward into the increased oral cavity volume utilizing electric stimulation of the tongue nerves and muscles (details described elsewhere in this document), further increasing the cross-sectional area of the upper airway (the tongue forms the anterior wall of the upper airway).

In the natural state, the mandible must rotate beyond this initial 13 degrees, typically through another 7 to 13 degrees to have an effect on the airway size. This natural movement comes at the price of reducing the antero-posterior (AP) diameter of the airway, thus constricting the airway. In an example, where the arcuately shaped side 145 is based on a 15 degrees jaw rotation (end to end) curvature, i.e., $q_1$ and $q_2$ are 15 degrees each or they may be any combination of two different angles that add up to 30 degrees. The approximate midpoint 147 of the arc 145 is the point at which transition between angle of $q_2$ and $q_1$ occurs and is approximately the point at which the mandible (mouth) is expected to have opened or rotated to the first 13 degrees (12 to 15 degree range). Total theta at the point of transition $147=180-(q_1+q_2)$. Surface 136 of driver 132 should align with the lower part of surface 145 closer to 143 when the mouth is completely closed (Centric Occlusion CO with a Centric Relation CR between mandibular and maxillary incisor teeth). Angle of $q_2$ can be different from angle of $q_1$, i.e. the arc may or may not be one fixed radius from TMJ. Each of the $q_1$ and $q_2$ should remain between the ranges of 12-15 degrees each although both $q_1$ or $q_2$ or both could be zero degrees each (0-15 degrees each). These angles could exceed 15 degrees each based on individual needs of the user/patient. Total of $(q_1+q_2)$ will ordinarily be between 24-30 degrees but could be 0-30 degrees or greater. Theta at point of transition 147 is $(180-(q_1+q_2))=150$ to 180 degrees unless angles of $q_1$ and or $q_2$ exceeded 15 degrees. A q of 0 degrees will essentially create a straight vertical posterior surface 145 and would require a similar angle for surface 136. An angle of 180 would produce incremental forward protrusive movement of the mandible throughout the entire range of mandibular rotation (CR/CO to MMO) during mouth opening. The congruent relationship of surfaces 145 and 136 may create a posterior lean in the vertical axes of both surfaces such that their superior (cranial) edges may be posterior in relationship to their inferior (caudal) edges, thereby facilitating an anterior mandibular advancement as surface 145 slides down surface 136 with mouth opening (caudal mandibular advancement).

$q_2$ is primarily useful to control neutral mandibular protrusion during the initial 13 degrees of mandibular rotation (although protrusive flange can protrude the mandible when using MRD with motorized protrusive flange option) but can be adjusted to produce protrusive movement (the more $q_2$ is, the less the radius of mandibular incisor to TMJ, the less protrusion of the mandible during early rotation or mouth opening and the less $q_2$ is the more protrusion with each degree of mandibular rotation). On the other hand, $q_1$ is used to create the majority of the forward mandibular protrusion during the remainder of the mandibular rotation or mouth opening all the way to MMO (Maximum mouth opening). Resistance to mouth opening will also occur during this part of mandibular rotation due to the resistance from stretching the muscles of the TMJ as the mandible incrementally protrudes with every additional degree of mandibular rotation. Increasing $q_1$ will cause even more protrusion of mandible and thus also cause incremental resistance to mouth opening created by forward jaw movement. Essentially, if the desired outcome is to keep the mouth closed or barely open (CR/CO position), one could use only $q_1$ and remove $q_2$ altogether. This would require an arcuate or non-arcuate straight posterior surface 145 with $q_1$ of 0-15 degrees from the vertical axis starting at base 143 all the way up to 142 as shown in FIG. 6 and FIG. 7 with a corresponding surface 136 that is straight non-arcuate surface with a corresponding angle $90+q_1$ or a corresponding arcuate surface that leans back as shown in FIG. 6 or combination of arcuate and non-arcuate surfaces such as shown in FIG. 6. Under these circumstances, greater the $q_1$ greater the protrusion of the mandible with the least amount of mandibular rotation or mouth opening (mm of protrusion for each degree of mandibular rotation) and thus also ensure the highest resistance to mandibular rotation and mouth opening to match the needs of the user/patient. In an example, where the arcuately shaped side 145 is customized with $q_1$ and $q_2$ of 15 degrees each as well (total theta=180–30=150) for the sake of simplicity of driving home the point, a mandibular rotation or mouth opening of about 20 degrees will protrude the jaw anteriorly about 5 mm and a mandibular rotation of about 24 degrees will protrude the jaw anteriorly about 11 mm. Since the MPD (Maximum Protrusive Distance with range of 6-10 mm) typically has an absolute maximum of 10 mm, 11 mm is nearly impossible for most people and thus the mechanics of the device create the environment where the mouth will not open to MMO (Maximum mouth opening) of 24 degrees. However, as in some individuals, maximum advancement may be up to 15 mm, in those individuals the device would allow the freedom of further advancement.

The releasably attachable features of the flange 114' accommodates the interchangeability of protrusive flanges 114 of different shapes and sizes to provide the best fit for the user's mouth.

Turning now to FIGS. 18-21, some people in need of Continuous Open Airway Technology (COAT) may suffer from dysfunction or abnormalities of the temporo-mandibular joint (TMJ). These individuals may not have evidence of TMJ disease but may have mild restriction of the range of movement of the TMJ and mandibular advancement. As such, milder advancements of the mandible are needed for these individuals when using a mandibular repositioning device (MRD), such as the MRD 800 of FIG. 18. The MRD 800 has Dynamic Continuous Open Airway Technology (DCOAT) because the mandible will follow $Arc_2$ of FIG. 20 in which as the mandible drops to open the mouth, the mandible will move forward in small increments because of the shape of the protrusive flange 814 and the driver flange 832, thereby opening the airway. $Arc_2$ demonstrates that when the mandible opens in 5 degree increments relative to the TMJ, the forward point of the mandible changes as shown in Table 1 below.

TABLE 1

| Arc₂ Degrees of Travel corelated to Mandible position | |
| --- | --- |
| Degrees of Mouth Opening | Distance from the TMJ (centimeters) |
| 0 | 7⅛ |
| 5 | 8⅛ |
| 10 | 8⅜ |
| 15 | 8⁷⁄₁₆ |
| 20 | 8⁹⁄₁₆ |
| 25 | 8¾ |

In comparison, $Arc_1$ demonstrates the movement of commercially available COAT MRDs, which allow the mandible to open caudally, but allow the mandible to fall backward toward the throat; thus, obstructing the airway or adding to the obstruction.

Figure 18:
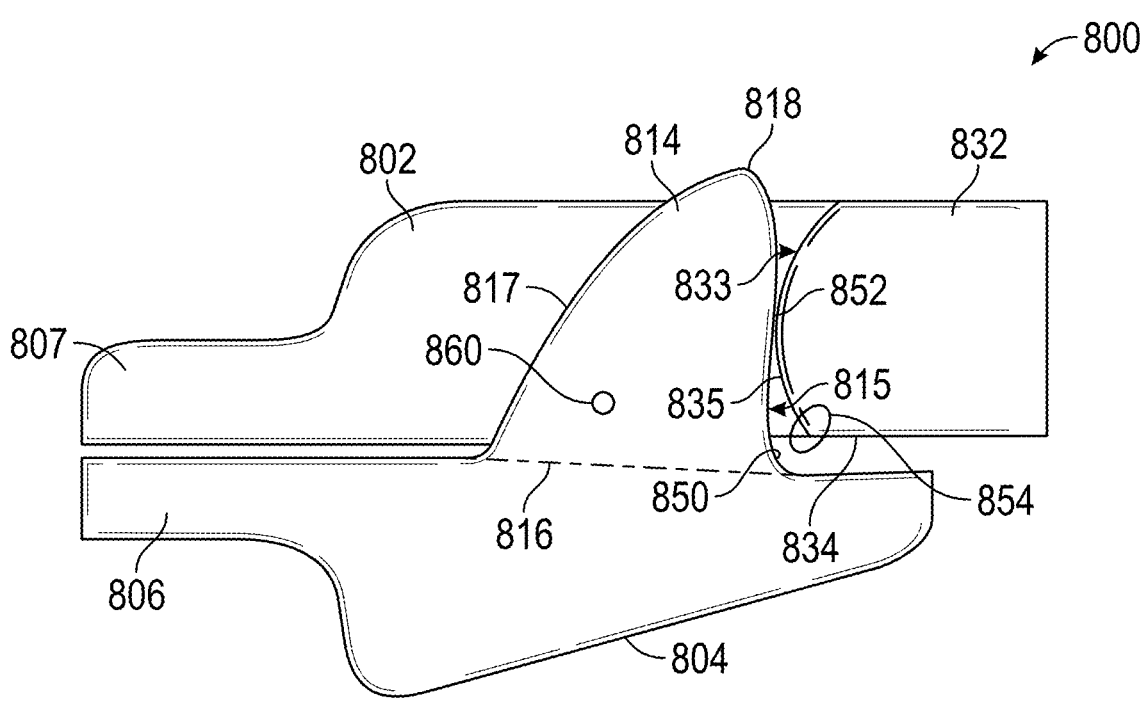
FIG. 18 is a side view of an embodiment of a mandibular repositioning device that provides Dynamic Continuous Open Airway Technology (DCOAT) to the user.
Figure 19:
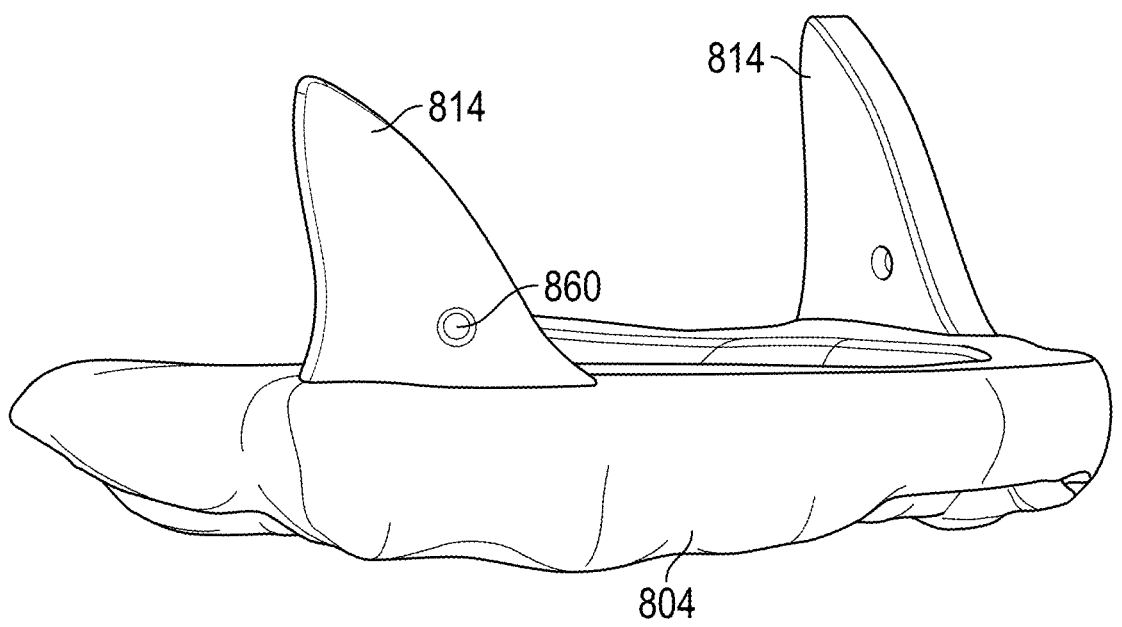
FIG. 19 is a side perspective view of the mandibular piece of the mandibular repositioning device of FIG. 18.
Figure 20:
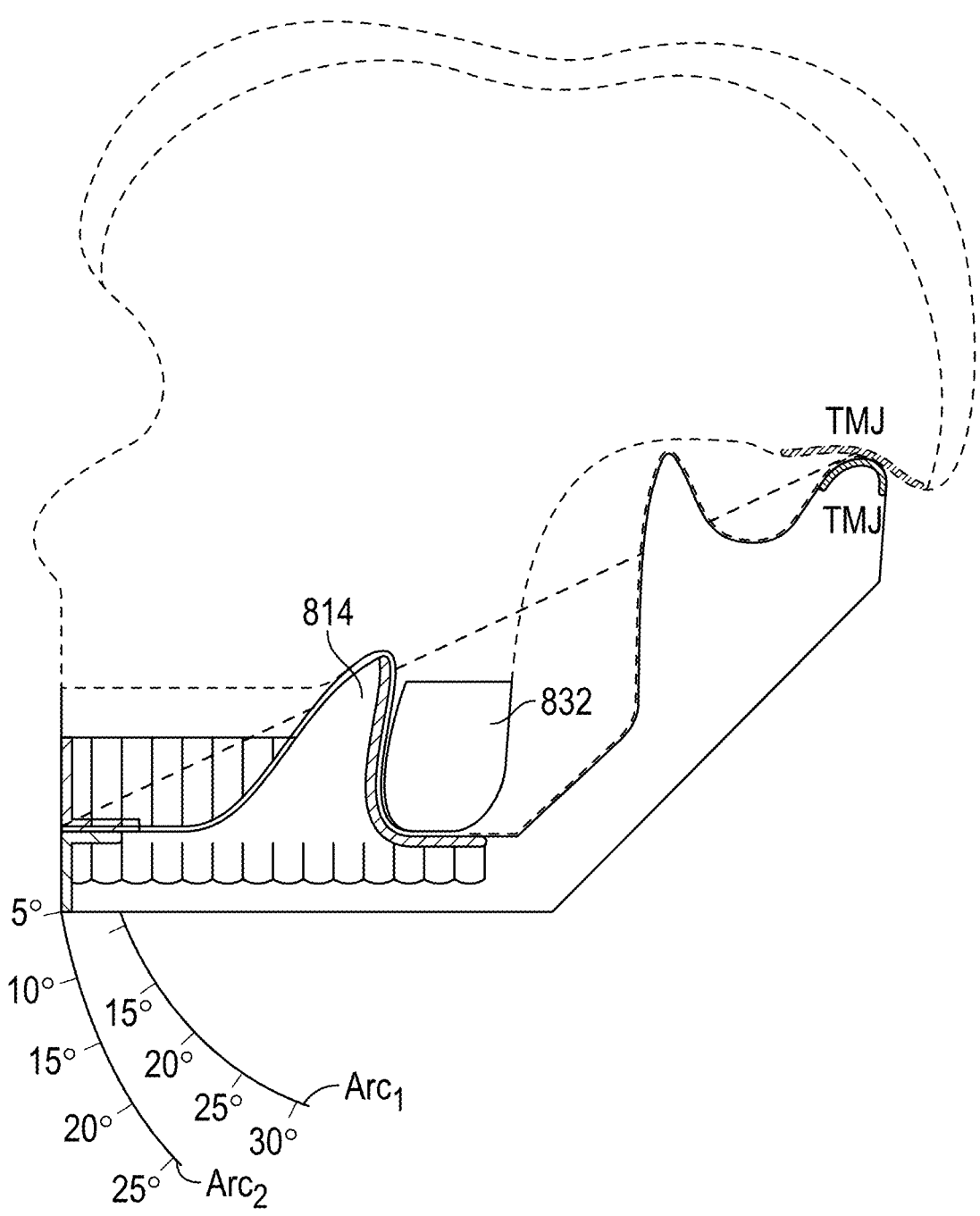
FIG. 20 is a model comparing the movement of the mandible of a user having the mandibular repositioning device of FIG. 18 against a commercially available mandibular repositioning device.
Figure 24:
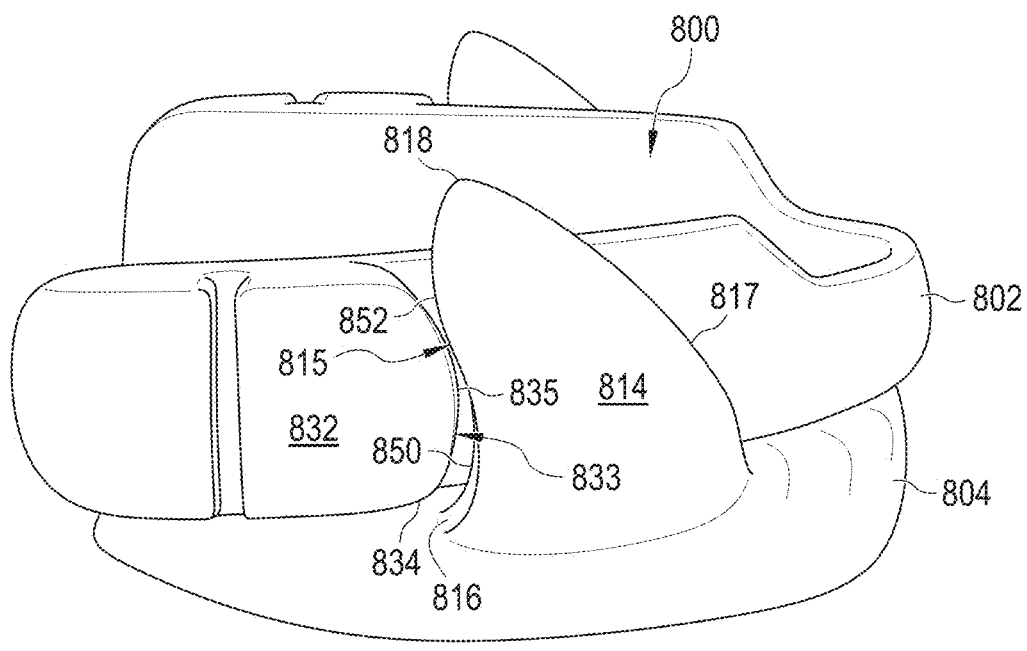
FIG. 24 is a photograph of a selected patient's mandibular repositioning device having the protrusive flange with the convex to concave curvature described herein against the convex curvature of the driver flange.

Turning now to FIGS. 18, 19 and 24, the various MRDs 800 have a concave-to-convex curvature moving from the base 816 to the most cranial point 818 of the posterior side 815 (or trailing edge) of the protrusive flange 814 of the mandibular piece 804 and a convex curvature 835 of the anterior side 833 (leading edge) of the driver flange 832. While FIG. 18 only shows the left side of the MRD 800, it is understood that the right side can be the same, and FIG. 19 shows a left side and has a mirror image for the right side. It is also understood that each side (left and right) of the mandibular piece and or the maxillary piece may, in fact, be just partial (2-5 teeth) coverings that may end with the anterior or leading edges 817 and 833 of the mandibular and maxillary pieces respectively or may extend further anteriorly to cover more teeth. The number of teeth covered may be different for the right and left side of each of these pieces as well. Thus, there may be up to 4 individual pieces, Two (mandibular and maxillary) for the right and two for the left. This will provide therapeutics for individuals who have a mouth that is too small (micrognathia) to fit an entire bulky device. For most user's the left side and the right side will be mirror images, but if the user has a difference in jaw and/or facial structure making one side different from the other, the device can be custom shaped to accommodate the differences. The protrusive flange 814 extends cranially from the mandibular piece 804 which has a teeth covering 806 for the lower teeth. The driver flange 832 protrudes laterally outward from the side of the maxillary piece 802 a distance sufficient to engage the posterior side 815 of the protrusive flange 814 with the anterior side 833 thereof The driver flange 832 has a base 834 positioned on the maxillary piece 802. i.e., the base of the driver flange does not extend caudally in an overlapping manner with the mandibular piece 804 in this embodiment. However, in another embodiment it may extend caudally as an extension of 835 in a way that it will be alongside (buccal side) of the mandibular piece 804, thus providing additional caudal anterior surface 833 for maintaining articulation with the posterior (trailing) surface 815 of the protrusive flange 814 during extremes of mouth opening such as yawning or otherwise. The maxillary piece 802 has a teeth covering 807 for the upper teeth. The protrusive flange 814 and the driver flange 832 are not shown in these embodiments to have the housings with the motor and mechanism for moving the flanges to provide the movements described herein for the other embodiment, but they are equally usable with such mechanisms and all the systems described herein.

The concave-to-convex curvature of the posterior side 815 of the protrusive flange 814 has a concave portion 850 most proximate the base of the protrusive flange. Cranially above the concave portion 850 is the convex section 852. The shape and positions of the concave and convex portions 850, 852 is described in more detail with reference to FIG. 21. The mathematical model in FIG. 21, was created using a scale of 1 cm=10 mm. Here, the dental horizontal axis ($A_H$) is represented by segment BC and runs horizontally between the mandibular teeth (crowns of the teeth) along the plane and the maxillary teeth (crowns) above the plane. Thus, the mandibular coverings part of the MRD lies below the horizontal axis while the maxillary coverings part lies above the horizontal axis. A vertical axis ($A_V$) is drawn perpendicular to the dental horizontal axis at a position passing between the protrusive flange 814 and the driver flange 832 in the at rest position shown in FIG. 21. The rest position is a position of the mandible at which there is no stress on the TMJ. This axis passes between the mating point $V_2$ of the protrusive flange 814 and the point $P_2$ of the driver flange 832. Point A represents the TMJ at rest and an axis parallel to the vertical axis ($A_V$) is drawn through point A, called the TMJ axis ($A_{TMJ}$). Point B is the point where the horizontal axis and the angle of the mandible intersect. The angle ABC created thus represents an angle adjacent to the angle of the ramus of the mandible. It is typically 40 degrees since the angle of the ramus of the mandible is 140 degrees on average. However, significant age, race and gender variations exist. We have assumed an angle of the ramus to be 100 degrees and the adjacent angle to be 80 degrees for sake of simplicity. The more obtuse the angle of the ramus, the more obtuse the tangent T and the greater the lean in the surface 835 of the protrusive flange 814 and surface 833 of the driver flange 832. Point C is the point where the TMJH vertical axis and the horizontal axis intersect. Point D is a mid-point of the length of the segment AC. Point E is a point along the TMJ axis that is at 2/3 of the height ($H_{DF}$) of the driver flange 832. Point F is the mirror of point D along the TMJ axis and Point G is the mirror of point A along the TMJ axis, i.e., a negative value equal to point D and Point A, respectively, below the horizontal dental axis. Point E1 is the mirror of point E on a vertical axis parallel to the TMJ axis but positioned at the front of the incisors ($A_I$). Average dimensions were used in FIG. 21, and it is therefore understood that these dimensions may vary from individual to individual based on natural variations of body size, jaw size, head size and variations created by abnormalities of the human body as well.

Figure 21:
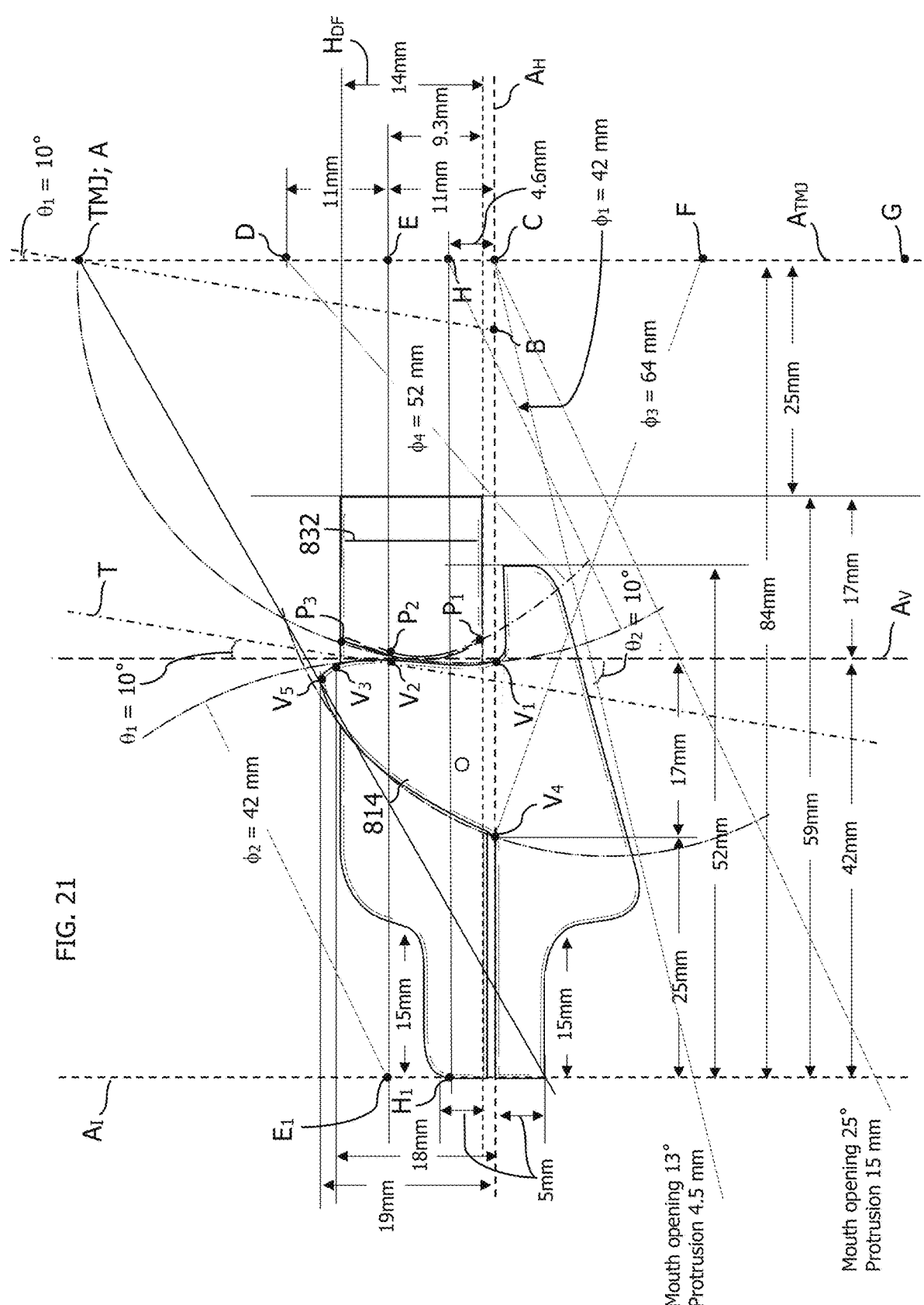
FIG. 21 is a mathematical model of how to position and determine the convex and concave curvatures of the protrusive flange and the driver flange of a mandibular reposition device.

The primary concept is to use a tangent (T) that is parallel to the lean of the Ramus of the mandible (represented by line segment AB) in relationship to the horizontal axis ($A_H$) that passes between the protrusive flange 814 and the driver flange 832 in the at rest position shown in FIG. 21. This creates an angle within the range of 10° to 50° with the vertical axis ($A_V$) on the maxillary side of the horizontal axis ($A_H$), which we call $q_1$. For the purpose of the following description and simplicity, 10° was selected for $q_1$ and $q_1$=$q_2$. However, $q_1$ can be any value within the 10° to 50° range. The tangent (T) defines the point $V_2$ of the protrusive flange 814 and the point $P_2$ of the driver flange 832 on the convex portions thereof, which are aligned in the at rest position. This is referred to as point $V_2P_2$ and is a point where three tangents meet to create the tangent (T). These are designed to meet at the same point although they do not always have to, especially, if a design for any individual requires a variance from this concept. Also, if the Ramus angle is different in each subject from what we have used for this discussion. T may change.

The five points labeled in FIG. 21 for the protrusive flange 814 are identified in this paragraph. Point $V_1$ is the lowest point on the trailing edge 815 of the protrusive flange 414 where it lands on the mandibular covering of the MRD. Point $V_2$ is where the tangent (T) coincides with point $P_2$. Point $V_3$ is the most cranial point of the trailing edge 815 of the protrusive flange 814. Point $V_4$ is the lowest point of the leading edge 817 of the protrusive flange 814. Point $V_5$ is the high point where $V_3$ reflects and meets the leading edge 817.

The three points labeled in FIG. 21 for the driver flange 832 are identified in this paragraph. Point $P_1$ is the lowest point of the leading edge 833 of the drive flange 832. $P_2$ is the point where tangent (T) coincides with point $V_2$. Point $P_3$ is the most cranial point of the leading edge 833.

At T=10○, the very front of the incisor part of the MRD to point C (the perpendicular dropped from A) appears to be 84 mm long. The midpoint of this segment is 42 mm (referred to herein as the midpoint length) from either end is at point $V_2$. This is an average distance and may vary on a case-by-case basis (as will all other measurements). About 4.6 mm above point C is a point that is one third of the height of segment AC measured from the horizontal dental plane, designated as point H. Using point H as a center point, a first arc $V_1$-$V_2P_2$ defining the curvature of the concave portion 850 of the trailing edge of protrusive flange 814 is drawn and a second arc $P_1$-$P_2$-$P_3$ (the entire leading edge of protrusive drive 832 is drawn using a radius 1 ($Ø_1$) of 42 mm (equal to the midpoint length). The 42 mm length for the radius could vary on a case-by-case basis.

The second arc $P_1$-$P_2$-$P_3$ defines almost the entire leading edge of the driver flange 832. The radius that will be used to draw the leading edge of the driver flange is about 0.2-0.5 mm shorter than the radius used to draw the trailing edge 815 of the protrusive flange 814 to allow a small play for the purpose of proper articulation. The leading edge 833 of the driver flange 832 has a back-cut portion 854 most proximate the point $P_1$. $P_1$ is described by a different radius, radius 4 ($Ø_4$) of 52 mm on average. The center point used to draw the arc for the back-cut portion 854 is point D such that segment EC=ED=11 mm.

Point E is created by drawing a horizontal line from the point $V_2P_2$ such that the angle created by $V_2P_2$–C–$V_1$=10○ thus allowing the point $V_2P_2$ to be the point where the tangent T=10○ from the vertical axis. Now extending the horizontal line that passes through the points $V_2P_2$ and E further to the left allows creation of a point $E_1$, such that segment $V_2P_2$–$E_1$=42 mm=segment $V_2P_2$–E. Extending the line H similarly will allow the creation of $H_1$. With $E_1$ as center point using the same radius $Ø_2$=42 mm another arch is drawn that starts at $V_2P_2$ and extends upwards to $V_3$, thus completing the remainder of the trailing edge of the protrusive flange 814. $H_1$ may similarly be used and any point between $E_1$ and $H_1$ may also be used for the same purpose depending on the amount of convexity required at the top of the protrusive flange 814 to create best mandibular advancement for each individual person.

Figure 22:
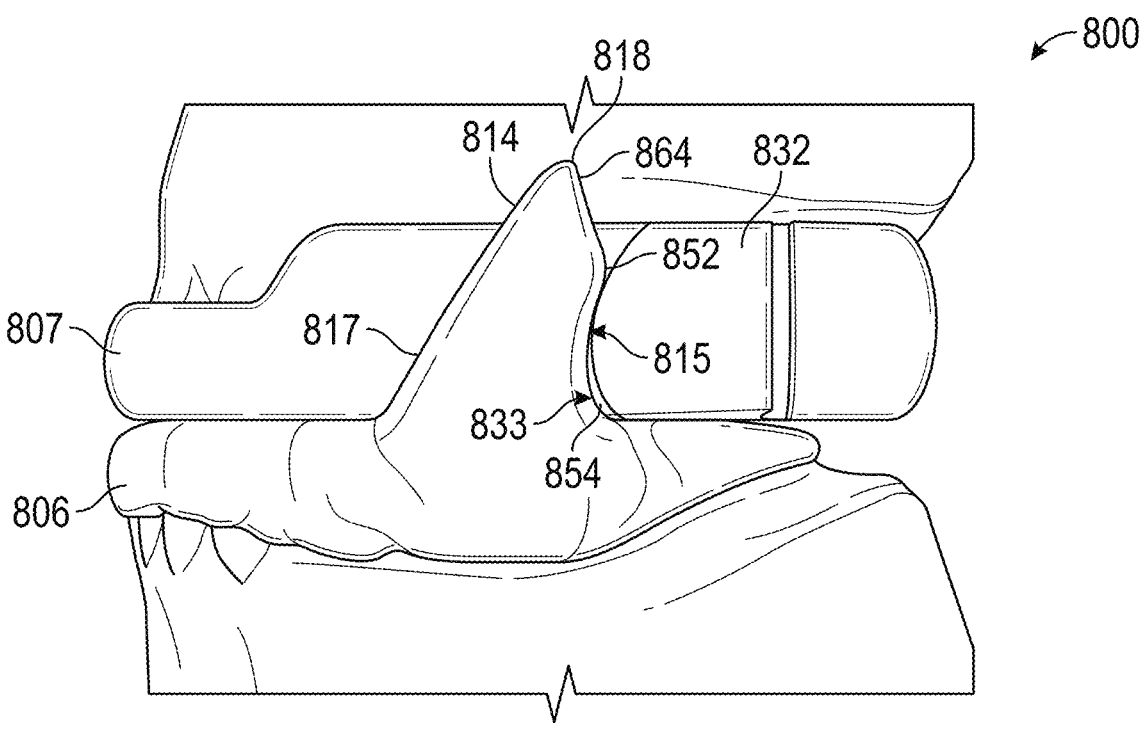
FIG. 22 is a side view of another embodiment of a mandibular repositioning device that provides Dynamic Continuous Open Airway Technology (DCOAT) to the user.
Figure 23:
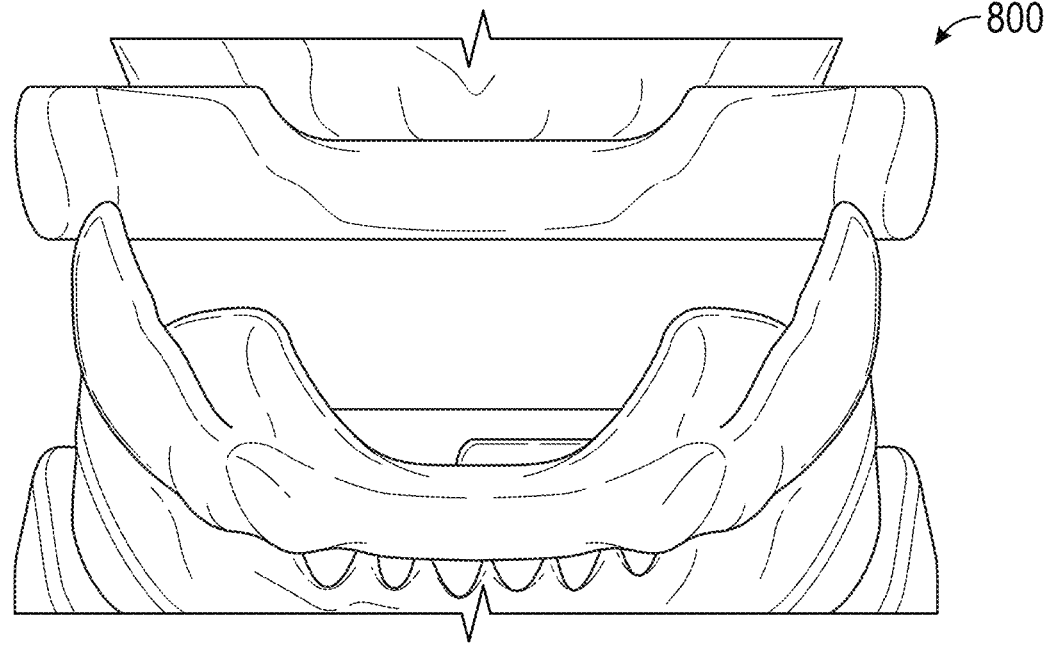
FIG. 23 is a front view of the device of FIG. 22 in a full-open mouth position.

To build the leading edge 817 of the protrusive flange 814, Point F was used as the center to draw arc $V_4$-$V_5$. This was then smoothed out at the top for a smooth transition to the trailing edge 815 and to avoid creating pointed edges. The convex curvature of the leading edge 817 is oriented with its curvature tilted toward the TMJ such that the most cranial point 818 (point $V_5$) is more proximate point $V_2$ than point $V_4$. However, turning now to FIGS. 22 and 23, an alternate embodiment 800' for the MRD is shown in which the leading edge 817 of the protrusive flange 814 can be more linear, yet still oriented tilted with the most cranial point 818 pointed toward the TMJ. Additionally, FIG. 22 has a back-cut portion 864 to the convex portion 852 most proximate the most cranial point 818, back-cut toward the most cranial point 818. FIG. 23 is a front view of the MRD 800'of FIG. 22 in a full-open mouth position with the back-cut portion 864 of the protrusive flange 814 seated against the back-cup portion 854 of the driver flange 832.

A user in need of an open airway, most often during sleep, but not limited thereto, inserts the maxillary and mandibular device of any of the embodiments disclosed herein into their mouth and goes about with their activity or goes to sleep. With respect to the shape of the flanges in FIGS. 18-29, when the user moves the mandible downward, such as normal relaxation during sleep, the protrusive flange 814 of the mandibular piece 804 moves along the convex curvature of the driver flange 832, which will move the mandible forward, see the increments of movement set forth in Table 1 above, and naturally opens the airway. Some users are capable of opening their mouths wider than others, and if, their mouth can open to a distance that is greater than the height of the protrusive flange 814 on the mandibular piece 804, there is a chance that the protrusive flange 814 could become disengaged from the driver flange 832 of the maxillary piece 802. To maintain contact between the mandibular piece 904 and maxillary piece 802 (prevent disengagement) during anterior-posterior repositioning and cranial-caudal repositioning, especially when both types of repositioning occur simultaneously, a plateau 870 of a preselected height ($H_P$) has been added to the mandibular repositioning devices of FIGS. 25-29 between the base 816 of the protrusive flange 814 and the floor 872 of the tooth covering 806 of the mandibular piece. The preselected height ($H_P$) of the plateau 870 prevents disconnect between each protrusive flange 814 and its respective driver flange 832 relative to a fully open mouth measurement between incisors of the user by having a height that compensates for the difference between the fully open mount measurement and the height of the protrusive flange ($H_{PF}$).

Figure 25:
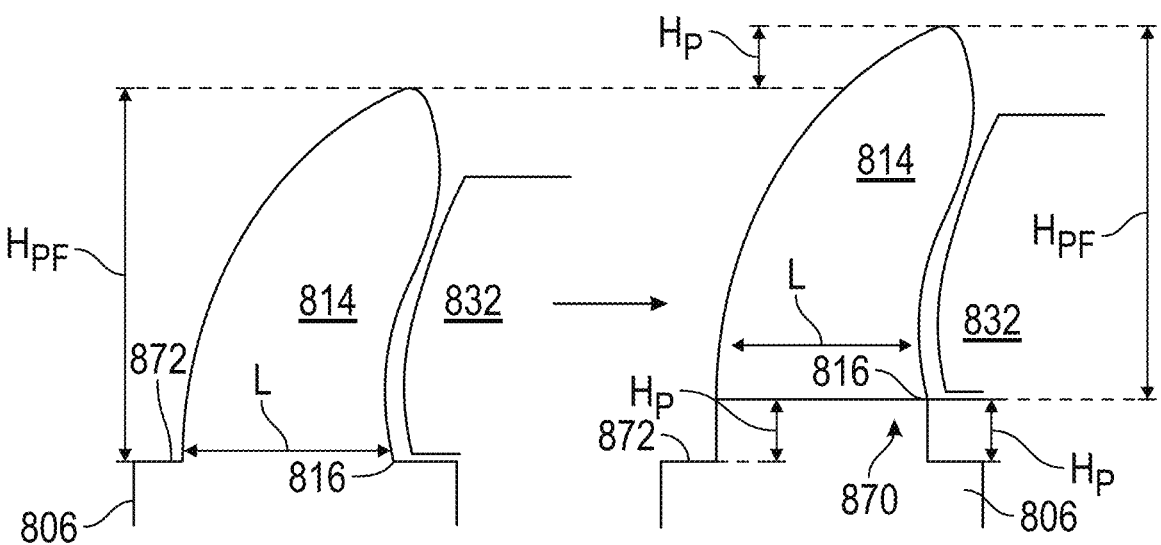
FIG. 25 is a comparison of a sketch representative of the mandibular repositioning device of FIG. 24 (left) to a sketch (right) thereof with a mandibular plateau added to the base of the protrusive flange.
Figure 26:
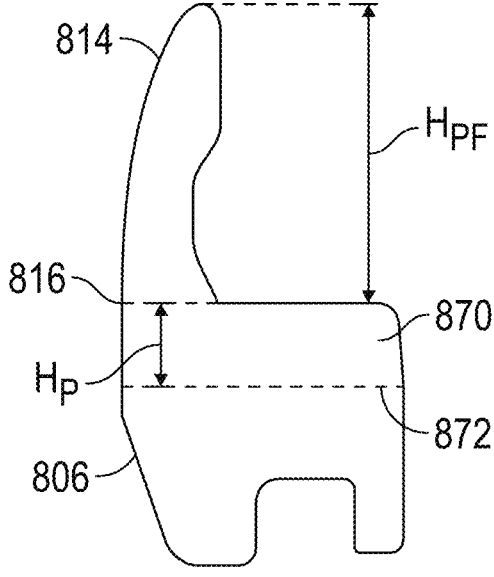
FIG. 26 is a rear view sketch of mandibular piece with the mandibular plateau of FIG. 25.

Referring to FIGS. 25-29, the preselected height ($H_P$) for these examples was selected to be 1.06 mm because the user was capable of opening their mount 20.06 mm and the flange height ($H_{PF}$) was 19 mm. The flange height is typically less than 20 mm and is often in the range of 17 mm to 19 mm for the average adult. In another example, if a user has a fully open mouth measurement of 36 mm and the protrusive flange height is 19 mm, the preselected height for the plateau is 17 mm. As best seen in FIGS. 25 and 26, the plateau 870 extends across the full width of the tooth covering 806 and has a length (L) equivalent to the length of the base of the protrusive flange 814. Here, the plateau 870 has a uniform preselected height ($H_P$) along the length (L) thereof.

Turning now to FIG. 27, the plateau 870' is wedge-shaped, thereby having a first height ($H_1$) at an anterior base 817 of the protrusive flange 814 that is greater than a second height ($H_2$) at the posterior base 816 of the protrusive flange. The plateau 870'causes the concave-convex curvature of the protrusive flange 814 to be inclined relative to the mandibular piece 804, thus the driver flange 832 is also inclined equivalently to the plateau 870' to maintain the engaged convex to convex mating curvature thereof. This creates a gap 872 between the driver flange 832 and the mandibular piece 804.

FIGS. 28 and 29 are examples of different embodiments for filling this gap with either an extension of the plateau 870 or of the driver flange 832, respectively. In FIG. 28, the plateau 870' has an extension 874 that extends posteriorly to a posterior terminus surface 876 of the tooth covering 806 of the mandibular piece 804. The extension 874 continues the wedge shape of the plateau 870' and terminates with a third height ($H_3$) that is less than the first height ($H_1$) and the second height ($H_2$). In FIG. 29, the plateau terminates posteriorly at the posterior base 816 of the protrusive flange 814 and the driver flange 832 has an extension 878 that extends caudally with its anterior side extending the convex curvature thereof past the posterior base 816 of the protrusive flange 814 into a gap 872 (FIG. 27). The driver flange 832 has a base that is seated on the mandibular piece 804 as a result of the presence of the extension 878. The extension 874 and 878 provide the benefit of added space for the housing in which the electrical components, motors, power sources, etc. that are described herein are enclosed. In another embodiment, extension 878 may extend caudally adjacent to the mandibular piece only thus allowing an extension for continued articulation between surfaces 833 and 815 with extremes of mouth opening.

Turning now to FIG. 30, the plateau provides significant benefits to the combined effect of the protrusive flange 814 and the driver flange 832 (anterior-posterior repositioning and cranial-caudal repositioning). For example, looking at columns 3 and 4 of FIG. 30, if a user actively opens their mouth 8.28 mm (5 degrees) in the absences of a plateau, the AVMLRD-aided anterior movement of the mandible is 6.25 mm for the average adult. With any of the mandibular repositioning devices of FIG. 25-29, which have a protrusive flange height of 19 mm and a plateau of 1.06 mm, and an anterior movement selected to be 5 mm at the rest position based on the curvature profiles of the protrusive flange and the driver flange, the same amount of anterior movement is achieved by opening the user's mouth just 1 degree. The anterior movement for the at rest position is typically set to be in the range of 1 mm to 6 mm (see the header of FIG. 30 at the far left). Without the plateau, the mandibular repositioning device has a limited range for the cranial-caudal repositioning as determined by the height of the protrusive flange, in other words, the addition of a plateau extends this range.

Still referring to FIG. 30, it has been determined that a combined effect within the 1 mm to 6 mm anterior movement at the rest position of: (i) Area 0:2.25 mm to 7.4 mm is useful for treating primary snoring disorder and mild OSA; (ii) Area 1 and Area 2:7.5 mm to 10.9 mm is useful to treat mild, moderate, and severe OSA with lowest saturation range of 81% to 90%; (ii) Area 3:11 mm to 13.9 mm is useful to treat moderate and severe OSA with lowest saturation range of 79% to 81%; (iv) Area 4:14 mm to 17.9 mm is useful to treat severe OSA with lowest saturation range of 76% to 79%; and (v) Area 5:18 mm to 28 mm is useful to treat severe OSA with lowest saturation ranges below 76%. Further, the most useful is Area 1: a 5 mm to 6 mm anterior advancement in the rest position (central occlusion or centric relationship) with a 2 to 3 mm degree mouth opening by the user will treat mild to moderate OSA. Using the Area 1 configuration and the flange dimensions described for FIG. 25, the improvements expected for various parameters for a user were theoretically calculated and are listed in the table in FIG. 31.

Also, theoretical oxygen saturation improvements were calculated for the combined effect from 8.5 mm to 29 mm (from Area 1 to Area 5 of FIG. 30) and are presented in Table 2 below and further gains are expected with TAVMLR up to 32 mm or more.

17

TABLE 2

| TOTAL AVMLR (mm) | OXYGEN SAT. IMPROVEMENT (%) |
|---|---|
| 8.5 | 6.92 |
| 10 | 8.1 |
| 11 | 9.0 |
| 12 | 9.8 |
| 13 | 10.6 |
| 14 | 11.4 |
| 15 | 12.2 |
| 16 | 13.0 |
| 17 | 13.8 |
| 18 | 14.7 |
| 19 | 15.5 |
| 20 | 16.3 |
| 21 | 17.1 |
| 22 | 17.9 |
| 23 | 18.7 |
| 24 | 19.5 |
| 25 | 20.4 |
| 26 | 21.2 |
| 27 | 22.0 |
| 28 | 22.8 |
| 29 | 23.6 |

A sleep study of a user was conducted for a user having a mouth opening calculation: 23 mm mouth opening or 14 degrees opening with 0 mm Anterior Advancement, 23 mm Vertical Advancement, 17.5 Total AVMLR Advancement. A 17.5 total AVMLR combined effect is predicted to provide a 13.8% increase in oxygen saturation based on Table 2 above. The sleep study data is presented in FIG. 32. The AVMLR provided the user a 13.6% increase in oxygen saturation, which is in direct correlation to the theoretical improvement. Moreover, the data from the sleep study with the AVMLRD is shown in FIG. 32 in contrast to data pre-treatment and for treatment with a BiPAP machine. The user wearing the AVMLR experienced overall better sleep than using the BiPAP machine, in particular, improvement in every category of the sleep study, including a 50% decrease in respiratory disturbance and a 66.6% increase in REM sleep as compared to the BiPAP effects. The AVMLRD outperformed the BiPAP treatment with superior effect, including a greater than 10% increase in 5 out of seven categories and a greater than 20% increase in four of the seven categories.

In any and all of the embodiments disclosed herein, the protrusive flange 814 may be molded as an integral portion of the mandibular piece 804 but is preferably a removably attachable flange. When the flange is removable, it may include a hole or depression 860 as shown in FIG. 18 to receive a tool to activate a release of the fastener holding the removable attachable flange in place on the mandibular piece 804. Likewise, the drive flange 832 may be molded as an integral portion of the maxillary piece 802 or it may be removable attachable thereto. The fasteners for holding flanges to their respective pieces 802, 804 can be any specifically described herein, and commercially available, or any hereinafter developed.

Figure 33:
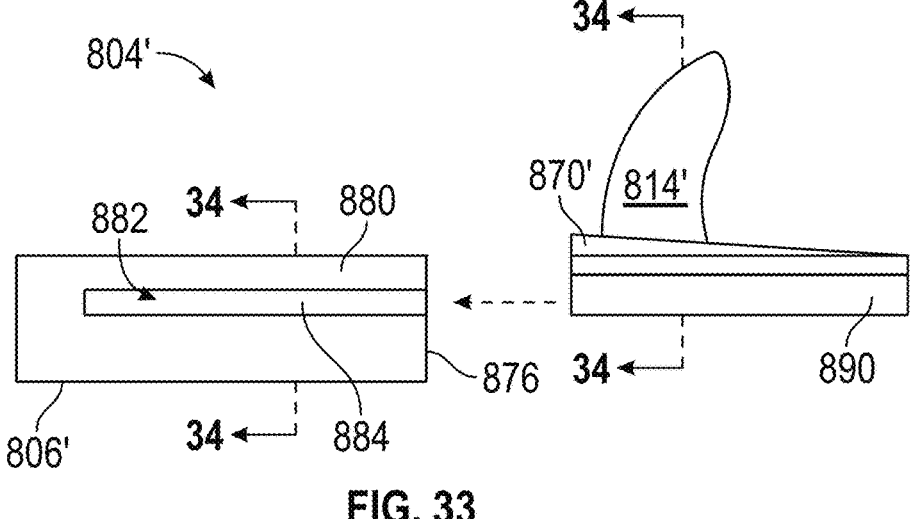
FIG. 33 is a side plan view of one embodiment of a mandibular piece with a removably replaceable protrusive flange in a pre-assembly position.
Figure 34:
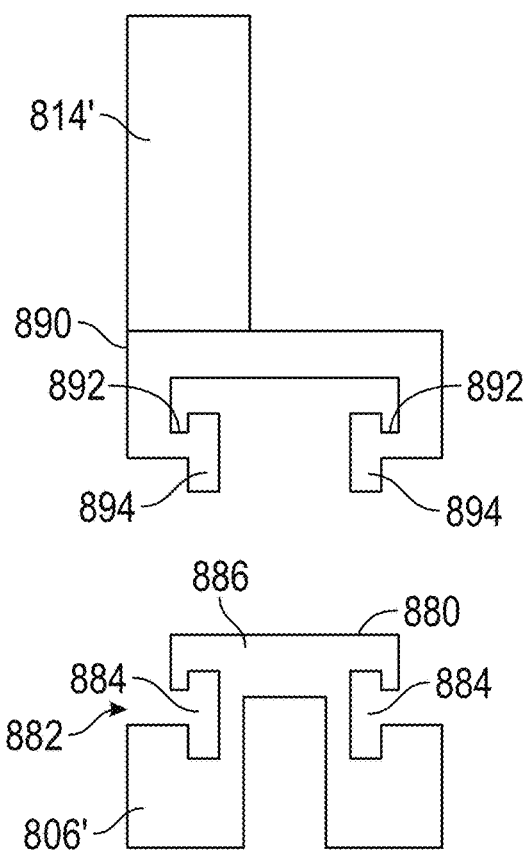
FIG. 34 is a rear view of the embodiment of FIG. 33 at the cross-section 34-34.

Turning now to FIGS. 33-34, the protrusive flange 814' can be removably replaceably attached to form the mandibular piece 804' by sliding into the tooth covering 806' from a posterior terminus surface 876 and engagingly saddles the dental crown 880 against cranial movement. The dental crown 880 defines a keyway 882 having opposed elongate grooves 884, one each open in the buccal and lingual directions, and defining a tongue 886 above the opposed elongate grooves 884. The protrusive flange 814' has a keyed slider 890 configured to slidingly mate to the keyway 882 of the dental crown 880. As such, the keyed slider 890 has an overall general U-shape with inwardly directed elongate, opposing arms 892 each terminating with elongate cranial to caudally oriented flanges 894.

Figure 35:
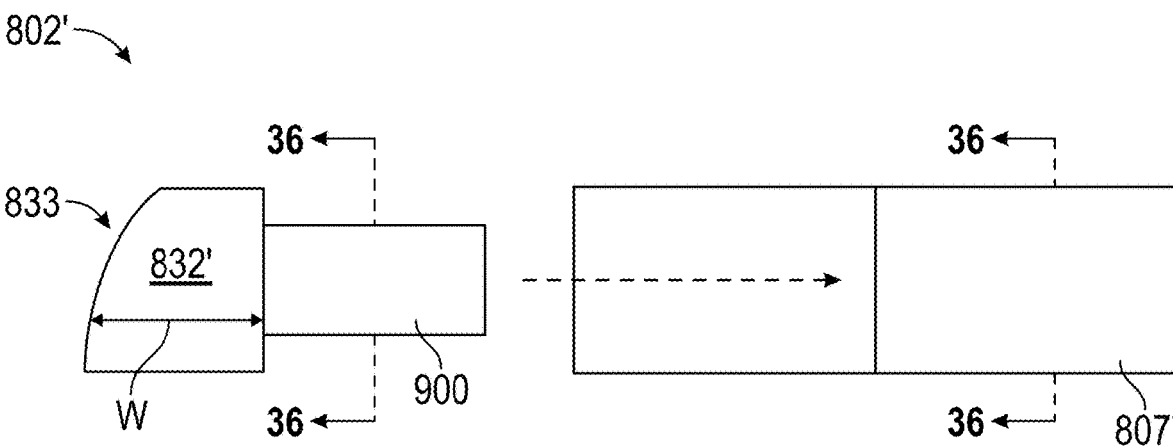
FIG. 35 is a side plan view of one embodiment of a maxillary piece with a removably replaceable driver flange in a pre-assembly position.
Figure 36:
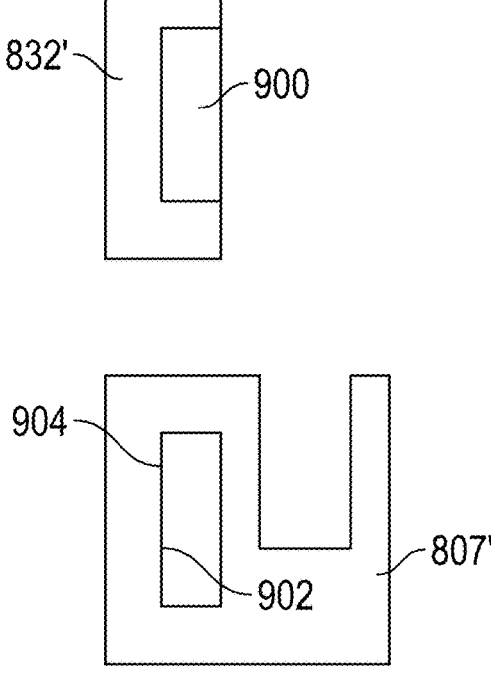
FIG. 36 is a rear view of the embodiment of FIG. 35 at the cross-section 36-36.

Turning now to FIGS. 35-36, each driver flange 832' is removably replaceably attached to the teeth covering 807' of the maxillary piece 802' by sliding a posteriorly extending post 900 into a slot 902 having an anterior opening 904. The maxillary piece 802' has a slot 902 buccally juxtaposed to a respective one of each of the left and right backmost teeth mold thereof. The orientation of the sliding attachment of each of the protrusive flange and the driver flange prevents the protrusive flange from sliding out of the mandibular pieces when the posterior side of the protrusive flange moves along the convex curvature of the driver flange as the user opens their mouth and likewise pushes the driver flange into the slot of the maxillary piece as well.

One of the benefits of the removability of the protrusive flange and/or the driver flange is the ability to offer a kit having one or both of the maxillary piece and the mandibular piece having a removable flange and a plurality of said flanges to accomplish different amounts of anterior-posterior repositioning and cranial-caudal repositioning. In one embodiment, the kit has both a maxillary piece and a mandibular piece that have removably replaceable flanges, driver and protrusive flanges, respectively and a plurality of each flange in sets of protrusive and driver flanges to achieve different amounts of anterior-posterior repositioning and cranial-caudal repositioning.

In one embodiment, a plurality of left and right protrusive flange pairs are provided with the kit and at least one of the plurality of left and right protrusive flange pairs has a plateau of a preselected height between a base of each protrusive flange and a keyed slider extending caudally from the protrusive flange. The preselected height of the plateau prevents disconnect between each protrusive flange and its respective driver flange relative to a fully open mouth measurement between incisors of the user. Each protrusive flange engagingly saddles either a left backmost teeth mold or a right backmost teeth mold of the mandibular piece as part of its respective keyways described above against cranial movement. The plurality of left and right protrusive flange pairs differ in protrusive flange height ($H_{PF}$), angle, posterior side distance from the posterior terminus surface 876, and combinations thereof to provide differing effects to the user.

The kit can also include a plurality of left and right protrusive flange pairs having a post slidingly receivable in a slot in the maxillary piece. The plurality of left and right driver flange pairs differ in width, convex curvature of the anterior side, posterior lean, and combinations thereof to provide differing effects to the user. The width (W), labeled in FIG. 35, is measured at the apex of the convex curvature and is typically in a range of 5 mm to 11 mm (thereby allowing at least 1 mm width at the superior end of the flange). When this is 5 mm, the mandibular piece will be in CO/CR position i.e., 0 mm advanced position. When this is 11 mm, the mandibular piece is advanced by 6 mm. The 5 mm to 11 mm thickness also leaves sufficient width in the slot 902 of the maxillary piece for the post 900 to slide securely therein. The width is tailorable to provide a preselected amount of anterior advancement of the mandible of the user while in the at rest position.

Figure 37:
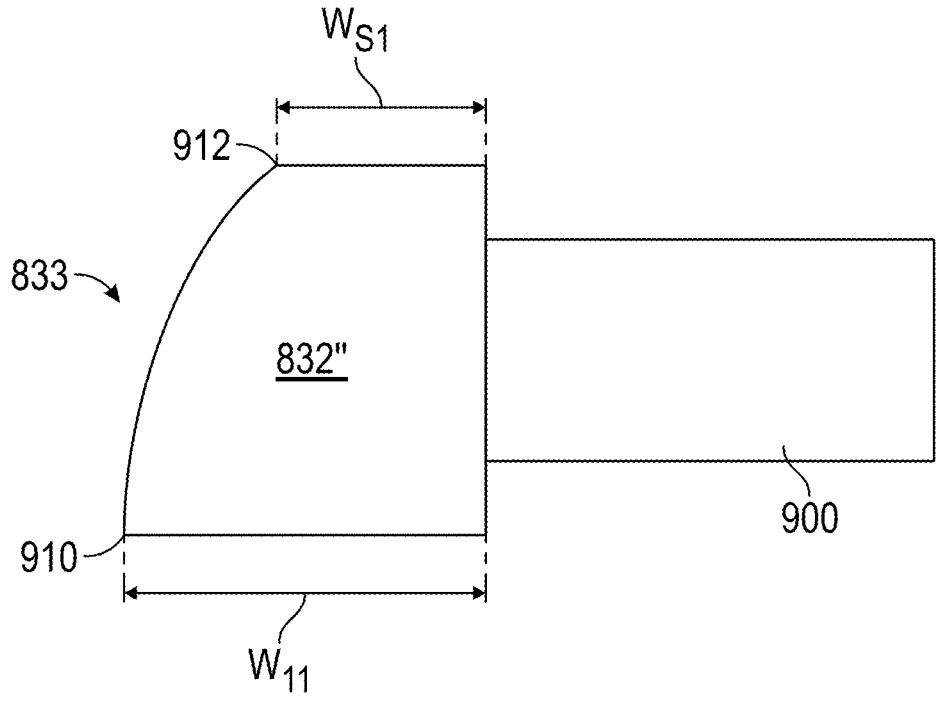
FIG. 37 is a side plan view of a second embodiment for the removable driver flange.
Figure 38:
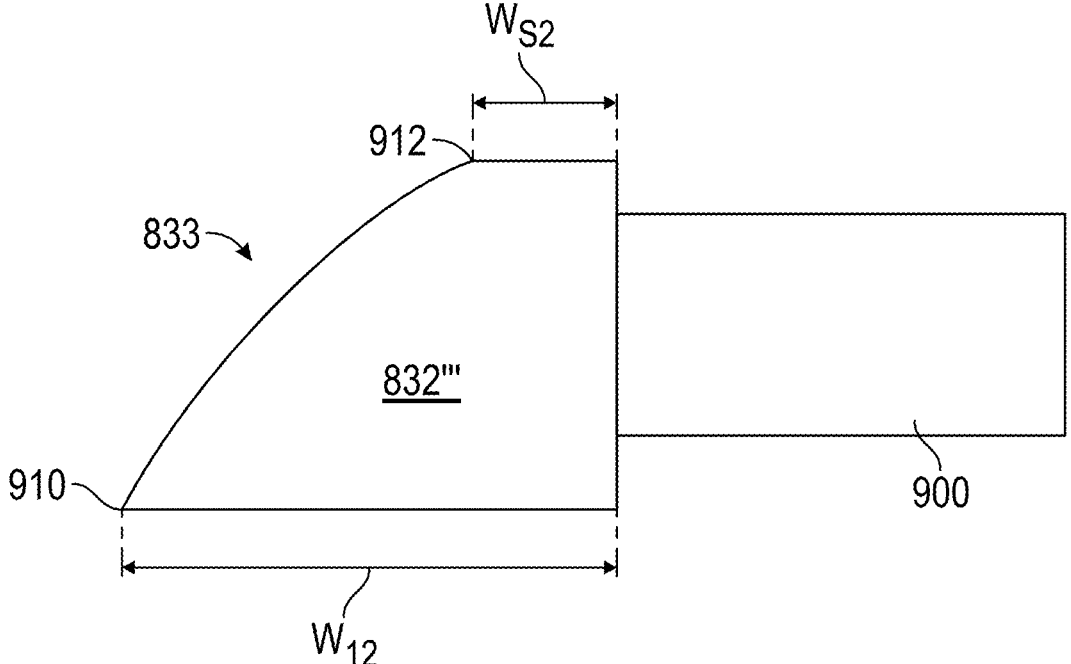
FIG. 38 is a side plan view of a third embodiment for the removable driver flange.

Differing posterior lean is shown in comparing the shape of the anterior side 833 of the driver flange 832', 832'', 832''' of FIGS. 35, 37, and 38. FIG. 38 has an anterior side 833 with the most posterior lean. Here, the superior width ($W_{S2}$) is much smaller than the inferior width ($W_{I2}$) of the driver flange 833, thereby tilting the convex curvature of the anterior side 833 posteriorly as you move from the inferior base 910 to the superior cranial point 912 thereof. In contrast, the driver flange of FIG. 37 has the smallest (least) posterior lean. Here, the difference between the inferior width ($W_{I1}$) and the superior width ($W_{S1}$) is the smallest. The convex curvature can be increased, decrease, or adjusted with a preselected amount of posterior lean. Such changes to the convex curvature are selected to enable the mandible of the user to advance incrementally more with mouth opening. Less superior lean advances the mandible in the anterior direction less with each degree of mouth opening. In contrast, more superior lean advances the mandible in the anterior direction more with each degree of mouth opening. For example, the posterior lean in FIG. 37 may provide only a 1 mm anterior advancement with each degree of mouth opening, and the posterior lean in FIG. 38 may provide a 3 mm anterior advancement with each degree of mouth opening. The flange on the mandibular piece will also lean more or lean less to provide the best range of anterior and vertical mandibular advancement.

In one embodiment, one pair of the plurality of left and right protrusive flanges provides the user with a 6 mm anterior advancement of the mandible. This embodiment can also have a pair of the plurality of left and right driver flanges that provides the user with a 6 mm anterior advancement of the mandible, thereby providing a 12 mm net anterior advancement for the mandible in the rest position. As noted above, the pairs of flanges are typically mirror images of one another unless the user has a jaw or face asymmetry.

If the end user's activity would require, the removably replaceable protrusive flanges and driver flanges can include a fastener. The fastener can be a clasp, screw, snap fit, etc.

Figure 39:
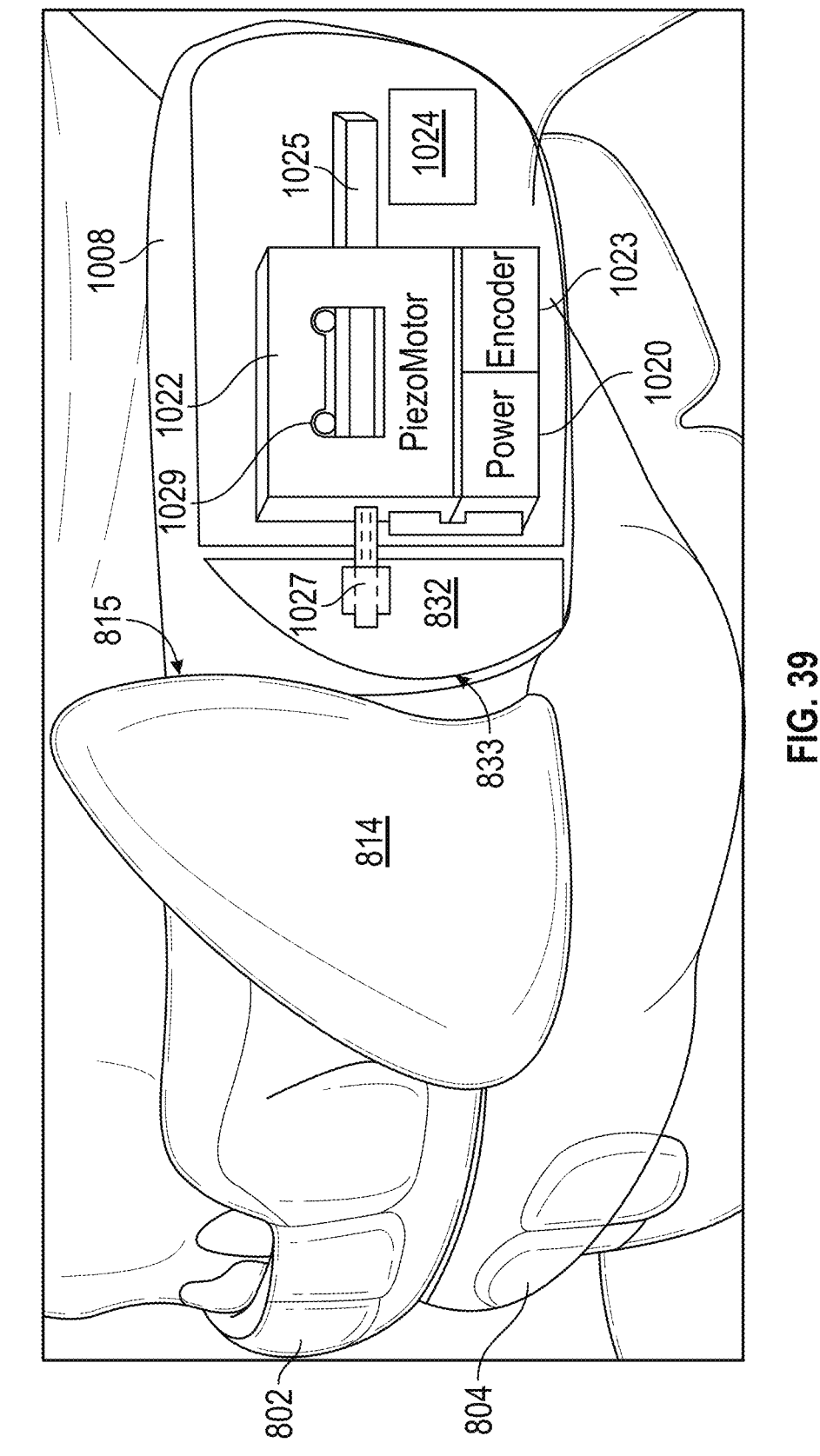
FIG. 39 is a left, side view of a first embodiment of the mandibular repositioning device having integrated anterior-posterior adjustment and cranial-caudal adjustment built into the maxillary piece.

Turning now to FIG. 39, an alternate embodiment to those in FIGS. 1-4 is shown that has both the anterior-posterior movement and the cranial-caudal movement of the mandibular repositioning device integrated into the maxillary piece 802 for control of the driver flange 832. The maxillary piece 804, on its buccal aspect, has a housing 1008 at each of the left and right molar portion, which each enclose, in a fluid-tight manner, a power source 1020 electrically connected to a piezo motor 1022 and to an encoder 1023 that controls the movement of a rod 1025 operatively connected to the piezo motor 1022 and to the driver flange 832. The power source 1020 is also electrically connected to a circuit board (microprocessor) 1024 that is in operative communication with the encoder and any of the sensor, stimulators, drug dispensers, etc. disclosed herein that are included in the maxillary piece. The rod 1025 encloses a set of robotic arms that move synchronously or opposite to each other (gliding together or sliding away from each other) driven mechanically, electrically, or electromagnetically by the piezo motor or electric and magnetic fields (EMF) generating coil that provides magnetic forces or mechanical forces to glide or slide the rod/arms. These are electric and magnetic fields (EMF) generated within using an EMF powered synchromesh and induction motor. Synchronous motors have an advantage of constant speed, steady load and operate with low voltage current or micro-voltage current. Absence of gearing gives them a smooth and quiet functionality that will be beneficial for this application. Induction motors have sustained torque and variable speed. Synchronous motors have pull up torque. Combination of these two facilitates movements starting after long periods of quiescence, continuous push-pull movements, and reversal of motor rotation. This creates the ideal combination that provides anterior and posterior, push-pull movements of the driver flange 832. A first arm drives the driver flange 832 anteriorly and posteriorly. A second arm drives the lean of the anterior surface of the driver flange. The distal end 1027 of the rod 1025 houses the two arm terminations into ball-socket terminals or other hinged terminals in the housing within driver flange 832. When both, maxillary and mandibular pieces are in place and a bite or clench is carried out or the flanges come in contact with each other or any form of trigger that will provide sensory activation of the device, such as activation through a handheld device, controller station or simply inserting all the relevant pieces into the mouth. Then the piezo motor activates (this provides the system with a signal that the device is installed in the oral cavity for use) and all components including the AVMLRD, handheld device, controller station, cloud-based repository of memory are activated. The system goes through a formal boot process and checks all components are functioning normally and live to go. The user gets a communication and then confirms active status of the system and finalizes activation. In the event that the user is incapacitated, next-of-kin followed by physician or EMS are notified in real time. It then moves the driver flange anteriorly using the first arm to bring the protrusive flange 814 to the prescribed position such as a Centric Occlusion or 1 mm to 6 mm advancement. In doing so, it clears room between the housing 1008 and the driver flange 832 that allows the second arm to perform prescribed posterior lean of driver flange 832. Both, the first arm and the second arm are actively moving back and forth (+ and − movements in their respective axes) during active operation and all movements are actively powered. The lean function allows the anterior leading edge of the driver flange 832 to maintain the prescribed lean and adjust the lean dynamically during use on an as needed basis.

The piezo motor 1022 in each housing 1008 is configured for three specific functions of the rod and the two arms within the rod. Cranial to caudal adjustments of the rod 1025 (i.e., first and second arms) through rotation around a central axis, anterior-posterior gliding of the rod (performed by first arm) and preferential sliding of the second arm perform the lean function. Alternately, the cranial to caudal adjustments is performed through movement of the entire piezo motor within the housing 1022 using a robotic armature, which is accomplished by the wheels 1029 positioned above the rod 1025. Caudal movement of the driver flange 832 enables the drive flange 832 to accompany the caudal movement of the protrusive flange 814 as the user opens their mouth and the reverse when closing their mouth. Alternately, driver flange 832 actively pushes the mandibular piece 804 caudally as the first arm anteriorly advances and the second arm leans posteriorly creating a positive pressure at the caudal anterior leading edge of the driver flange 832, nudging the trailing edge of the protrusive flange 814 and its caudal root to move caudally: thus, actively opening the user's mouth. This keeps the two flanges 814, 832 in constant contact with one another, thereby reducing the likelihood or possibility of changes of a disconnect therebetween. The anterior-posterior movement and cranial-caudal movement directed by the piezo motor can occur simultaneously, individually, and/or sequentially.

The circuit board 1024 has a microprocessor comprising a quantum microchiplet and/or a photonic integrated circuit and nontransitory memory. While FIG. 39 shows the left housing 1008 with circuitry board 1024, the right housing will likewise include the circuit board and other components. The left and right circuit boards may have symmetric functions or shared functionality, communicating with each other continuously, and external controller, and/or other smart devices or through a two-way transmitter housed inside the protrusive flange 814. The microprocessor has stored in the nontransitory memory a first algorithm controlling the cranial-caudal movement of the piezo-electric motor relative to data receivable from one or more sensors. The sensors are typically in the oral cavity but are not limited thereto. The sensors can measure airway cross-sectional area, airflow volume, airflow velocity and pressure, airflow resistance, systolic and diastolic blood pressure, electrical activity of the heart, oxygen level, heart rate, and combinations thereof. The systolic and diastolic blood pressure and electrical activity of the heart may be measured by capacitive micro-machined ultrasound. Position sensors can be included that measure a first distance for cranial-caudal movement and a second distance for anterior-posterior movement of the driver flange.

The microprocessor has stored therein a second algorithm for anterior-posterior movement and lean functionality as described above. In one embodiment, the anterior-posterior movement is corelated to movement desirable when the user is under the influence of medication, sedation, anesthesia, or alcohol. The microprocessor has artificial intelligence to learn from the collected data form the sensors when to make anterior-posterior and/or cranial-caudal adjustments to the driver flange and can do so before a measured parameter moves out of a set range of values so as to maintain those values as close to the mean as possible and within a certain set of 1 to 6 standard deviations from the mean. In one embodiment, increasing airflow resistance, decreasing airflow volume, and decreasing cross-sectional area of the airway (SMCA) will immediately trigger the prescribed caudal and anterior movements through the first arm and required lean through the second arm thus moving the mandible and the tongue anteriorly and caudally at an incremental level desired with continuous feedback through the sensors. As airflow resistance drops, airflow volume increases and SMCA begins to increase, reverse movements of the first and second arms would result in raising the mandible cranially and simultaneously or sequentially retracting the mandible posteriorly.

Figure 40:
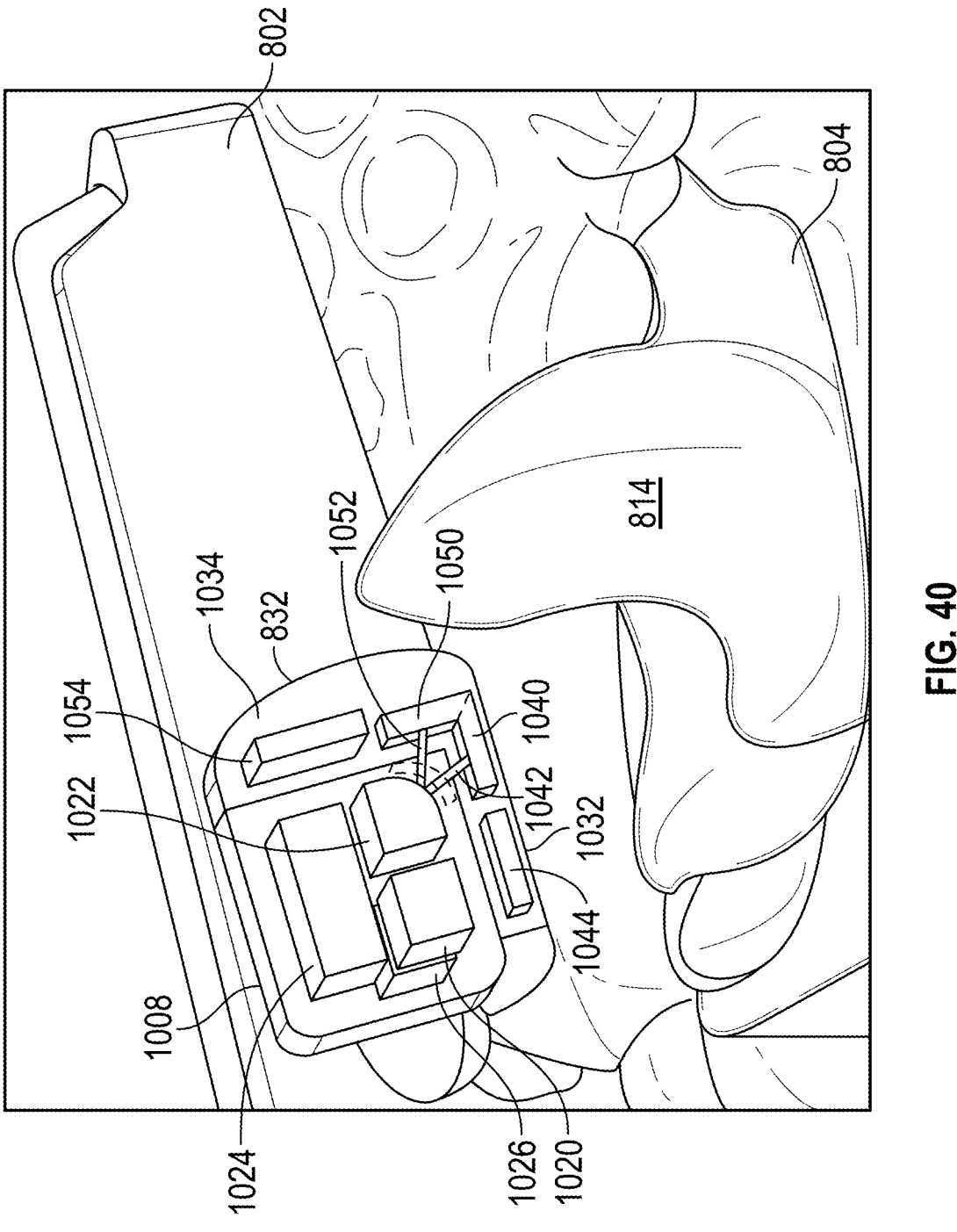
FIG. 40 is a right, side view of a second embodiment of the mandibular repositioning device having integrated anterior-posterior adjustment and cranial-caudal adjustment built into the maxillary piece.

Turning now to FIG. 40, another embodiment having anterior-posterior movement and the cranial-caudal movement of the mandibular repositioning device integrated into the maxillary piece 802 for control of the driver flange 832 is shown. The driver flange 832 has a posteriorly extending extension 1032 extending from the most caudal portion of the driver flange 832. The extension 1032 includes a first plate 1040 therein connected to a first robotic arm 1042 and a first position sensor 1044. The main portion 1034 of the driver flange 832 includes a second plate 1050 connected to a second robotic arm 1052 and a second position sensor 1054. The first plate 1040 is juxtaposed to the second plate 1050 at the junction of the extension 1033 to the main portion 1034 of the driver flange 832. The first plate and the second plate 1040, 1050 can be fixedly connected to move the entire flange together, such that the movement is more angular, thereby having both anterior-posterior and cranial-caudal adjustments simultaneously. In another embodiment, the extension 1033 may move independently from the main portion 1034 as represented by the dashed line in FIG. 40. The robotic arms, 1042, 1052 may be extending arms, such as telescoping arms, and terminate at their respective plates 1040, 1050 with an articulating joint, such as a ball and socket joint, for greater range of motion.

Figure 41:
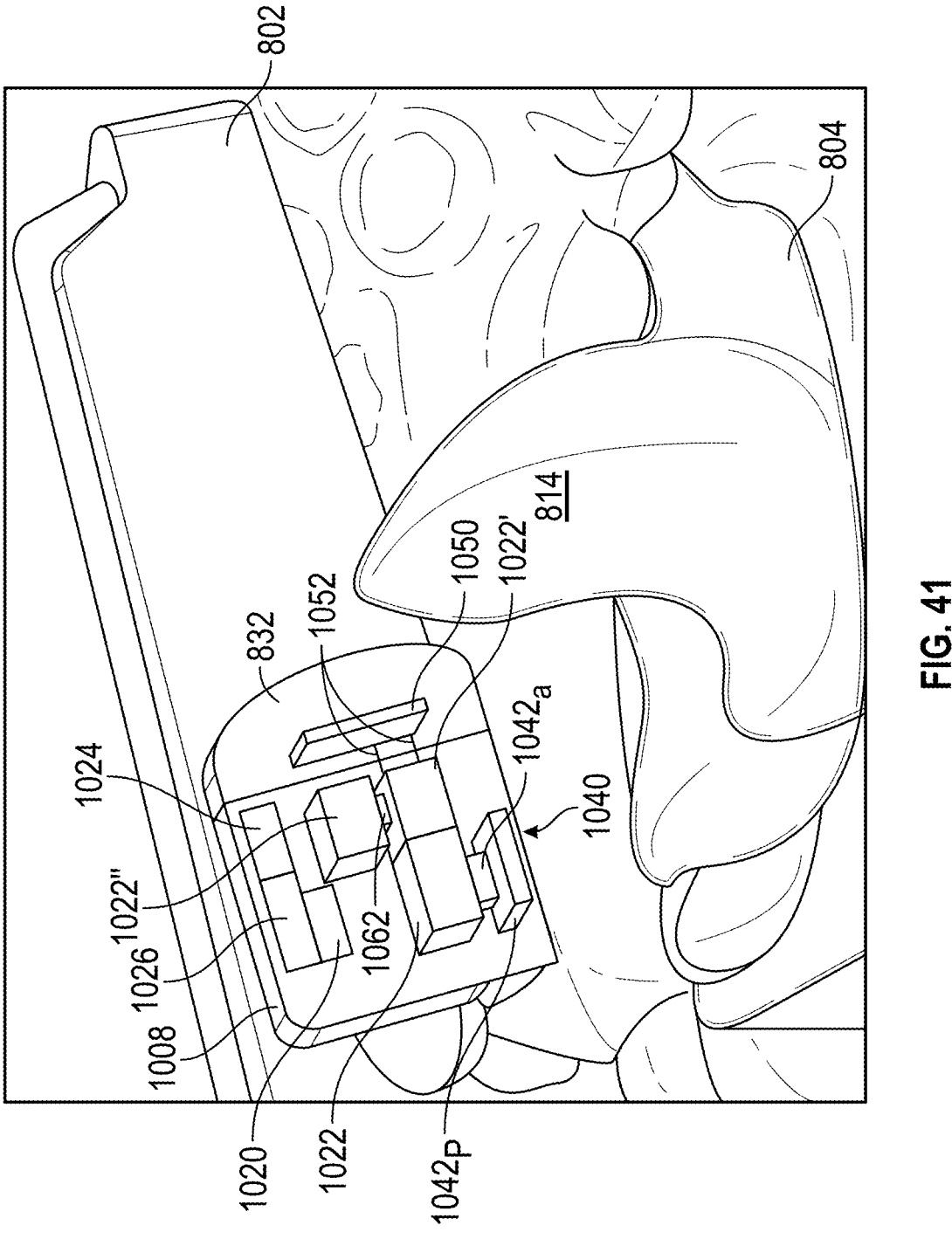
FIG. 41 is a right, side view of a third embodiment of the mandibular repositioning device having integrated anterior-posterior adjustment and cranial-caudal adjustment built into the maxillary piece.

The embodiments of FIGS. 40-41 have other features similar to the embodiment of FIG. 39, such as the microprocessor 1024 and memory 1026 for artificial intelligence control of the robotic arms 1042, 1052 relative to data from sensors, including the first and second position sensors 1044, 1054, even if not illustrated in the figures.

Turning now to FIG. 41, the first plate 1040 is separate from the driver flange 832 and is seated in the bottom of the housing 1008. The first plate 1040 has its own motor 1022 that is separate and independent form a second motor 1022' that controls the movement of the second plate 1052 which is positioned inside the driver flange 832. As indicated for the other embodiments, the arms connecting each motor to each plate may be extending, e.g., telescoping, and have an articulated connection to its plate, e.g., a ball and socket joint. Here, there is a third motor 1022''' present that is positioned with a third robotic arm 1062 to move the entire anterior-posterior assembly (second motor 1022', second robotic arm 1052, and second plate 1050) in the cranial-caudal direction, thereby moving the driver flange for cranial-caudal adjustments simultaneously, independently, and/or sequentially with anterior-posterior adjustments. As noted above, these adjustments may be used to maintain contact between the driver flange 832 and the protrusive flange 824 during caudal and anterior movement of the mandibular piece, thereby avoiding the cranial tip of the protrusive flange from dropping below the driver flange. This enables unrestricted mouth opening by the user.

In one embodiment of FIG. 41, dual robotic arms 1042 connect the first plate 1040 to the first motor 1022 and dual robotic arms 1052 connect the second plate 1050 to the second motor 1022''. The presence of dual robotic arms 1042, 1052 provides the ability to introduce a tilt to the driver flange 832 and/or the first plate 1040. For the driver flange 832, the tilt function can have the more caudally positioned arm move more than the more cranially positioned arm such that the effect of a greater posterior lean, such as in FIG. 38, is achieved, thereby providing more anterior advancement for each degree of mouth opening. Similarly, if desired, the opposite movement of the dual arms 1052 is possible to produces less posterior lean, such as in FIG. 37, thereby providing less anterior advancement for each degree of mouth opening.

Also, in the embodiment of FIG. 41, the dual robotic arms 1042 can move the posterior end of the first plate 1040 less than the anterior end of the first plate 1040. In one non-limiting example, for a mouth opening of 1 degree (1.66 mm) requires the posterior arm $1042_p$ to move the posterior end of the first plate 0.95 mm and the anterior arm $1042_a$ to move the anterior end of the first plate 1.06 mm. This can used to introduce the equivalent of the plateau similar to those of FIG. 27-29 in the at rest position with dynamic alterations possible during activity or sleep through robotic and machine learning algorithms.

Each of the systems disclosed in FIGS. 39-41 has a power source 1020 that is rechargeable and has the recharging features described herein for other embodiments. Moreover, each system is compatible with the controller stations described herein and used artificial intelligence to drive the motor(s) 1022 and adjustments to the mandibular repositioning devices.

Figure 42:
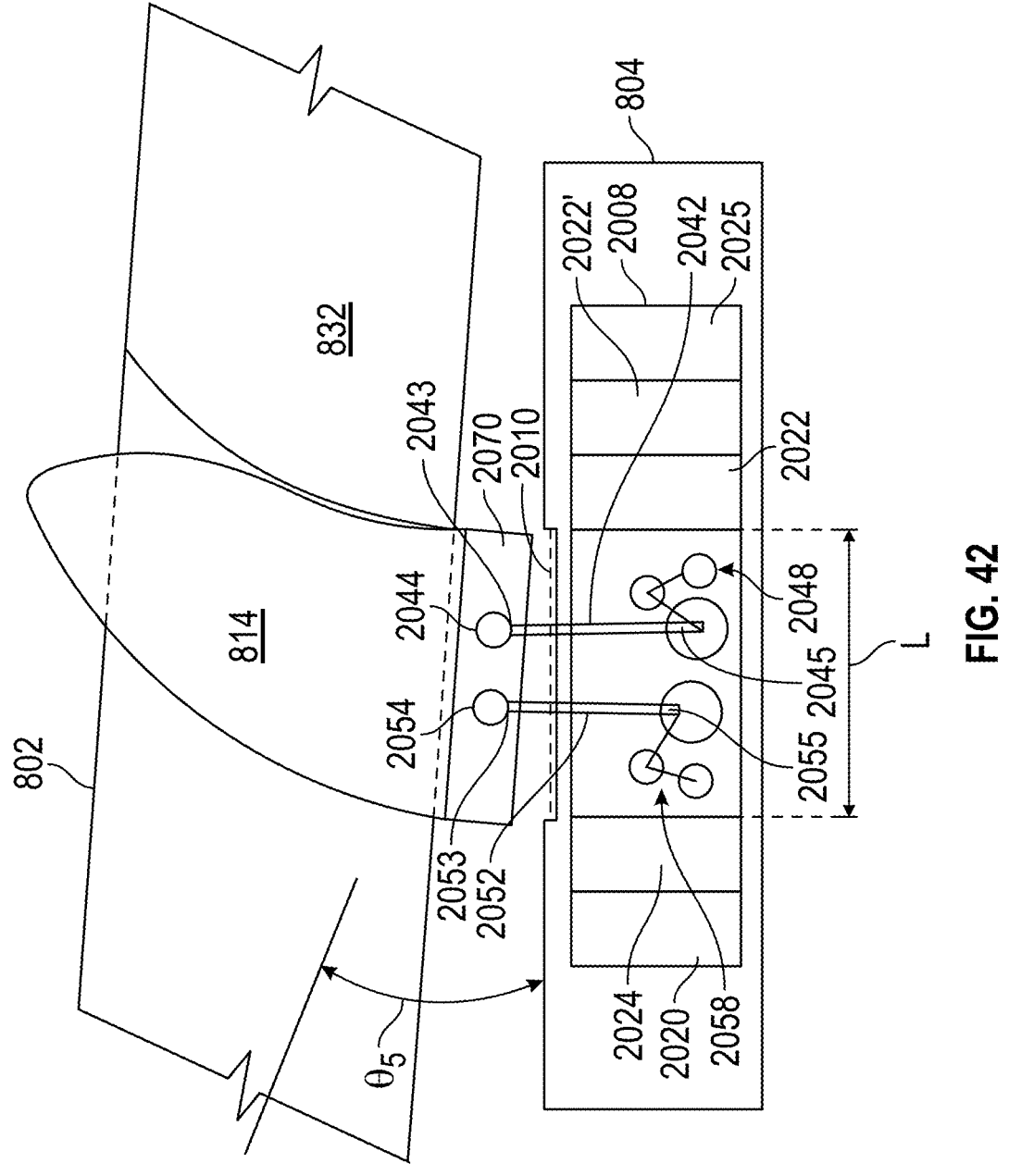
FIG. 42 is a side view sketch of a mandibular repositioning device having a robotically controlled and motorized adjustment mechanism built into the mandibular piece for movement of the protrusive flange and the plateau.

Turning now to FIG. 42, this embodiment has arms 2042, 2052 controlling movement of the protrusive flange 814 shown as the left molar region of the mandibular piece 804. The same is true for a right molar region. Each molar region has a housing 2008 of sufficient size to enclose electronics that accomplish anterior to posterior movement, cranial to caudal movement, and angular movement ($\theta_5$). For the anterior to posterior movement, the housing has a waterproof groove 2010 through which the arms 2042, 2052 extends. The length (L) of the groove is in a range of 1 mm to 12 mm, preferably 5 mm to 12 mm to provide a range of anterior to posterior advancement. A first end 2043, 2053 of each arm 2042, 2052 is connected to a respective receiver 2044, 2054 in the protrusive flange 814 at a position inside the base thereof or in a plateau 2070, if present, such as shown in FIG. 42. The receivers 2044, 2054 can provide a removably, replaceable snap-fit connection for changing the protrusive flange 814 or can receive a screw or other fastener. In one embodiment, the receivers 2044, 2054 facilitate a permanent attachment of the protrusive flange 814 to the arms 2042, 2052. When the plateau 2070 is present, it can have any of the features of the embodiments described herein.

The arms 2042, 2052 may be mechanically functional or may be robotic with artificial intelligence control thereof. The arms 2042, 2052 are juxtaposed to one another in an anterior to posterior relationship within the housing 2008. A second end 2045, 2055 of each robotic arm 2042, 2052 is operatively connected to a respective gear system 2048, 2058 that are individually controlled by a microprocessor 2024 within the housing 2008. The microprocessor 2024, a first motor 2022 and second motor 2022', power source 2020, at least one sensor 2025, and other optional electronics within the housing. The optional electronics can be any of the options discussed herein for any of the other embodiments. The individual control of the gear systems 2048, 2058 enables control of the arms 2042, 2052 simultaneously in synchronized or sequential operations or individually for any of the desired advancements for a particular patient's needs. The arms 2042, 2052 in any embodiment can have a removably, replaceable snap-fit to their respective gear system 2048, 2058. As such, arms of differing lengths can be provided and used as suitable for different conditions of the user, such as a change in physical activity or a change in health.

Still referring to FIG. 42, the mandibular repositioning device can include any number and type of sensors 2025 and stimulators from any of the embodiments disclosed herein and the microprocessor 2024 can execute necessary algorithms to achieve the anterior to posterior movement, cranial to caudal movement, and angular movement. The arms 2042, 2052 can provide up to 12 mm of anterior to posterior movement, up to 14 mm of cranial to caudal movement, and up to 25 degrees of angular movement ($\theta_5$) to the protrusive flange. To achieve the angular movement, the anteriorly positioned arm 2052 moves the protrusive flange more in the cranial direction than the posteriorly positioned arm 2042 as shown in FIG. 42. As discussed repeatedly herein, the anterior to posterior movement provides anterior mandibular and lingual advancement and the vertical and angular advancements provide caudal displacement of the mandible and tongue as well. In one embodiment, the microprocessor is a quantum microchip or a photonic integrated circuit, has non-transitory member, a renewable or rechargeable power source, a means to charge the power source, means for the microprocessors in each housing (right and left sides) to communicate with one another and/or external devices including those disclosed herein. Continuous machine learning will provide internal biofeedback and commands integrated with external resources. These embodiments for the protrusive flange are compatible with all other embodiments disclosed herein.

Referring back to FIGS. 1 and 4, at least one stimulator 116, but preferably both stimulators 116, include a first sensor 150L/R and/or a second sensor 152L/R, but preferably both sensors. 150L and 152L stands for the left side of the user and 150R and 152 R stands for the right side of the user. The sensors 150L/R and 152L/R may be selected from a variety of sensors to create which every combination is the most likely to be useful in diagnosing or treating the user. The sensors are selected form the group consisting of a pulse oximetry sensor, a vibration sensor, an airflow sensor, a pH sensor, a combination pulse oximetry/vibration and airflow sensor, an EKG sensor, EEG sensor, EMG sensor, EOG sensor, lactic acid sensor, a pulse transit time (PTT) sensor, an ultrasound sensor (echocardiography), an electro-oculogram sensor, a temperature sensor, a body position or jaw position sensor (such as a potentiometer), an electromyogram sensor, a pressure measurement sensor, a hygrometer sensor, a microphone or sound recording sensor, video recording, and hygroscopic/hydration sensor. In one embodiment the first sensor is a combination pulse oximetry/vibration and airflow sensor and the second sensor is a pH sensor. In another embodiment, the first sensor is a pulse oximetry sensor, and the second sensor is a vibration and airflow sensor. Any number of combinations of the sensors listed above is possible and can best be selected by a medical professional based on data relative to the pre-selected end user. Sensors in the left side and right side could be symmetric or complimentary or asymmetric. For example, CMUT/IVUS sensor may have better signal delivery and reception of carotid blood flow when placed on the left side and not as good a reading from the right side. Thus, it is placed only on the left side. The EKG sensor may have better reading from the right side than from the left side and thus is placed on the right side. Together, the EKG sensor and ultrasound sensor create complete cardiovascular hemodynamic data.

The stimulator 116 may also be accompanied by a sensor or sensors that can record EEG (electro-encephalogram), EOG (electro-oculogram), electromyogram (EMG) for the tongue muscles and NC (Nerve conduction) data from the nerves of the tongue, pharynx and muscles of mastication (jaw muscles) and phonation (speech). These sensors may transmit these data to the controller 200 (described in more detail below) through variety of industry standard wireless protocols that are currently in use for wireless EMG, NC and EEG recordings in other skin surface applications in neurology and sleep laboratories. Data from such sensors will be useful for detection of various medical diseases as it will be computed in time-synchronized manner by the controller 200 and cloud based servers in system 300 described in more detail below and will help to determine cause-effect of many medical diseases. The sensors will also provide feedback to controller 200 to gauge effectiveness of electric stimulation of the tongue or forward movement of the tongue and mandible and thus allowing the controller to make fine adjustments to all components of the system.

The length L of each stimulator 116 will be pre-selected to fit the user's mouth and tongue, in particular for adequate contact with the base of the tongue (genioglossus muscle) during sleep or while awake performing certain activities. Each stimulator 116 has a single or dual electrode 154 connected to the power source 120 and generates an electrical impulse that travels through the electrode to one or more of the lingual muscles of the tongue identified above, which contracts the lingual muscle(s) to create a forward movement of the tongue. The forward movement of the tongue increases the cross-sectional open airway diameter in transvers, vertical and antero-posterior dimensions, thus increasing the aggregate volume of open airway and exponentially reducing air-flow resistance. The power source for the single or dual electrode can be a direct current (DC) power source or may employ any other technology such as electro-magnetic energy, photon energy among other forms of energy. The electrical impulses' power source will be in volts or microvolts and the current, likely in milli-Amps (usually 2-6 mA), will be pre-selected on a per patient basis. The power, current, and capacity will typically be within a range suitable for effective performance of mated hardware and safe for use with cardiac pacemakers, defibrillators, deep brain stimulators, or spinal cord stimulators.

The forward movement of the mandible (protrusion) is performed by lateral pterygoids, medial pterygoids and masseter muscles. These are stimulated by the mandibular branch of the trigeminal nerve. The neuronal firing rate drops during sleep relaxing these muscles causing the jaw to fall back (retrusion) and thus allowing the tongue to fall back (retro-glossal movement) into the airway as well creating a narrow airway which is the cause of obstructive sleep apnea, oxygen desaturation, elevated blood-pressure, cardiac arrhythmia, disruption in sleep and nocturnal acid reflux. The transverse stimulator 116 can specifically target these muscle groups and their distributing nerve and stimulate and sense electrical activity of these various muscles individually or together inside the oral cavity.

Also, the stimulators 116 can stimulate selected muscles to improve their strength. This can be a training or a retraining exercise, for example, after a stroke (swallowing difficulty or speech difficulty) or for children with speech pathologies. If sensors are present in the stimulators 116, the sensors can provide data to the controller station 200 and the system 300 of FIG. 11 to determine which muscle and/or muscle group needs attention. Thus, the shape of exterior surface/housing of the stimulators 116 are shaped and sized to direct each and every sensor, stimulator or combination thereof to the appropriate location inside the oral cavity.

The pulse oximetry sensor 150 is positioned in one or both stimulators 116 at a position enabling direct contact with the base of the tongue from which data will be collected. The position of the pulse oximetry sensor 150 is generally antero-superiorly positioned for measuring pulse-oximetry through the blood-flow of the tongue. The vibration and airflow sensor 152 is positioned in one or both stimulators 116 at a position suitable for airflow measurements, which can indicate when there is a restriction of airflow, and vibration measurements (sub-sonic and sonic) that are an indication of inaudible and audible snores. The vibration and airflow sensor 152 faces posteriorly to measure snores and airflow resistance/pressure from the airway.

The power source 120, 121 in all embodiments may be a rechargeable battery. In one embodiment, the rechargeable battery is one or more micro-lithium ion batteries in each housing 108, 109. Solar/light charging energy source that can be recharged by ambient lighting (used in the watch maker industry) or solar power may also be considered for a rechargeable source of energy. The rechargeable battery may have a maximum discharge milli-amperage creating a mechanical mandibular protrusion or retrusion ranging between 1-10 mm in linear dimensions for the movement of the drivers 130, 132.

As seen in FIGS. 1 and 2, each housing 108, 109 of the mandibular and maxillary pieces, respectfully, include a charging member 118, 119, such as a charging plate, in an exterior surface thereof. In the figures, the charging plate is in a lateral side of the housing 108, 109, but is not limited thereto.

As best seen in FIG. 3, the first driver 130 may be a flat plate connected to the motor 122 by the linkages 134.

The motor 122, 123 in all embodiments may be a single or dual piezoelectric motor having a linearly movable linkage(s). Micro motors based on piezo electric materials are commercially available from Piezo Motor, a company headquartered in Sweden and may be modified as needed for use in the disclosed devices. The motor 122, 123 may include a position sensor.

As best seen in FIGS. 3 and 6, the maxillary piece 102 sits on the mandibular piece 104 with the first driver 130 operatively engaged with the maxillary piece 102 and the second driver 132 operatively engaged with the protrusive flange 114, 114', or 114" of the mandibular piece 104. Each of the drivers 130, 132 can move the jaws in increments of 0.1 mm up to 2 mm with each movement with a maximum of 12 mm in the respective direction. The protrusive flange 114, 114', 114", is moveable by the second driver 132 in a range from 0.1 mm to 11 mm and the first driver 130 can lift the maxillary portion in a range from 0.1 mm to 12 mm.

Referring again to FIG. 6, the second driver 132 has a head 136 that is shaped to fit the shape of the posterior side 145 of the protrusive flange 114'. The head 136 has a convexly-shaped anterior side to press against the posterior side 145 of the protrusive flange 114'.

Figure 9:
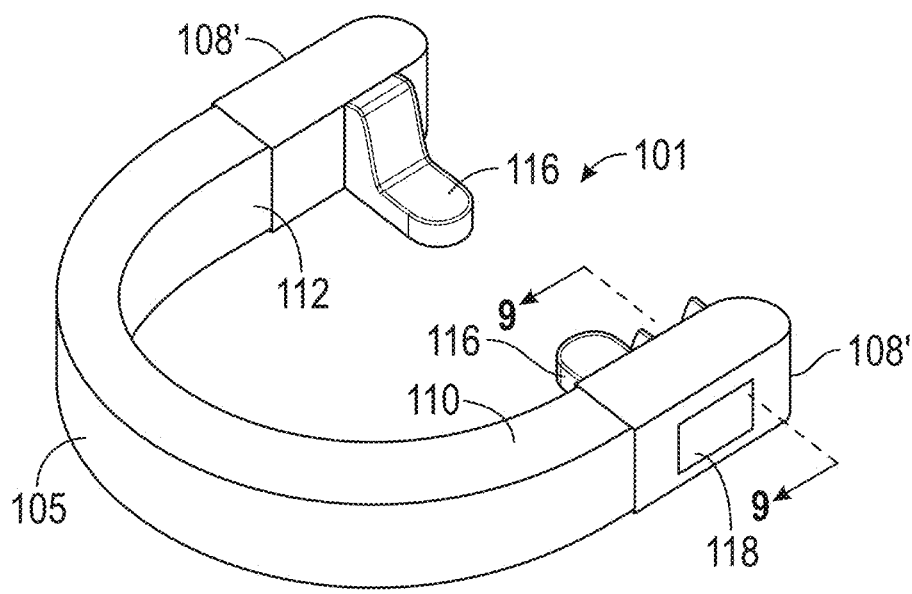
FIG. 9 is a side, perspective view of an embodiment of a mandibular device having at least a stimulator electrode therein.

Turning now to FIG. 9, a mandibular device 101 is illustrated that has just the stimulator 116 and a mandibular teeth covering 105. As such, the maxillary piece can comprise of a teeth covering 107 as shown in FIG. 2 without the housings 109 or be absent, i.e., the user can just have the mandibular device 101 in their mouth during use. Dual housings 108' are present with one each proximate a left molar portion 110 and a right molar portion 112. A stimulator 116 extends from each housing 108' toward the tongue at a position to lie under the tongue in contact with lingual muscles, in particular the Genioglossus (GG), the Geniohyoid (GH), sub-mentalis (SM), and Glossopharyngeal (GP). Each housing 108' includes a charging feature 118 for recharging any battery(ies) housed therein, as described above.

Figure 10:
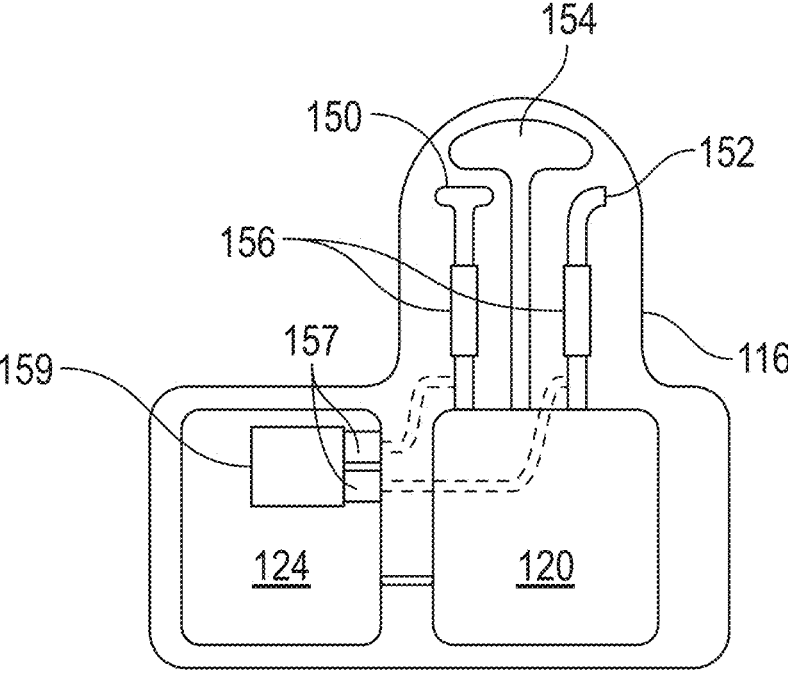
FIG. 10 is an enlarged cross-sectional view of the mandibular device along line 9-9 in FIG. 9.

Referring now to the cross-section of FIG. 10 through one of the stimulators 116, each stimulator 116 houses therein, in a fluid-tight manner, a first sensor 150, a second sensor 152, and a stimulator electrode 154. In FIG. 10, the first sensor 150, the second sensor 152, and the stimulator electrode 154 are each electrically connected to the power source 120 within housing 108'. The electrical connections may be direct connections to the power source 120, which may be accomplished by a plug-n-play electrical connector 156, or, as represented by the dashed lines, may be accomplished by a plug-in style connector 157 to the microprocessor 159 and thereby to the power source.

In one embodiment, the first sensor 150 is a pulse oxygen sensor continually measuring oxygen data at the base of the tongue and the second sensor 152 is a vibration/air flow sensor measuring snoring, turbulent flow, and vibrations from inside the user's mouth. As noted above with respect to FIG. 4, multiple other sensors and sensor combinations are possible that will provide data to the microprocessor 159. The circuit board 124 within the housing 108' is in operative connection to the power source to be powered and to control activation of the stimulator electrode 154 in response to data received by the circuit board 124, more particularly, the microprocessor 159, from the first sensor 150 and/or the second sensor 152. As discussed the microprocessor 159 receives the sensor data, processes the sensor data, and determines whether the stimulator electrode 154 needs activated.

Each of the stimulators 116 may include a pH electrode too. The pH electrode will measure the acidity at the back of the tongue, which if too high is an indication of chronic high acid reflux.

Figure 11:
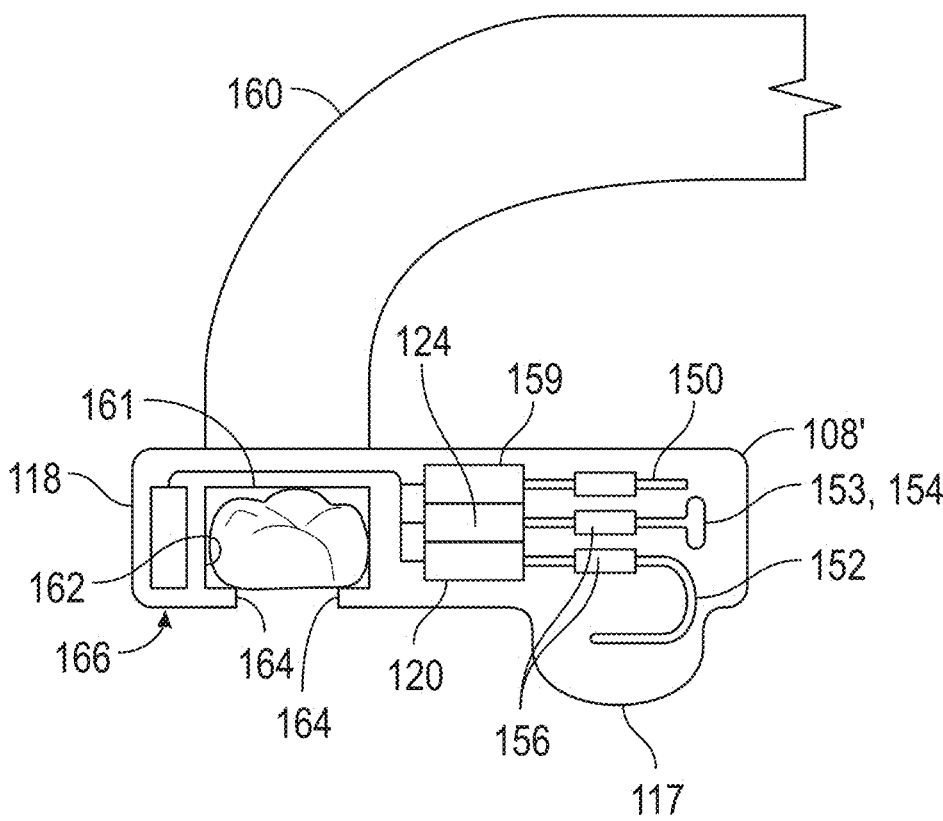
FIG. 11 is a cross-sectional view of another embodiment of a mandibular device that is removable attachable to a teeth covering.

Referring now to the FIG. 11, which is a transverse cross-section through one of the stimulator/sensor protrusions 117 and housings 108' of a mandibular device similar to the mandibular device 101 of FIG. 9. In this embodiment, each housing 108' and stimulator/sensor protrusion 117, rather than being built as part of the teeth covering 160, are removably attachable to the teeth covering 160. Each housing 108' defines a groove 162 shaped to receive therein an end 161 of the teeth covering 160, such that one housing 108' is removably attached to a first end 161 defining a left molar portion and the other housing 108' (not shown) is removably attached to a second end (not shown) of the teeth covering 160 defining a right molar potion thereof. The groove 162 may have opposing flanges 164 positioned at and parallel with a bottom surface 166 of its housing 108' and extending toward the open void defined by the groove 162. The groove 162 of each housing 108' may be slid over and be received on the teeth covering, may have a snap fit to the teeth covering, may have an interference fit, or may be fabricated in two parts that can snap into each other over a predetermined location of the teeth covering or may be fabricated with three-dimensional printing over a teeth covering. The illustrated embodiment in FIG. 11 has the housing 108' slidingly received on the first end 161 of the teeth covering 160 with the flanges 164 resting against bottom surfaces of each of the sides of the teeth covering 160. Regardless of the type of attachment, each housing 108' is movable fore and aft to adjust the position of the stimulator/sensor portion under the correct position under the tongue of the user.

Since the housings 108' are removably attachable to the teeth covering 160, each housing and or teeth covering may be disposable or reusable. When the housings 108' are reusable, the housings are constructed of a material suitable for sterilization between uses, such as by autoclave sterilization. Housed within each housing 108', in a fluid-tight manner, is a first sensor 150, and an optional second sensor 152, and an optional third sensor 153 or a stimulator electrode 154 or even a high-pressure pellet discharge system. Each of the first sensor 150, the second sensor 152, and the third sensor 153 or the stimulator electrode 154 are electrically connected to the power source 120. The electrical connections may be direct connections to the power source 120, which may be accomplished by a plug-n-play electrical connector 156, or may be accomplished by a plug-in style connector to the microprocessor 159 and thereby to the power source 120. The housings 108' each include a charging member 118 in an exterior surface thereof for coordination with one of the charging units 202, 204 of the controller station 200 of FIG. 5.

In one embodiment, only the first sensor 150 is present. The first sensor 150 may be, but is not limited to, a pulse oxygen sensor, a vibration and airflow sensor, a pH sensor, a doppler ultrasound, an M-Mode ultrasound, a 2D ultrasound, 3D ultrasound, a pressure plate for measuring bruxism, a pulse transit time sensor, non-invasive ventilation systolic/diastolic blood pressure sensor, a carotid doppler (trans-oral) sensor, or a cardiac trans-oral echocardiography sensor or a camera/videography system, or any other sensor identified herein. In one embodiment, the first sensor 150 is a pH sensor. In another embodiment, the first sensor 150 is a pulse oxygen sensor continually measuring oxygen data.

The mandibular device 101 is used with the controller station 200 in a diagnostic mode.

Since there are two housings 108' each having a stimulator/sensor protrusion 117, each housing 108' may have a different type of sensor for the first sensor 150 or one may have a first sensor 150 and the other may have the stimulator 154. As such, the mandibular device 101 can be used in a diagnostic mode or a treatment mode depending upon the selection of sensors and/or stimulator in the housings 108', thereby providing great versatility in use. Furthermore, since the housings 108' are removable attachable to the teeth covering 160, the housings 108' can be switched for housings having different sensors in a sequence of nights to assess various parameters of the user or during the day or both night and day. The mandibular or maxillary housings or teeth coverings, when used alone (mandibular or maxillary) should allow most speech functions and thus can be used during the course of a normal day. The data interfaces with standard Bluetooth functionality or WIFI functionality and the controller station may be used as a mobile unit with Bluetooth and WIFI functionality and as such may be carried to work or elsewhere since it has its own rechargeable battery operations. Controller station will be interfaced with proprietary or open platform program that can be securely loaded on variety of computer systems and hand-held smart devices.

Figure 12:
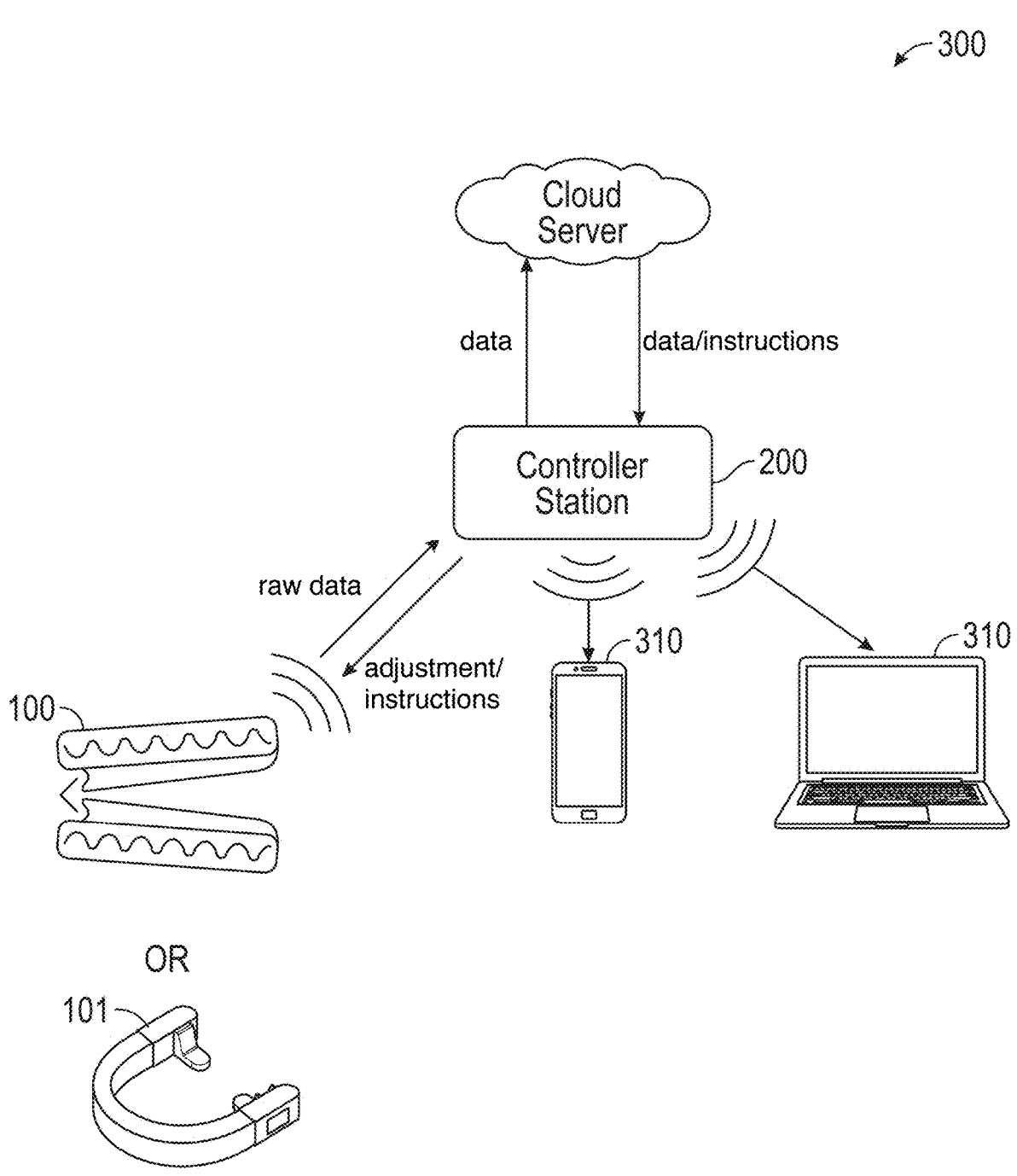
FIG. 12 is a schematic illustration of a system in operative communication with the MRLD of FIG. 1 or the mandibular device of FIG. 8.

In another embodiment, the first sensor 150 in a first of the housings 108' is a pulse oxygen sensor continually measuring oxygen data at the base of the tongue and the second sensor 152 is a vibration/air flow sensor measuring snoring, turbulent flow, and vibrations from inside the user's mouth; the second of the housings 108' has a pH sensor as the first sensor and includes the stimulator 154. Here, diagnostic and treatment functions are possible that are coordinated by the system 300 or any of its components such as controller or PC or smart device. The sensors 150, 152 provide data to the microprocessor 159. The circuit board 124 within the housing 108' is in operative connection to the power source to be powered and to control activation of the stimulator electrode 154 in response to data received by the circuit board 124, more particularly, the microprocessor 159, from the first sensor 150 and/or the second sensor 152 and/or from instructions from the controller station 200 and/or the cloud server as shown in FIG. 12 (described in more detail below) to effect a treatment. For example, if the pH sensor senses an increasing acid condition as the user sleeps and the other sensors measure airflow resistance or decreased airflow, then the stimulator will be activated to open the airway and the system will then determine if the pH decreases. Such a causal relationship may help reduce/prevent significant nocturnal acid reflux and thus minimize or eliminate the use of acid reflux medications. Moreover, the combination of sensors can be selected to determine time synchronization of the pH to other physiological occurrences of the user, such as body position, inspiration, expiration, sleep measurements, oxygenation, bruxism, snoring, apnea, etc. Ideally, a link between acid reflux and other physiological occurrences can be determined and then used for treatment.

Moreover, using the controller station 200 and cloud server of the system 300, it will be possible to receive data regarding the user's input of food and time consumed to act proactively during sleep based on a correlation of digestion time and acid reflux onset. This capability may be extended to input of any and all medications, physiological data such as BP, EKG and blood sugar, and to administering of any and all medications during the day (prompted to the user through handheld device) or night (automatically performed if pressure pellet for medication is available to the system to discharge sub-lingually or intra-orally in liquid form or inhaled as micro-aerosol powder form.

The teeth covering 160 in the embodiment of FIG. 11 can be as simple as a plastic boil and bite mandibular device onto which the housings 108' are removably attachable. In this manner, the teeth covering 160 is disposable and are readily available. Other teeth coverings 160 are commercially available that are generally cheap and disposable such as ora-guard, sonabul, oral-b etc. However, the teeth covering 160 is not required to be disposable. Instead, the teeth covering 160 can be constructed of a material that is sterilizable such that the teeth covering is reusable by a user or users over a preselected time period while sterilizing the housings 108' and utilizing any combination of housings 108' having a variety of sensors to monitor as many physiological parameters of the user as selected by administering expert.

Figure 13:
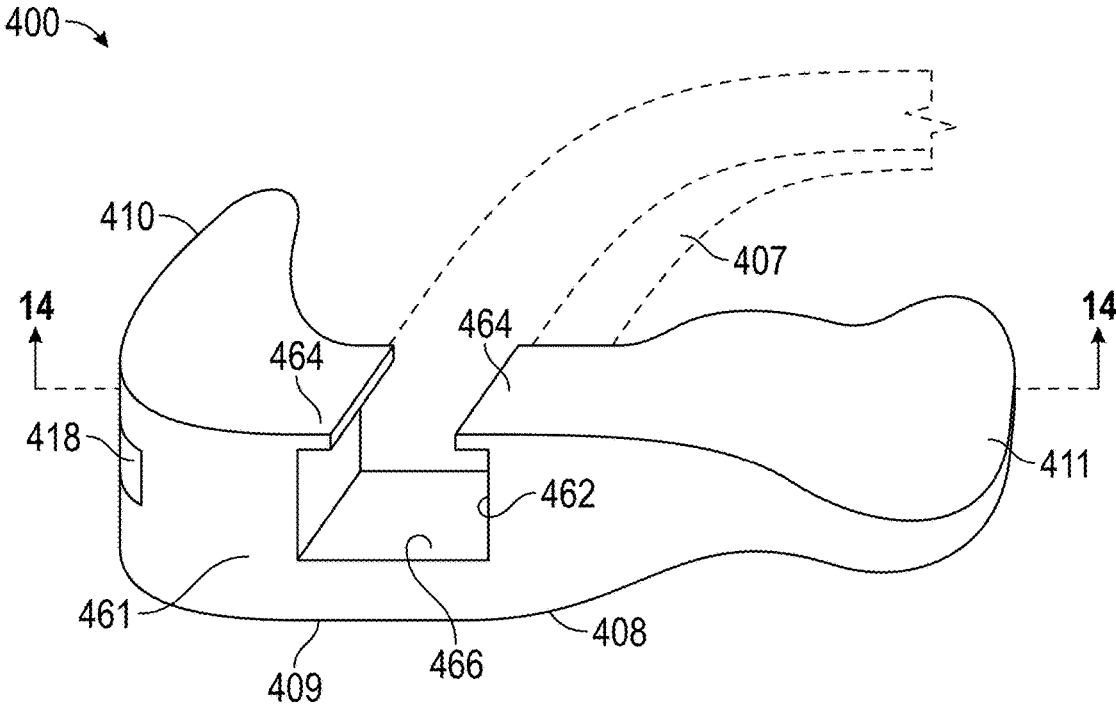
FIG. 13 is a rear, perspective view of a maxillary device having at least a stimulator electrode therein.
Figure 14:
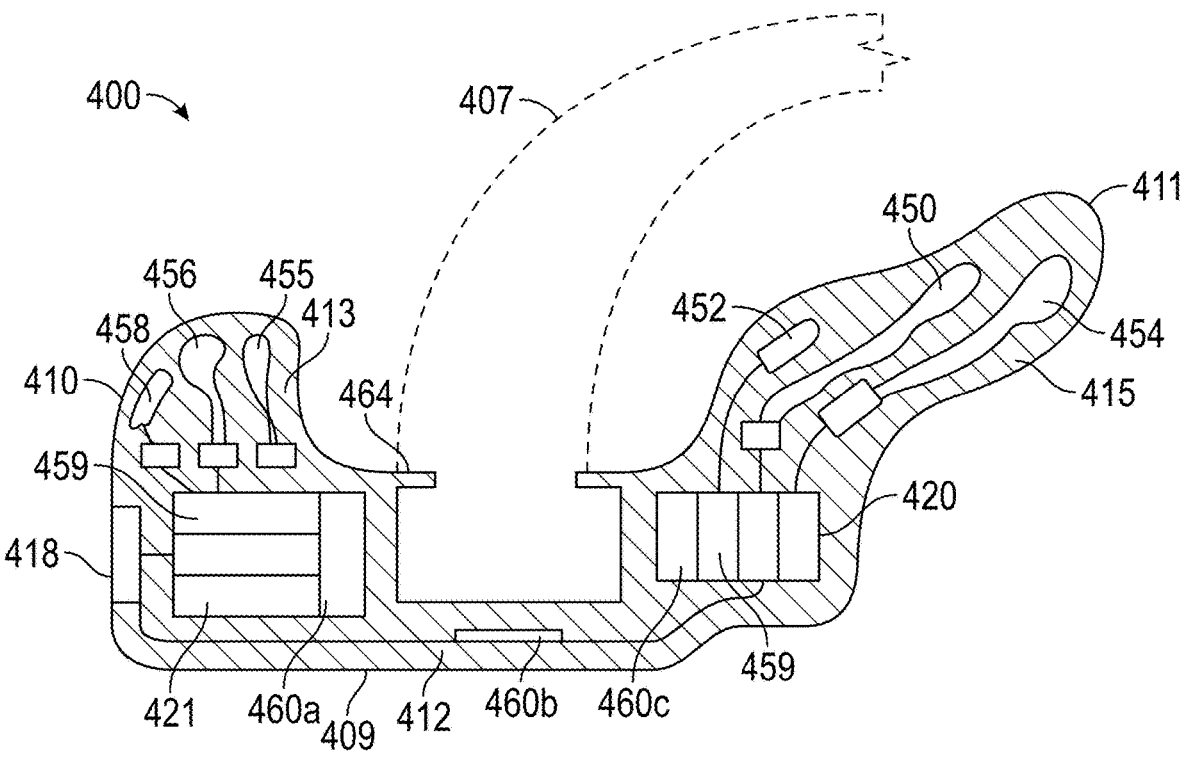
FIG. 14 is a cross-sectional view along line 14-14 of FIG. 13.

Turning now to FIGS. 13 and 14, a maxillary device 400 that is either integral with a teeth covering 407 or removably attachable to the teeth covering 407 is shown. A teeth covering includes a palatal expander or retainer device as well as mouthpiece covering the teeth. Teeth covering 407 may have one maxillary device 400 at the left molar portion and a second maxillary device (the mirror image of the maxillary device 400 in FIG. 13) at the right molar portion or placed asymmetrically for individualized needs. Each maxillary device 400 has a housing 408 that defines a tooth connecting portion 409 one or both of a buccal housing 410 and a palate housing 411 that each define an internal cavities 412, 413, 415, respectively, in which is housed, in a fluid-tight manner, a stimulator electrode 454, 455 and/or one or more sensors 450, 452 and/or other data collecting devices 456.

The buccal housing 410, when present, is shaped to fit between the user's teeth and cheek and may extend anteriorly and/or posteriorly to collect data and/or stimulate muscles within the oral cavity. The buccal housing 410 can stimulate the lateral pterygoid muscles to move the jaw forward. The jaw may be moved forward during sleep or while awake. While awake, the stimulator 455 can coordinate muscles of mastication or swallowing.

The palate housing 411 is shaped/contoured to rest against the roof of the user's mouth in contact with the hard palate and the soft palate and clings to the surface of the mucosa in the mouth in order to have good contact for purpose of stimulation of the muscles of swallowing and of the soft palate. The palate housing 411 extends in any possible direction to acquire physiological data from the oral cavity and to stimulate the lateral pterygoid muscles for protrusive movement of the mandible or stimulate muscles of the soft palate and uvula so as to stiffen these structures to reduce snoring or for detection and treatment of speech or swallowing pathologies. The speech or swallowing pathologies may include, for example, post-stroke recovery or reconstructive surgery of the maxilla-facial region recovery or short frenulum syndrome with associated speech defects or micrognathia syndrome in children such as is seen in pediatric obstructive sleep apnea or in Treacher-Collins syndrome.

Each housing 408 includes a charging feature 418 in an exterior surface thereof for recharging any on-board power source 420, such as battery(ies), housed within the internal cavities 413, 415 or in any portion of the maxillary or mandibular device, even in remote parts of the device, i.e., there is no requirement for the batteries to be adjacent to the location of sensors. The batteries may be any of those discussed above with respect to other embodiments.

In FIG. 14, the housing 408 includes a photography and/or videography array 460 having photography and videography units 460*a*. 460*b*, 460*c* positioned to face each side and a bottom of a tooth, respectively, as shown in FIG. 14. The photography and/or videography array 460 can include, but is not limited to, unidirectional or multidirectional collection using single or multiple digital cameras to map dental structure, oral cavity structure, airway structure etc. and record sounds. When intended to map the oral cavity or airway structure, the unidirectional or multidirectional units are oriented outward toward the oral cavity rather than toward a tooth. These photography/videography arrays may be used to create recordings of teeth and gums (maxillary or mandibular) for use in general dentistry, endodontic and periodontal applications such as fabrication of enamel, measurement of enamel wear in bruxism, artificial teeth construction, crown construction, gum disease detection and treatment, and for 3-D printing of the mandibular and maxillary devices disclosed herein. When the photography/videography arrays face a tooth, the housing 408 may be configured to slide back and forth over the teeth to create a video or photo recording thereof for dental use. The housing 408 may attached to a wand or a fiberoptic flexible wand that can be manually moved along the teeth by the dentist or physician to help take images of single or multiple teeth or the complete dentition for dental applications or MRD (mandibular repositioning device) construction applications.

The stimulator electrodes 454, 455 are as discussed above for other embodiments. The sensors 450, 452, 456, 568 include any and all of the sensors discussed above for other embodiments. One of the sensors can be a sound sensor to collect sounds such as those during sleep (e.g., snoring or grinding of the teeth) or those related to speech and swallowing that may be useful to define specific speech defects and swallowing defects. All these functions may be stand-alone or in synergy with stimulators, mandibular and/or maxillary movement devices, videography, photography, etc.

In FIG. 14, the first sensor 450, the second sensor 452, and the stimulator electrode 454 are each electrically connected to the power source 420 within the palate housing 411. Likewise, a third sensor 456, a fourth sensor 458, and the stimulator electrode 455 are each electrically connected to the power source 421 within the buccal housing 409. The electrical connections may be direct connections to the power source 420, 421 which may be accomplished by a plug-n-play electrical connector or may be accomplished by a plug-in style connector directly to the microprocessor 459 and thereby to the power source 420, 421.

In the removably attachable embodiment of FIG. 13, the housing 408 defines a groove 462 shaped to receive therein an end 461 of the teeth covering 407. A first housing 408 is removably attached to a first end 461 defining a left molar portion and a second housing, if present, is removably attached to a second end (not shown) of the teeth covering 407 defining a right molar potion thereof. The groove 462 may have opposing flanges 464 positioned at and parallel with a bottom surface 466 of its housing 408 and extending toward the open void defined by the groove 462. The groove 462 of the housing 408 may be slid over and be received on the teeth covering, may have a snap fit to the teeth covering, may have an interference fit, or may be fabricated in two parts that can snap into each other over a predetermined location of the teeth covering or may be fabricated with three-dimensional printing over a teeth covering. It may be designed to fit directly over the teeth in the absence of any other teeth covering. In this embodiment, the housing 408 will be a teeth covering itself. The illustrated embodiment in FIG. 13 has the housing 408 slidingly received on the first end 461 of the teeth covering 407 with the flanges 464 resting against bottom surfaces of each of the sides of the teeth covering. Regardless of the type of attachment, housing 408 can be movable fore and aft to adjust the position of the stimulator/sensor portion to engage the stimulator 454, 455 with a preselected muscle.

The housing 408 can be molded from suitable plastics or built with 3-dimensional printing, especially after photographic/video graphic impressions are made of one or all teeth, for example with a system such as Carestream dental imaging. These images can be used to make the housing 408 a single tooth just like putting on a temporary crown. This would be a removable, disposable or reusable option.

Figure 15:
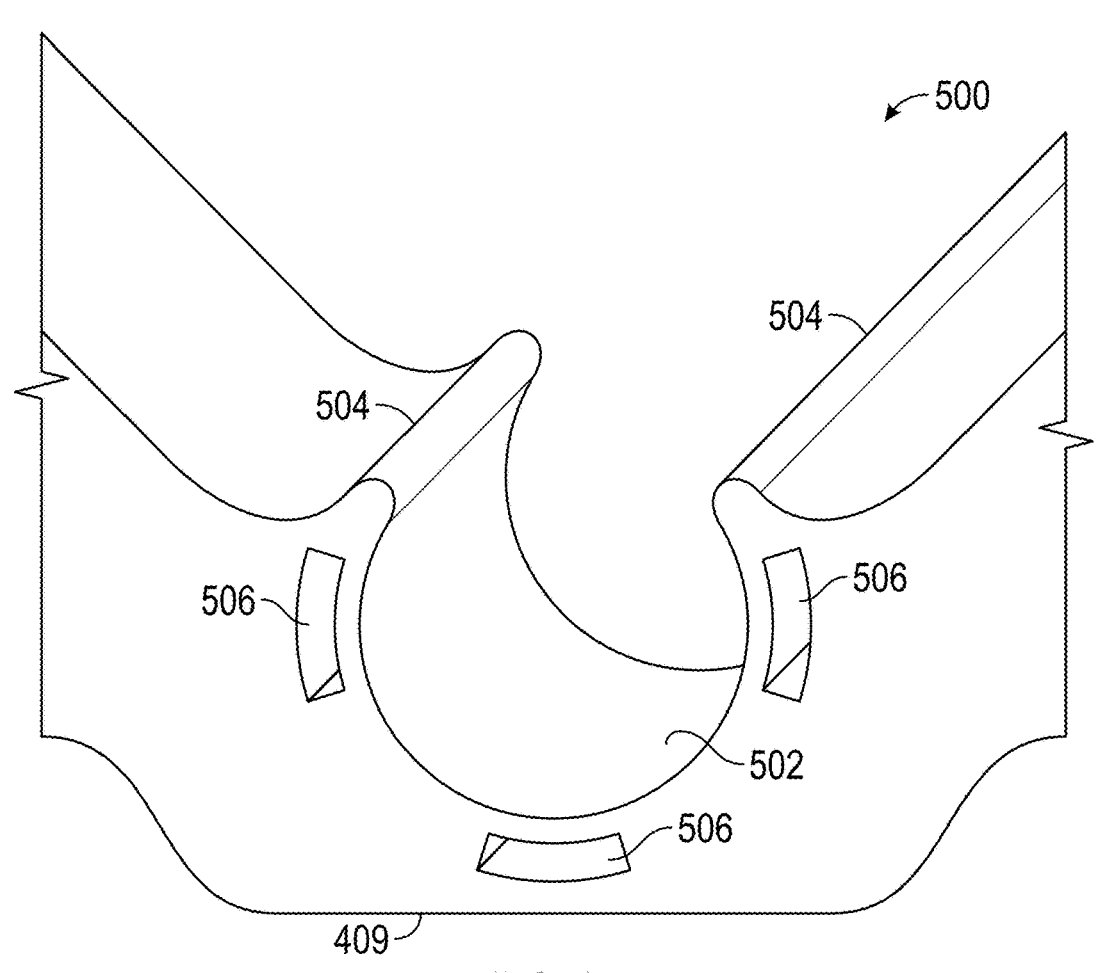
FIG. 15 is an enlarged view of a second embodiment of a connecting portion of the maxillary device.

Turning now to FIG. 15, an alternate embodiment of the tooth connecting portion 409 of housing 408 is shown. Here, the tooth connecting portion 409 defines a clasp 500 that is elastically deformable to fit over a single tooth or a plurality of teeth. The clasp 500 defines an arcuate shaped opening 502 that receive a tooth or teeth therein and has opposing teeth side flanges 504 that seat against opposite sides of the tooth/teeth or gums. The clasp 500 is made of an elastic material that will stretch open as it is fitted over a tooth/teeth and will then return to its original position for a tight fit against the tooth/teeth or gums. To enhance the elastic flexibility of the clasp 500, the body defining the arcuate shaped opening 502 can include a plurality of elongate, slightly arcuate bores 506 passing through the body in a juxtaposed arrangement to the arcuate shaped opening.

Figure 16:
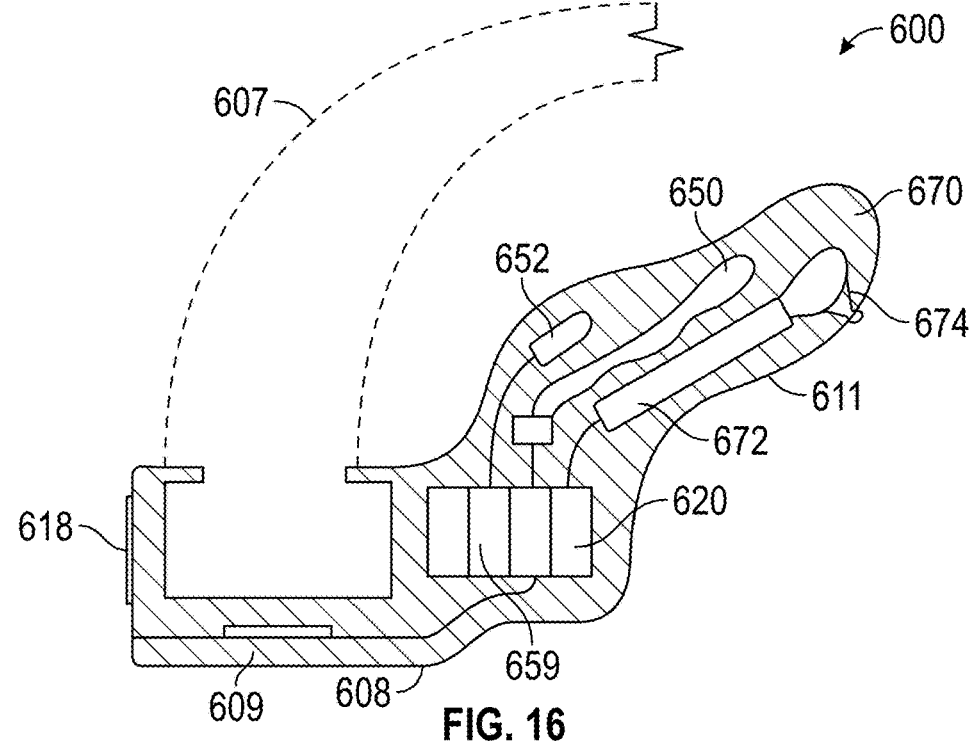
FIG. 16 is a longitudinal cross-sectional view of an embodiment of a maxillary device having a medicament dispenser.

Turning now to FIG. 16, a maxillary device 600 is shown that includes a medicament dispenser 670, but it could just as easily be any of the mandibular devices disclosed herein. The maxillary device 600 has a housing 608 connectable to a tooth of a user or connectable or integral with a teeth covering 607. The housing 608 encloses an on-board circuit board 659 and a power source 620 and comprises a tooth connecting portion 609, a palate housing portion 611 extending from the connecting portion, and a charging feature 618 in an exterior surface thereof for recharging the on-board power source 620. The palate housing portion 611 encloses therein a first sensor 650, and optional second sensor 452, and a medicament dispenser 670 each in electrical communication with a microprocessor of the on-bard circuit board 659. The on-board circuit board 659 receives data from sensors 650, 652 and activates the medicament dispenser 670 to dispense a medicament to a user's oral cavity as needed under pre-selected conditions.

The medicament dispenser 670 includes a reservoir housing 672 the medicament (i.e., a plurality of doses), which can be in pellet, tablet, powder, or liquid form, and a dispenser head 674 open or openable for communication with the oral cavity. The reservoir 672 is either refillable or removable replaceable with a filled reservoir. The reservoir 672 may be manufactured separated and is insertable into the cavity of the housing 611. The reservoir 672 can likely hold 1, or more doses, for example, 2, 3, or 4 doses of a pre-selected medicament. The total dose of all batches of medication would not exceed the total FDA approved dose for a specified period of time, exemplified by an 8 hour period. The size and spread of the medicament dispenser 670 may not be limited by the drawings and may extend over any portion of the hard and soft palate.

In one embodiment, the medicament is radiation pellets for treatment of oral cancer or immuno-therapy. In another embodiment, the medicament is trans-mucosal or sublingual drugs, for example, but not limited to, nitroglycerine, intermezzo, albuterol, ADVAIR® medicine. In an embodiment where the medicament is intermezzo, the sensor is an EEF, EOG, or EMG sensor to detect insomnia and thereafter dispense the intermezzo. In another embodiment, the medicament is nitroglycerine and the sensor is an EKG monitor. Additional sensors are beneficial with this embodiment, including a blood pressure sensor, echocardiography and/or carotid doppler blood flow. In a third embodiment, the medicament is a dry powder micro-aerosol inhalation of insulin to treat diabetes and the sensor is a non-invasive continuous glucose sensor. In a fourth embodiment, the medicament is a bronchodilator and the sensor is a microphone to detect breathing difficulties such as wheezing, for example in asthmatics.

In one embodiment, the medicament is in pellet form and the pellet is filled with a liquid or aerosolized form under pressure therein. The pellet is rupturable, meltable, pierceable. or dissolvable A rupturable pellet ruptures upon application of pressure, such as being squeezed by a driver of a piezo electric motor. A meltable pellet open upon application of heat, such as heat from the power source via a heating electrode. The pellet may have a predesignated location 674 that is made of meltable material or dissolvable material which upon disintegration releases the said medication or be an on-off robotically operated valve that opens to release pre-determined concentration or dose of medication and then shuts off. A pierceable pellet is opened by a micro-needle within housing 611. A dissolvable pellet could be simply ejected into the oral cavity and dissolves upon contact with saliva. Each pellet is a single dose unit of the selected medicament relative to the user.

As in the embodiment of FIGS. 1-3, up to four housings, a right and a left maxillary housing and a right and left mandibular housing, can be present and each could include a sensor and a medicament dispenser. As such, up to four or more medicament reservoirs 672 could be present and each can have a plurality of doses of a medicament. Different medications could be installed in different housing, each with an appropriate sensor for the medicament. If only one medication is installed in the user's device, then the medication and the sensor may be in the same housing or in different housings.

Figure 17:
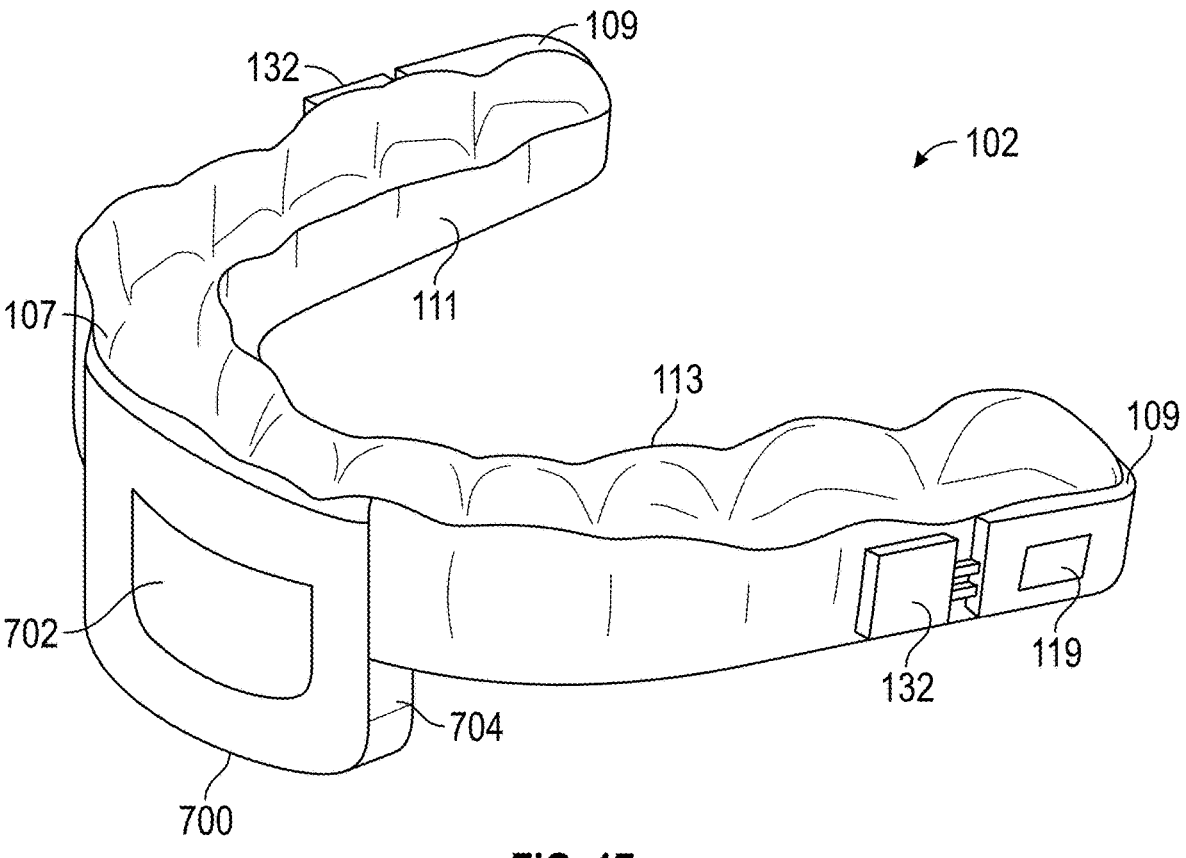
FIG. 17 is a left-side view of the maxillary device of FIG. 2 modified to include a digital camera or digital video recorder.

Turning now to FIG. 17, any of the maxillary devices disclosed herein may additionally include a forward facing photography/videography system 700, which includes a digital camera or video recorder 702 facing forward. The maxillary device here is the one from FIG. 2, modified to have an integrally molded recorder housing 704 which houses the digital camera or video recorder 702. The digital camera or video recorder 702 is electrically connected to the on-board circuit board within housing 109 or includes its own wireless transmitting system to send the data to the on-board circuit board within housing 109 or to an off-board microprocessor discussed below. Each of the features disclosed with respect to the maxillary devices of FIGS. 13-17 are equally applicable to any of the mandibular and maxillary devices of FIGS. 1-12.

Figure 5:
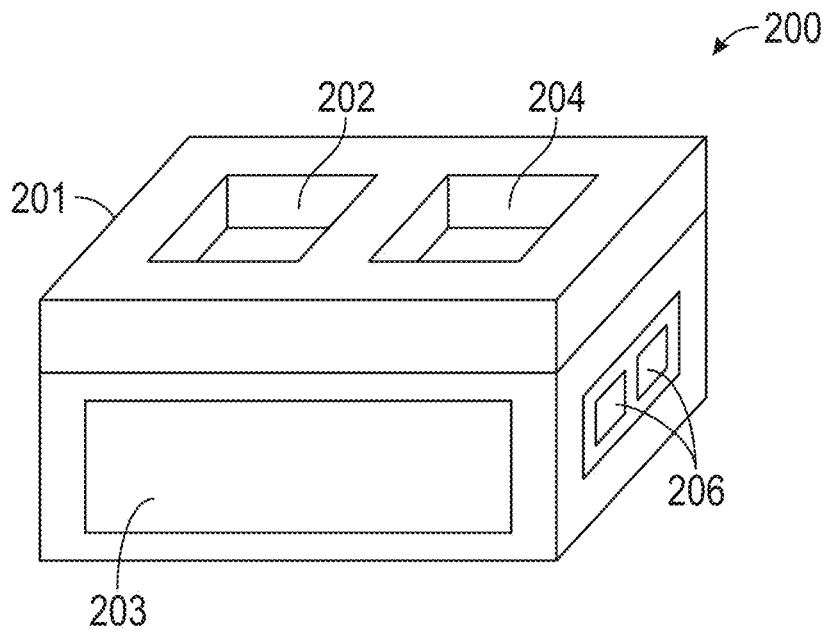
FIG. 5 is front, perspective view of a controller station for use with the devices disclosed herein.

Turning now to FIGS. 5 and 12, a controller station 200 is illustrated for operatively controlling any of the mandibular lingual repositioning devices 100, 101 described above, which together define a system 300 schematically illustrated in FIG. 12. The controller station 200 has a housing 201 defining a first charging unit 202 for receipt of the maxillary piece 102 and a second charging unit 204 for receipt of the mandibular piece 104. The first and second charging units 202, 204 may be receptacles defined in a surface of the housing 201. In another embodiment, the first and second charging units 202, 204 may be generally flat plates. The housing 201 has a display screen 203 for displaying information to a user and one or more ports 206 for connecting the charging station to power, other devices, and/or the internet. Alternately, instead of ports 206, the housing 201 can enclose wireless communication technology for other devices 310, for example, but not limited thereto, a printer, speakers, tablets, laptops, cellular phones, smart watches, and other cloud-based devices. The controller station 200 may include sensors to record ambient room conditions, such as light, temperature, humidity, noise/sound, etc. The controller station 200 optionally is battery powered and may include a rechargeable battery. The controller station 200 may be portable.

Alternately, rather than having the first and second charging units 202, 204 integrated into the controlling station 200, a separate charging station (not shown) having a first and second charging unit is possible. The charging station may be portable.

When the charging station is separate from the controller station 200, the controller station may be incorporated into a hand-held smart device and such a smart device would share blue tooth, WIFI, Video, audio and communication capability with sensors. In one embodiment, the controller can be a proprietary software program for use with or an App (software application) having full functionality to function like the controller station 200. System 300 and controller station 200 in all its embodiments will be HIPPA and HITECH compliant for purpose of medical privacy. Interface with the wide variety of electronic health formats (EHR) would allow system 300 and controller station 200 and its operated systems to be available for real-time data download and upload, active health care worker involvement in user's health care needs and would permit the health care worker to operate and alter any treatment and access and interpret diagnostic information provided by the system. As such controller station 200 and system 300 would allow newer formats of health care provisions such as tele-medicine and others yet to be defined. System 300 may be integrated into a full-function health care software-hardware system for patient assessments (such as telemedicine), tests, treatments and medications.

The controller station 200 encloses a circuit board having a microprocessor, including memory (non-transitory computer readable media) in which is stored firmware and learning algorithms, having a receiver of electronic communications, and having a transmitter of electronic communications, including wireless communication capabilities to electronically communicate with at least the MLRD 100, 101 for real-time communications with the sensors on board the MLRD. The MLRD 100, 101 has microprocessors on-board with a transmitter to transmit raw data from all sensors, stimulators and pressure pellets exemplified by the pulse oximetry sensor, the vibration and airflow sensor, lingual stimulator, lateral pterygoid stimulator, medial pterygoid or masseter stimulator, EKG sensor, sub-lingual nitroglycerine pellet discharge, etc. to the controller station 200 in real-time aided by system 300 for processing into executional commands exemplified by movements of the first driver and/or the second driver and activation of the stimulator for tandem or synchronized movements and activation thereof, i.e., simultaneous, independent, or sequential activation of the motors and the stimulator, training of muscles of speech or swallowing including the sequence of movement and strength and duration of current or release of a medication for sublingual or aerosolized use. The controller station 200 can simultaneously transmits the instructions to the MLRD 100, 101 microprocessors in each housing 108, 109, 108' which implement the instructions, exemplified by synchronizing the cranial to caudal adjustments, the anterior to posterior adjustments, and activation of the stimulator etc. The MLRD may also operate as a stand-alone mandibular protrusive and vertical advancement device or as a stand-alone lingual/pterygoid stimulator device or a timed-medication release device as preferred by treating health care provider.

The circuit board of the controller station 200, in one example, receives data from the MLRD that includes but is not limited to pulse oximetry sensor and/or the vibration and air sensor and activates the motors and the stimulator as needed after a pre-selected number of breaths of the user. The firmware and algorithms, including learning algorithms as well as standard algorithms, stored in the memory of the circuit board may define the pre-selected number of breaths to be every breath, every other breath, every five breaths, or an absence of breath(s). Since the movements of the MLRD 100, 101 are done in real-time, the airway of the user can be opened without disturbing the sleep or wake related fitness or any other activity of the user. Algorithms designed to record, interpret, and analyze, execute commands, and facilitate servo feedback functions will contain tolerance range, critical values, and reportable values. Similar application may be appropriate for sports, athletics, performance, and military users. The controller station may be miniaturized using PIC/QMC microprocessors in a hand-held device or wearable apparatus, such as a wristwatch, wrist band, helmet, waist belt, etc. or may be incorporated into an aircraft or space-ship's internal computing system.

The controller station 200 has a microprocessor configured to process the data and instruct the MLRD 100, 101. However, the controller station 200 can communication with a server, such as a cloud server, for further processing if desired, or for additional memory storage and/or communication of the data to authorized healthcare providers and/or sleep analysis experts, etc. and/or communicate with a database of said person. This intercommunication of databases can create therapeutic interventions and diagnostic testing of a user while at home, in place of work, outer space, or anywhere in the world. This system 300 enables an authorized healthcare provider with capability to monitor and record patient data in real time, learn the patient, and alter the patient's treatment in real-time. The communications to and from the server can be through a wired or a wireless connection. The system 300 can also be configured to send data to a pharmacy, emergency medical services or HIPPA validated designated caregiver.

The server can also send commands, configuration data, software updates, and the like to the controller station 200. The configuration data may include, but is not limited to, configuration parameters for the system 300, configuration parameters for a particular user, and/or notifications, feedback, instructions, or alerts for the user.

The system 300, in addition to the MLRD 100, 101 can wirelessly communicate with additional sensors connected to the user to provide a broader data set for a more complete picture of the user's physiology. For example, electrocardiogram (EKG), electromyography (EMG), electrooculography (EOG), electroencephalography (EEG) sensors, echocardiography, blood pressure monitoring systems, and sensors sensing environmental conditions, such as temperature, ambient light, and humidity. The system may include a camera for video recording through the controller station 200 to evidence any nocturnal seizures, sleep-walking, other movement or violent disorders during sleep.

In operation, data from the sensors on the MLRD 100, 101, such as oxygen measurements and pulse data, is sent to the controller station 200 to be processed by the microprocessor to determine how much movement of the protrusive flange by activation of the second driver is needed, how much movement of the first driver is needed to separate the jaws of the user, and if and when to stimulate the transverse lingual muscle of the tongue to move the tongue forward. After some breaths, the controller station 200 may determine to stimulate the tongue and activate the second driver to move the mandibular piece, and hence the jaw of the user, forward (anterior) or backward (posterior) direction. In other instances, the controller station 200 may determine to stimulate the tongue and activate both the first driver and the second driver to separate the jaws and move the mandibular piece forward in order to adequately open the airway of the user.

The system 300 also creates three-dimensional images and videos of breathing, cardiac function, carotid blood flow data, eye-movements, jaw movements and brain EEG recordings for identification of medical conditions and interventions that may be useful to correct or treat those medical conditions.

A unique advantage of this system over any other existing systems is that the jaw and tongue can move synchronously, independently, or sequentially during sleep or during wake-related activities, in real-time and in anticipation of impending airway closure or changes in physiology, and in a provision of a measured response to those changes such as relief from restriction of airflow as determined by the controller station 200 even before the airway has completely closed; thus, restoring unrestricted airflow even before the patient has completely stopped breathing (as in sleep apnea). This system can see airway obstruction before it happens and will keep the airway constantly open in any body position or depth of sleep. This is a distinct advantage over CPAP/BIPAP or any other mechanical or electrical system that is commercially available in the market. In addition, there are distinct advantages just by the breadth of functionality that has been described above.

The controller station 200 includes learning algorithms in the memory of the microprocessor that learns a user's sleep patterns and other physiological events and functions during sleep and wake, pathological events and activities during wake and sleep from the data collected over time and creates a "best response" for the simultaneous, independent, or sequential responses exemplified by tensing of the soft palate or Uvula, release of medication or stimulation of the stimulator and activation of the first and second drivers to open the airway or to train muscles of speech, and to synchronize these best responses such as exemplified by certain jaw movements that are associated with particular phases of respiration. The activation of the first and second drivers 130, 132 not only includes advancements, but also retractions of the first and second drivers 130, 132 to relax the jaws in between necessary advancements to open the airway to avoid potential TMJ problems. Any discussions herein directed to the mandibular component, with respect to the controller station 200 and the system 300, are equally applicable to the maxillary component.

The controller station 200, in the memory of the microprocessor, may include a pre-programmed range for the movements of the first and second drivers 130, 132 based on sleep study data for the user conducted by an authorized healthcare provider. The pre-programmed range can be used by the controller station 200 in a stand-alone or auto servo mode. The pre-programmed range may be determined by simple or multiple linear regression models that employ data from inputs and from previous experiences, which the controller station 200 will be able to forecast ranges for the amount and direction of movements of the drivers 132, 134 and the amount or timing of energy discharge through the transverse stimulator(s). The controller station 200, in the memory of the microprocessor, may include data from tests previously performed on the user and/or the output of algorithms to set the MLRD 100, 101 each day for use just prior to sleep.

The controller station 200 can operate based on a stand-alone function or a servo function. In the standalone function, the controller station 200 operates the MLDR 100, 101 based on set parameters for the movement of the drivers, such as repetitive equal advancement and retraction of the mandible that are not based on active feedback. For example, a set 2 mm movement anteriorly of the mandible during each breath and a 2 mm posterior movement of the mandible after each breath, with a fixed amount of energy discharge to the electrode of the stimulator. The set parameters for the standalone function may be based on data collected from the specific user or may be based on a peer group of like sleep attributes.

In the servo function, the controller station 200 interactively controls the MLRD 100, 101 during sleep or wake, at home or elsewhere, based on the data collected from the sensors on-board the MLRD in a feedback loop and based on data available from the server. During operation, the continual feedback loop allows incrementally accurate interventions followed by listening to observational inputs exemplified by airflow measurements, video recordings, pulse-oximetry, doppler flow in carotids or advancement of mandible and followed by more interventions exemplified by protrusive or vertical adjustments based on real-time data even after a previous advancement or incremental increase in energy to stimulate the tongue. The changes to the advancement or application of energy to the stimulator will be capable of producing positive and negative changes regarding movement of the mandible and tongue. For example, the energy applied to the stimulator may be reduced relative to the prior application of energy discharge if the previous discharge of energy caused teeth grinding or cough. In another example, the protrusive movement of the jaw may be reversed if the previous protrusion advancement caused a deleterious change in any of the monitored physiological parameters. In another example training of muscles of swallowing would be altered upon observing retrograde movement of food or appearance of cough or gag.

Also, in the servo function, data from all sources, server, MLRD, and any other sensors attached to the user that are communicating with the controller station 200, are continuously processed through algorithms that are stored in the memory of the controller or stored in the server. Examples of other sensors includes, but is not limited to, wireless pulse-transit time sensors, and wireless EKG sensor. These two additional sensors would be utilized in addition to the MLRD to diagnose and treat sleep-induced hypertension and/or cardiac arrhythmia such as lack of oxygen to the heart, especially by collecting time synchronized data from the EKG sensor and the pulse oximeter sensor. For example, the server may include data related to sleep attributes and alcohol consumption to make adjustments for the user during sleep after drinking alcohol. For example, it may require a change in current applied to the stimulators 116 after alcohol consumption to effectively stimulate the lingual muscles. The same may be true of a user taking certain medications, especially those that depress brain function. As another example, the server may include data on myriad patients correlating sleep attributes to weight loss. As such, if the user loses 5 or 10 pounds, data from the server can be considered in the algorithm determining how much movement of the jaws is needed and/or whether to stimulate the tongue.

The system 300 may be used to treat many medical diseases, including but not limited to any type of sleep apnea, bruxism, sleep related GERD, sleep-induced hypertension, snoring, etc.

The system 300 may be used to diagnose any possible medical conditions related to sleep or while awake, including sleep apnea or other sleep disorders including sleep-induced hypertension, sleep-related cardiac arrhythmia, sleep related seizures, RLS and periodic limb movement disorders and other medical diseases, even those unrelated to sleep. Here, the MLRD 100 or 101 is placed in the user's mouth during a sleep period, such as at night, with the controller station 200 in a "test mode" in which the on-board sensors measure and monitor the user's physiological parameters mentioned above. The test mode is used for multiple sleep periods of over two to 30 days, based on a time period set by a medical professional. For example, the user may have the controller station in "test mode" for seven days. Then, the seven days of data is reviewed by the medical professional to determine whether the user has sleep apnea or any other sleep disorder, and if so, determines the parameters for the standalone mode, which are then stored in the controller station 200. The same system may be used even during the day and outside of the home of the user such as at place of work.

The system 300 may have a therapeutic mode, which implements the servo function. Here, the feedback loop is on for data from the on-board sensors, which is processed through an algorithm to determine the least amount of anterior and caudal movement to maintain an open airway and the least amount of energy discharge to stimulate the tongue and maintain an open airway and the order in which to take such actions, i.e., simultaneously, sequentially, or individually.

The device and system disclosed herein have numerous advantages, including artificial intelligence utilizing data collected by the MLRD during use to actively in real-time adjust the MLRD in response to the phases of respiration, degree of obstruction of the airway, snore sounds and vibrations and amount of hypoxemia present relative to each breath irrespective of the stage of sleep of the user. The system is capable of measuring a large number of cardiac, neurological and endocrine sensory inputs as described above exemplified by continuous non-invasive glucose, oxygen, blood pressure, pH monitoring, heart rhythm and temperature etc. The system is capable of photography for creating dental impressions, dentures or to diagnose gum disease etc. The system is capable of executing a large spectrum of functions such as mandible protrusion, administering sub-lingual insomnia medication like Intermezzio or cardiac medication like nitroglycerine or training muscle groups for swallowing or speech. The system is capable of communicating with user, provider, EHR (Electronic Health Record) and pharmacy etc. This system is capable of determining restriction to airflow, increase in velocity of air and turbulence, decreasing levels of oxygen and increasing levels of heart rate, pH monitoring and any other physiological parameter that could be installed in the future with constant inputs of physiological parameters (unlike with CPAP machine or oral appliances that are available in the industry), such as those mentioned above. This 24 hour a day seven days a week capability of collection and processing of data allows the system to actually make adjustments exemplified by the movement of the mandible and tongue prior to closure of the airway and hence will work as a preventative form of treatment for sleep apnea.

Age and gender specific physiology of the airway and the mouth during sleep are known to affect sleep and cause sleep disorders. The system 300 and 310 will collect data that will enable the development of algorithms that are age and gender specific, which can improve treatment outcomes for future users. System 300 and 310 has ability to create database of all physiological and pathological events measured in real-time and time synchronized with each other in its users and develop algorithms for normal and abnormal manifestations of disease states during wake and sleep and develop new cause-and-effect understanding of these events that have never been observed before. Recording and correlation of these phenomenon with sensors, especially during sleep would help understand conditions such as 'wake-up strokes' (occur during sleep) that account for 14% of all strokes and diagnose conditions like obstructive sleep apnea that occurs with almost 83% of cardiovascular disease, 58% of heart failure and 53% of atrial fibrillation, to name a few.

The system not only advances movement of the mandible (cranially and anteriorly), but enables a relaxed movement of the mandible (caudally and posteriorly), which allows the temporomandibular joint to relax periodically to prevent jaw discomfort, temporomandibular joint strain and destabilization, morning stiffness of said joint, and alteration of the user's bite.

The system 300 can also be used for users that snore, but who do not yet have sleep apnea. The inclusion of the vibration and airflow sensor enables the measurement of the intensity of snoring and can open the airway before the sub-sonic snore has become audible. The inclusion of stimulators of soft palate and uvula can reduce or eliminate snoring in users that do not have sleep apnea yet. Also, the system 300 can be used along with a CPAP machine and enable the CPAP machine to be used at a lower air pressure than a typical setting for user's that cannot tolerate CPAP machine at their typical air pressure.

In one example, the devices disclosed herein are worn by a user at nighttime and includes sensors to monitor nocturnal silent angina or myocardial ischemia (measured by continuous EKG monitoring) that could cause sudden death or acute myocardial infarction during sleep or wake (especially silent ischemia). With the medical dispenser present, an incident could be treated with release of sublingual nitroglycerine from medicament reservoir while data such as continuous blood pressure recording, EKG, echocardiography and carotid doppler blood flow is continuously recorded and transmitted to the controller station 200 or cloud server 300. The cloud server 300 can then send the data to a monitoring on-call physician, a handheld device or computer to alert the patient, as well to the nearest ER/ED (emergency room) for early ambulance dispatch.

In other examples, the sensors selected for use in the maxillary and mandibular devices disclosed herein can be those that can diagnose cardiovascular, gastrointestinal, and/or neurological medical conditions. The devices can have sensors and treatment methods to treat the same medical conditions.

In an athletic environment, the sensors selected for use in the maxillary and mandibular devices disclosed herein can be the pulse-oximetry, heart rate and EKG, PTT with non-invasive blood pressure recording, carotid blood flow, airway resistance and total tidal volume (airflow measurement per breath), EEG recording, respiratory rate measurement, and combinations thereof. Data from these sensors will allow determination of performance restrictions and methods to physiologically improve performance such as legal nutritional supplementation or medications for underlying medical conditions or increasing the size of airway to help improve oxygenation and reduce heart rate during exercise or athletic performance. Further, evaluation of concussion injuries is possible with maxillary and mandibular devices that have EEG sensors, carotid doppler blood flow ultrasound sensor, airway and airflow sensors. The protrusive aspect of the devices can improve airflow after a concussion by increasing the size of airway with electrical stimulation of the tongue when the athlete is unconscious, thereby reducing brain injury from loss of oxygen.

System 300 can be used for scheduled timed administration of medication through the mechanisms and devices discussed above, especially for those medications best administered while the user is asleep.

When medicaments are being administered by the devices disclosed herein, the controller station 200 or system 300 would identify a physiological problem of the user from data received from the sensors and/or from data received from an external EKG monitoring system or external blood-glucose monitoring system of the user followed by generation of an executable instruction sent to the device's on-board microprocessor through wireless data system (blue tooth or other protocols) with back-up confirmation system for dangerous medications. The back-up may be the user themselves (smart phone or display screen of controller Station 200) or an on-call nurse or ER physician or authorized health care provider or tele-medicine through a smart handheld device or through videography/audio from a camera or video recorder in the mandibular or maxillary housing. Data related to administration of the medication would require a response the following day prompting replacement of discharged pellets or other forms of the medicament, a visit to the health care provider's office, or a tele-medicine visit.

It should be noted that the embodiments are not limited in their application or use to the details of construction and arrangement of parts and steps illustrated in the drawings and description. Features of the illustrative embodiments, constructions, and variants may be implemented or incorporated in other embodiments, constructions, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. Having described the invention in detail and by reference to preferred embodiments thereof, it will be apparent that modifications and variations are possible without departing from the scope of the invention which is defined in the appended claims.

What is claimed is:

1. A mandibular repositioning device comprising: a maxillary tooth covering having a first driver flange protruding laterally outward on a right side or a left side thereof, the first driver flange having an anterior side with a convex curvature; a mandibular tooth covering having a first protrusive flange extending cranially therefrom positioned to have a posterior side engaged with the anterior side of the first driver flange, the posterior side of the first protrusive flange has a base, a most cranial point, and has a concave-to-convex curvature from the base toward the most cranial point; wherein a convex portion of the concave-to-convex curvature engages the convex curvature of the first driver flange in a rest position and having a plateau of a preselected height between the base of the first protrusive flange and the tooth covering, wherein the plateau extending into or across the width of the mandibular tooth covering, thereby defining an opening at a front teeth position between the mandibular tooth covering and the mandibular tooth covering in the rest position; wherein downward movement of the mandibular piece moves the convex portion of the posterior side of the first protrusive flange along the convex curvature of the first driver flange, thereby being configured to move a user's mandible forward; wherein the preselected height of the plateau is configured to prevent disconnect between the first protrusive flange and the first driver flange relative to a fully open mouth.

2. The device as claimed in claim 1, wherein the maxillary piece has a housing proximate one or both of a left molar portion and a right molar portion, wherein each housing encloses a power source electrically connected to a motor and to a microprocessor and has a driver operatively connected to a rod enclosing a set of robotic arms, wherein a first robotic arm is configured to move the first driver flange for anterior-posterior movement and a second robotic arm is configured to change a lean of the first driver flange.

3. The device of claim 2, wherein the first robotic arm and the second robotic arm work synchronously to maintain contact between the first driver flange and the first protrusive flange.

4. The device of claim 3, further comprising one or more sensors configured to be positioned in the user's oral cavity in operative communication with the microprocessor within each housing and the microprocessor comprises nontransitory memory having stored therein a first algorithm controlling the synchronous movement of the first robotic arm and second robotic arm relative to data from the one or more sensors.

5. The device of claim 4, wherein the one or more sensors measure airway cross-sectional area, airflow volume, airflow velocity, systolic and diastolic blood pressure, electrical activity of the heart, oxygen level, and combinations thereof.

6. The device of claim 4, wherein the microprocessor comprises a quantum microchiplet and/or a photonic integrated circuit.

7. The device of claim 4, comprising position sensors measuring a first distance for cranial-caudal movement and a second distance for anterior-posterior movement of the first driver flange.

8. The device of claim 4, wherein the microprocessor comprises a second algorithm for anterior-posterior movement under the influence of medication, sedation, anesthesia, or alcohol.

9. The device of claim 2, wherein the motor is an electric and magnetic field (EMF) synchromesh motor and/or an induction motor.

10. The device as claimed in claim 1, wherein the plateau is wedge-shaped, has a first height at the anterior base of the first protrusive flange, a second height at the posterior base of the first protrusive flange, and the first height is greater than the second height.

11. The device as claimed in claim 10, wherein the plateau terminates posteriorly at the posterior base of the first protrusive flange and the first driver flange extends caudally with the anterior side extending the convex curvature thereof past the posterior base of the first protrusive flange into a gap defined by the plateau between the maxillary piece and the mandibular piece or extends caudally on the buccal side of the mandibular piece beyond the plateau of the mandibular piece.

12. The device as claimed in claim 11, wherein the first driver flange has a base that is seated on the mandibular piece.

13. The device as claimed in claim 10, wherein the first protrusive flange and the first driver flange are inclined equivalently to the plateau to maintain the engaged convex portion to convex curvature thereof.

14. The device as claimed in claim 10, wherein the first protrusive flange has a flange of or less than 20 mm.

15. The device as claimed in claim 10, wherein the plateau extends posteriorly to a posterior terminus of the tooth covering and terminates with a third height that is smaller than the first height and the second height.

16. The device as claimed in claim 1, wherein the first protrusive flange is removably and replaceably attached to the mandibular piece, and/or the first driver flange is removably and replaceably attached to the maxillary piece.

\* \* \* \* \*